(12) United States Patent
Spudich et al.

(10) Patent No.: US 9,676,836 B2
(45) Date of Patent: Jun. 13, 2017

(54) CDNA-DERIVED NUCLEIC ACIDS ENCODING RED-SHIFTED CHANNELRHODOPSINS

(71) Applicant: BOARD OF REGENTS OF THE UNIVERSITY OF TEXAS SYSTEM, Austin, TX (US)

(72) Inventors: John Lee Spudich, Houston, TX (US); Elena G. Govorunova, Houston, TX (US); Oleg A. Sineshchekov, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/789,702

(22) Filed: Jul. 1, 2015

(65) Prior Publication Data
US 2015/0299291 A1 Oct. 22, 2015

Related U.S. Application Data

(63) Continuation of application No. 14/053,129, filed on Oct. 14, 2013, now Pat. No. 9,102,747, which is a continuation of application No. 13/420,352, filed on Mar. 14, 2012, now Pat. No. 8,580,937.

(60) Provisional application No. 61/452,513, filed on Mar. 14, 2011.

(51) Int. Cl.
| | |
|---|---|
| *C07K 14/705* | (2006.01) |
| *C12N 1/16* | (2006.01) |
| *C12N 1/20* | (2006.01) |
| *C12N 5/04* | (2006.01) |
| *C12N 5/071* | (2010.01) |
| *C12N 5/079* | (2010.01) |
| *C12N 15/00* | (2006.01) |
| *C12N 15/09* | (2006.01) |
| *C07K 14/405* | (2006.01) |

(52) U.S. Cl.
CPC .......... *C07K 14/705* (2013.01); *C07K 14/405* (2013.01); *C12N 1/16* (2013.01); *C12N 1/20* (2013.01); *C12N 5/04* (2013.01); *C12N 5/0602* (2013.01); *C12N 5/0621* (2013.01); *C12N 15/00* (2013.01); *C12N 15/09* (2013.01)

(58) Field of Classification Search
CPC .... C07K 14/405; C07K 14/705; C12N 15/09; C12N 15/00; C12N 5/0621; C12N 5/0602; C12N 5/04; C12N 1/16; C12N 1/20

See application file for complete search history.

*Primary Examiner* — Robert Landsman
(74) *Attorney, Agent, or Firm* — Conley Rose, P.C.

(57) ABSTRACT

Methods and compositions are used to identify and characterize new channelrhodopsins derived from algae and several of which are red-shifted. The rhodopsin domain of these red-shifted channelrhodopsins can be cloned and expressed in mammalian systems and used in optogenetic applications and as therapeutic agents. Also provided are methods and compositions for use in red-shifting the absorbance maxima of channelrhodopsins in order to improve their utility for use in vivo.

13 Claims, 45 Drawing Sheets

SEQUENCE LISTING

```
<160> NUMBER OF SEQ ID NOS: 26

<210> SEQ ID NO 1
<211> LENGTH: 331
<212> TYPE: PRT
<213> ORGANISM: Mesostigma viride
<220> FEATURE:
<223> OTHER INFORMATION: Channelrhodopsin 1 (MChR1)

<400> SEQUENCE: 1

Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
                20                  25                  30

Ala Pro Cys Glu Glu Asp Cys Val Thr Ile Arg Tyr Phe Val Glu Asn
            35                  40                  45

Asp Phe Glu Gly Cys Ile Pro Gly His Phe Asp Gln Tyr Ser Ser His
        50                  55                  60

Gly Ser Leu His Asp Ile Val Lys Ala Ala Leu Tyr Ile Cys Met Val
65                  70                  75                  80

Ile Ser Ile Leu Gln Ile Leu Phe Tyr Gly Phe Gln Trp Trp Arg Lys
                85                  90                  95

Thr Cys Gly Trp Glu Val Trp Phe Val Ala Cys Ile Glu Thr Ser Ile
            100                 105                 110

Tyr Ile Ile Ala Ile Thr Ser Glu Ala Asp Ser Pro Phe Thr Leu Tyr
        115                 120                 125

Leu Thr Asn Gly Gln Ile Ser Pro Gln Leu Arg Tyr Met Glu Trp Leu
    130                 135                 140

Met Thr Cys Pro Val Ile Leu Ile Ala Leu Ser Asn Ile Thr Gly Met
145                 150                 155                 160
```

```
Ala Glu Glu Tyr Asn Lys Arg Thr Met Thr Leu Leu Thr Ser Asp Val
            165                 170                 175

Cys Cys Ile Val Leu Gly Met Met Ser Ala Ala Ser Lys Pro Arg Leu
        180                 185                 190

Lys Gly Ile Leu Tyr Ala Val Gly Trp Ala Phe Gly Ala Trp Thr Tyr
        195                 200                 205

Trp Thr Ala Leu Gln Val Tyr Arg Asp Ala His Lys Ala Val Pro Lys
        210                 215                 220

Pro Leu Ala Trp Tyr Val Arg Ala Met Gly Tyr Val Phe Phe Thr Ser
225                 230                 235                 240

Trp Leu Thr Phe Pro Gly Trp Phe Leu Leu Gly Pro Glu Gly Leu Glu
                245                 250                 255

Val Val Thr Gly Thr Val Ser Thr Leu Met His Ala Cys Ser Asp Leu
            260                 265                 270

Ile Ser Lys Asn Leu Trp Gly Phe Met Asp Trp His Leu Arg Val Leu
        275                 280                 285

Val Ala Arg His His Arg Lys Leu Phe Lys Ala Glu Glu Glu His Ala
        290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile
                325                 330

<210> SEQ ID NO 2
<211> LENGTH: 354
<212> TYPE: PRT
<213> ORGANISM: Chloromonas augustae
<220> FEATURE:
<223> OTHER INFORMATION: Channelrhodopsin 1 (CaChR1)

<400> SEQUENCE: 2

Met Asp Thr Leu Ala Trp Val Ala Arg Glu Leu Leu Ser Thr Ala His
1               5                   10                  15

Asp Ala Thr Pro Ala Thr Ala Thr Pro Ser Thr Asp His Ser Thr Pro
            20                  25                  30

Ser Thr Asp His Gly Ser Gly Glu Thr Phe Asn Val Thr Ile Thr Ile
        35                  40                  45

Gly Gly Gly His His Gly Gly His Ala Gly Pro Val Asp Asn Ser Ile
        50                  55                  60

Val Ile Gly Gly Ile Asp Gly Trp Ile Ala Ile Pro Ala Gly Asp Cys
65                  70                  75                  80

Tyr Cys Ala Gly Trp Tyr Val Ser His Gly Ser Ser Phe Glu Ala Thr
                85                  90                  95

Phe Ala His Val Cys Gln Trp Ser Ile Phe Ala Val Cys Ile Leu Ser
            100                 105                 110

Leu Leu Trp Tyr Ala Trp Gln Tyr Trp Lys Ala Thr Cys Gly Trp Glu
        115                 120                 125

Glu Val Tyr Val Cys Cys Ile Glu Leu Val Phe Ile Cys Phe Glu Leu
        130                 135                 140

Tyr His Glu Phe Asp Ser Pro Cys Ser Leu Tyr Leu Ser Thr Ala Asn
145                 150                 155                 160

Ile Val Asn Trp Leu Arg Tyr Ser Glu Trp Leu Leu Cys Cys Pro Val
                165                 170                 175

Ile Leu Ile His Leu Ser Asn Val Thr Gly Leu Ser Asp Asp Tyr Gly
            180                 185                 190
```

```
Arg Arg Thr Met Gly Leu Leu Val Ser Asp Ile Ala Thr Ile Val Phe
            195                 200                 205

Gly Ile Thr Ala Ala Met Leu Val Ser Trp Pro Lys Ile Ile Phe Tyr
210                 215                 220

Leu Leu Gly Phe Thr Met Cys Cys Tyr Thr Phe Tyr Leu Ala Ala Lys
225                 230                 235                 240

Val Leu Ile Glu Ser Phe His Gln Val Pro Lys Gly Ile Cys Arg His
            245                 250                 255

Leu Val Lys Ala Met Ala Ile Thr Tyr Tyr Val Gly Trp Ser Phe Phe
            260                 265                 270

Pro Leu Ile Phe Leu Phe Gly Gln Ser Gly Phe Lys Lys Ile Ser Pro
            275                 280                 285

Tyr Ala Asp Val Ile Ala Ser Ser Phe Gly Asp Leu Ile Ser Lys Asn
290                 295                 300

Met Phe Gly Leu Leu Gly His Phe Leu Arg Val Lys Ile His Glu His
305                 310                 315                 320

Ile Leu Lys His Gly Asp Ile Arg Lys Thr Thr His Leu Arg Ile Ala
            325                 330                 335

Gly Glu Glu Lys Glu Val Glu Thr Phe Val Glu Glu Glu Asp Glu Asp
            340                 345                 350

Thr Val

<210> SEQ ID NO 3
<211> LENGTH: 355
<212> TYPE: PRT
<213> ORGANISM: Chlamydomonas yellowstonensis
<220> FEATURE:
<223> OTHER INFORMATION: Channelrhodopsin 1 (CyChR1)

<400> SEQUENCE: 3

Met Asp Thr Leu Ala Trp Val Ala Arg Glu Leu Leu Ser Ser Gly His
1               5                   10                  15

Gly Thr Asp Thr Ala Thr Asp Ser Gly His Gly Thr Asp Thr Ser Gly
            20                  25                  30

Gly His Asp Ser Ser His Asp Ala Val Ala His Asn Val Thr Leu Leu
        35                  40                  45

Ile Ala Pro Pro His Ala Gly Gly His Ala Gly Pro Thr Asp Thr Ser
50                  55                  60

Gln Gln Ile Thr Gly Ile Asp Gly Trp Ile Ala Ile Pro Ala Gly Asp
65                  70                  75                  80

Cys Tyr Cys Ala Gly Trp Tyr Val Ser His Gly Ser Ser Phe Glu Ala
            85                  90                  95

Thr Phe Ala His Val Cys Gln Trp Ser Ile Phe Ala Val Cys Val Leu
            100                 105                 110

Ser Leu Leu Trp Tyr Ala Tyr Gln Tyr Trp Lys Ala Thr Cys Gly Trp
        115                 120                 125

Glu Glu Val Tyr Val Cys Cys Ile Glu Leu Val Phe Ile Cys Phe Glu
130                 135                 140

Leu Tyr His Glu Phe Asp Ser Pro Cys Ser Leu Tyr Leu Ser Thr Ser
145                 150                 155                 160

Asn Val Val Asn Trp Leu Arg Tyr Ser Glu Trp Leu Leu Cys Cys Pro
            165                 170                 175

Val Ile Leu Ile His Leu Ser Asn Val Thr Gly Leu Ser Asp Asp Tyr
            180                 185                 190

Gly Arg Arg Thr Met Gly Leu Leu Val Ser Asp Ile Ala Thr Ile Val
```

```
                195                 200                 205
Phe Gly Val Thr Ala Ala Met Leu Val Asn Trp Pro Lys Ile Ile Phe
210                 215                 220
Tyr Leu Ile Gly Phe Thr Met Cys Cys Tyr Thr Phe Phe Leu Ala Ala
225                 230                 235                 240
Lys Val Leu Ile Glu Ser Phe His Gln Val Pro Lys Gly Ile Cys Arg
                245                 250                 255
His Leu Val Lys Ala Met Ala Ile Thr Tyr Phe Val Gly Trp Ser Phe
                260                 265                 270
Phe Pro Leu Ile Phe Leu Phe Gly Gln Ser Gly Phe Lys Lys Ile Ser
                275                 280                 285
Pro Tyr Ala Asp Val Ile Ala Ser Ser Phe Gly Asp Leu Ile Ser Lys
                290                 295                 300
Asn Ala Phe Gly Met Leu Gly His Phe Leu Arg Val Lys Ile His Glu
305                 310                 315                 320
His Ile Leu Lys His Gly Asp Ile Arg Lys Thr Thr His Leu Arg Ile
                325                 330                 335
Ala Gly Glu Glu Lys Glu Val Glu Thr Phe Val Glu Glu Glu Asp Glu
                340                 345                 350
Asp Thr Ala
        355

<210> SEQ ID NO 4
<211> LENGTH: 352
<212> TYPE: PRT
<213> ORGANISM: Chlamydomonas raudensis
<220> FEATURE:
<223> OTHER INFORMATION: Channelrhodopsin 1 (CrChR)

<400> SEQUENCE: 4

Met Ala Ser Met Ala Phe Ser Ala Ile Ser Leu Ala Ser Ser Ala Met
1               5                   10                  15
Arg Ser Leu Gln Ala Ser Gly Gly Asn Pro Phe Glu His Asp Ala Pro
                20                  25                  30
Pro Asp Asn Ser Cys Glu Leu Thr Pro Tyr Gly Cys Leu Asn Asp Phe
            35                  40                  45
Tyr Cys Asn Pro Ala Tyr Gly Leu Ala Asp Ala Gly Tyr Asn Tyr Cys
50                  55                  60
Tyr Val Gln Ser Ala Tyr Gly Lys Leu Ala Ile Val Gln Thr Asp Gln
65                  70                  75                  80
Leu Ser Trp Leu Tyr Ser His Gly Ser Ser Gly Ala Lys Ala Ala Ser
                85                  90                  95
Ile Ala Phe Gln Trp Leu Ala Phe Ala Thr Ala Val Ile Gly Leu Met
                100                 105                 110
Phe Tyr Ala Trp Asp Thr Trp Arg Ala Thr Thr Gly Trp Glu Glu Val
                115                 120                 125
Tyr Val Cys Thr Ile Glu Leu Ile Lys Val Leu Ile Glu Ile Phe Lys
                130                 135                 140
Glu Phe Glu Phe Pro Cys Ser Leu Tyr Leu Pro Thr Gly Asn Trp Val
145                 150                 155                 160
Leu Trp Leu Arg Tyr Ala Glu Trp Leu Leu Thr Cys Pro Val Ile Leu
                165                 170                 175
Ile His Leu Ser Asn Ile Thr Gly Leu Lys Asp Asp Tyr Asn Lys Arg
                180                 185                 190
Thr Met Arg Leu Leu Val Ser Asp Ile Gly Cys Ile Val Trp Gly Val
```

```
                195                 200                 205
Thr Ser Ala Met Thr Ala Gly Tyr Leu Lys Trp Ile Phe Phe Ala Ile
    210                 215                 220
Gly Leu Leu Tyr Gly Ser Asn Thr Tyr Phe His Ser Ala Lys Val Tyr
225                 230                 235                 240
Ile Glu Ala Tyr His Thr Val Pro Lys Gly Arg Arg Val Ile Val
                245                 250                 255
Arg Leu Met Ala Tyr Cys Phe Tyr Leu Ala Trp Thr Met Phe Pro Ile
            260                 265                 270
Leu Phe Ala Leu Gly Pro Glu Gly Met Gly Gln Met Ser Ala Tyr Met
            275                 280                 285
Ser Thr Ile Leu Thr Thr Ile Ala Asp Val Leu Ser Lys Gln Ile Trp
        290                 295                 300
Gly Leu Leu Gly His His Leu Arg Val Lys Ile Tyr Gln His Ile Leu
305                 310                 315                 320
Ile His Gly Asp Ile Arg Lys Lys Thr Thr Met Gln Val Gly Glu
                325                 330                 335
Asp Val Glu Val Glu Glu Phe Val Asp Glu Asp Glu Glu Gly Val
            340                 345                 350

<210> SEQ ID NO 5
<211> LENGTH: 2735
<212> TYPE: DNA
<213> ORGANISM: Mesostigma viride
<220> FEATURE:
<223> OTHER INFORMATION: channelopsin 1 mRNA

<400> SEQUENCE: 5
ctttacacgc aagcgacctt atttcccgga tagatatctg atggccgctg caaaatcgga    60
gcggtgagct acgcgaagcc taccgatcga gtgggcagtg ccatgtcgc cgccaacctc   120 gccgacgccg gacacgggac acgacacgcc ggacacggga cacgacacgg aggacacgg   180 agcggtggag atttgttttg ctccttgtga ggaagattgt gtcacgatta gatactttgt   240
cgaaaatgat ttcgagggat gcatacctgg ccatttcgac cagtacagct cgcatggttc   300
cctccacgac attgttaaag ccgcgctgta catttgcatg gtgatatcga ttctccaaat   360
cctgttctac ggttttcaat ggtggagaaa gacttgcggg tgggaagtgt ggttcgtcgc   420
ttgcatcgag acgtcgatct acattatcgc catcacgtcc gaagcagatt ctcccttcac   480
gctgtatctc accaatggac aaatctctcc gcaactccga tacatggagt ggctgatgac   540
atgtcctgtc attctgatcg cactctcgaa catcacgggc atggcggagg agtacaacaa   600
gcgcacgatg acgctgctca cgtcggatgt gtgctgcatt gtgctgggca tgatgtcggc   660
cgcctccaag ccaaggctca agggtatcct gtacgcagtc ggctgggcgt ttggtgcatg   720
gacatactgg actgcgctcc aggtctaccg tgacgcgcac aaggccgtgc ccaagcccct   780
cgcgtggtat gtgcgcgcga tgggctacgt gttcttcacc agctggctga ccttccccgg   840
gtggttccta ctggggcccg agggcttgga ggtggtcacg ggcactgtgt ccacgctcat   900
gcacgcatgc tccgacctta tcagcaagaa cctgtggggc ttcatggact ggcacctgcg   960
cgtgcttgtc gcgcgccacc accgcaagct cttcaaggcc gaggaggagc atgcgctcaa  1020
gaaggggcag acgctcgagc cgggcatgcc gcgcagcacg agctttgtcc ggggcctcgg  1080
cgatgacgtc gagatcgacc cctcgtacga gctttaccgc cttaagcggc agaaccaccc  1140
cgagtacttc ctctcgcctg cgcagacgcc gcgccgcggg ccgtcatttg acaagcgtac  1200
```

```
cagctttgag atggacgggg gcaagaacgg catgctgcag atgatgcccg tgactggcat    1260
gggcatgggc atggggatgg gcatgggtgg cggcaagacc gtgctcttcc tcgactacac    1320
gggcggcggg tacgtcagct tcttcgagca gcagctgtcg aacatgggcg tgaacgtgac    1380
taagtgctgg tccgatgacg acatgtacaa cacggccggc gttgccaacg tgaagcagtt    1440
gttccacttt gcgatgatcc ccaacaacgc gctcggggg cagatggtca tggacctgcg    1500
cgggacgggc ctgctggtgg tcgcctatgg ccccgagccg cccatgcccg gcatgggcca    1560
ggatgagttt gtcccgctcc agatgcccgg tgtgccgtac gacgagtcca tcctccacaa    1620
cctggtcatg cgccacgcga tcacgcaggg cttgggcatg aacggcatgc agggcaacat    1680
gggccagcag cagcagatga tgggcatgca gggcaacatg aacggcatgc agggcaacat    1740
gaatggcatg cagggcaaca tgaatggcat gcagggcaac atgagcggca tgcagggcaa    1800
catgaacggc atgcagggca acagcggcat gaaccaggga tggaacaacc aggggttcac    1860
caacacgggg gcctttggat actgaaggct gatgttgacc cctgacctga tgacctcaag    1920
acttgatagg gcttgatttt cgaccgcatc tgctggctgc gccattggct tgttttactc    1980
gctgtgccac tgaaagcatg gtttaccttt cttaggttcc tctgtggcgc tattgatagg    2040
ccttcttggt aaaaggcttg cagcacaaag gctttgacaa tcccgacata gaggactgct    2100
gtgtgtggcg ggttttcgtt tagtggccgg gtgattgtgt cttttgggg tgacgcttct    2160
tgtactgccc ccctggtttg ccggcggttt gggtatttag tgacctgtct tttctttttt    2220
cctttttaat gggggcataa acactctggg accgaaattg agtttgtgta gggcgcattt    2280
tatgtgattt ttaccgtagc acgccttgtg ctagcgagtg agccgtggtc atgccactag    2340
catggtcatg ccactagcat ggtcatgcca ctagcatggt catgcttttg agagagcctt    2400
gtaaaggcgt ttttttttgt cggcacggaa ttcgcgatgg ggctattttg catagcatcg    2460
ctcaccacaa caatgagtga gcttgtttgt tagtgtttgc gtggtaagtt ttctaggtct    2520
cgatatcatt ttgtagcttt tttactctag tgaagtttat tgcatgcagt tctcttgtt    2580
ttgtagtgtc aatgctagct atgtaaaagc ttttggtgt cttcgattgt gtacaggttg    2640
tctttgcgac ttgaattgaa ttgaattgaa ttgtaacata actccgttgg gagtaaaaaa    2700
aaaggaaaaa aaaaaaaaa aaaaaaaaaa aaaa                                 2735
```

<210> SEQ ID NO 6
<211> LENGTH: 593
<212> TYPE: PRT
<213> ORGANISM: Mesostigma viride
<220> FEATURE:
<223> OTHER INFORMATION: channelopsin 1

<400> SEQUENCE: 6

```
Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
            20                  25                  30

Ala Pro Cys Glu Glu Asp Cys Val Thr Ile Arg Tyr Phe Val Glu Asn
        35                  40                  45

Asp Phe Glu Gly Cys Ile Pro Gly His Phe Asp Gln Tyr Ser Ser His
    50                  55                  60

Gly Ser Leu His Asp Ile Val Lys Ala Ala Leu Tyr Ile Cys Met Val
65                  70                  75                  80

Ile Ser Ile Leu Gln Ile Leu Phe Tyr Gly Phe Gln Trp Trp Arg Lys
                85                  90                  95
```

-continued

```
Thr Cys Gly Trp Glu Val Trp Phe Val Ala Cys Ile Glu Thr Ser Ile
            100                 105                 110

Tyr Ile Ile Ala Ile Thr Ser Glu Ala Asp Ser Pro Phe Thr Leu Tyr
            115                 120                 125

Leu Thr Asn Gly Gln Ile Ser Pro Gln Leu Arg Tyr Met Glu Trp Leu
        130                 135                 140

Met Thr Cys Pro Val Ile Leu Ile Ala Leu Ser Asn Ile Thr Gly Met
145                 150                 155                 160

Ala Glu Glu Tyr Asn Lys Arg Thr Met Thr Leu Leu Thr Ser Asp Val
                165                 170                 175

Cys Cys Ile Val Leu Gly Met Met Ser Ala Ala Ser Lys Pro Arg Leu
            180                 185                 190

Lys Gly Ile Leu Tyr Ala Val Gly Trp Ala Phe Gly Ala Trp Thr Tyr
            195                 200                 205

Trp Thr Ala Leu Gln Val Tyr Arg Asp Ala His Lys Ala Val Pro Lys
        210                 215                 220

Pro Leu Ala Trp Tyr Val Arg Ala Met Gly Tyr Val Phe Phe Thr Ser
225                 230                 235                 240

Trp Leu Thr Phe Pro Gly Trp Phe Leu Gly Pro Glu Gly Leu Glu
                245                 250                 255

Val Val Thr Gly Thr Val Ser Thr Leu Met His Ala Cys Ser Asp Leu
            260                 265                 270

Ile Ser Lys Asn Leu Trp Gly Phe Met Asp Trp His Leu Arg Val Leu
            275                 280                 285

Val Ala Arg His His Arg Lys Leu Phe Lys Ala Glu Glu His Ala
        290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile Asp Pro Ser Tyr Glu
                325                 330                 335

Leu Tyr Arg Leu Lys Arg Gln Asn His Pro Glu Tyr Phe Leu Ser Pro
            340                 345                 350

Ala Gln Thr Pro Arg Arg Gly Pro Ser Phe Asp Lys Arg Thr Ser Phe
            355                 360                 365

Glu Met Asp Gly Gly Lys Asn Gly Met Leu Gln Met Met Pro Val Thr
        370                 375                 380

Gly Met Gly Met Gly Met Gly Met Gly Gly Gly Lys Thr Val
385                 390                 395                 400

Leu Phe Leu Asp Tyr Thr Gly Gly Tyr Val Ser Phe Phe Glu Gln
                405                 410                 415

Gln Leu Ser Asn Met Gly Val Asn Val Thr Lys Cys Trp Ser Asp Asp
            420                 425                 430

Asp Met Tyr Asn Thr Ala Gly Val Ala Asn Val Lys Gln Leu Phe His
        435                 440                 445

Phe Ala Met Ile Pro Asn Asn Ala Leu Gly Gly Gln Met Val Met Asp
        450                 455                 460

Leu Arg Gly Thr Gly Leu Leu Val Val Ala Tyr Gly Pro Glu Pro Pro
465                 470                 475                 480

Met Pro Gly Met Gly Gln Asp Glu Phe Val Pro Leu Gln Met Pro Gly
                485                 490                 495

Val Pro Tyr Asp Glu Ser Ile Leu His Asn Leu Val Met Arg His Ala
            500                 505                 510
```

```
Ile Thr Gln Gly Leu Gly Met Asn Gly Met Gln Gly Asn Met Gly Gln
        515                 520                 525
Gln Gln Gln Met Met Gly Met Gln Gly Asn Met Asn Gly Met Gln Gly
        530                 535                 540
Asn Met Asn Gly Met Gln Gly Asn Met Asn Gly Met Gln Gly Asn Met
545                 550                 555                 560
Ser Gly Met Gln Gly Asn Met Asn Gly Met Gln Gly Asn Ser Gly Met
                565                 570                 575
Asn Gln Gly Trp Asn Asn Gln Gly Phe Thr Asn Thr Gly Ala Phe Gly
            580                 585                 590
Tyr

<210> SEQ ID NO 7
<211> LENGTH: 1540
<212> TYPE: DNA
<213> ORGANISM: Chloromonas augustae
<220> FEATURE:
<223> OTHER INFORMATION: channelopsin 1 (mRNA)

<400> SEQUENCE: 7
```

| | | | | |
|---|---|---|---|---|
| ccttgttcga gcctttgcgg gtccgtcgtg ttgggttcaa gatggacacc cttgcttggg | | | | 60 |
| tcgctcgtga gctcctcagc actgctcatg atgccactcc agccaccgcc accccctcga | | | | 120 |
| ctgatcacag cacaccttcg actgaccacg gcagcggcga gaccttcaac gtgacgatca | | | | 180 |
| ccattggcgg aggtcatcac ggaggacatg cgggaccggt cgacaactcc atcgtgattg | | | | 240 |
| gcggcattga tggctggata gctatccctg caggcgattg ctactgtgcc ggctggtacg | | | | 300 |
| tcagccatgg ctcgtcgttt gaggcgacct tcgcgcacgt ctgccagtgg agcattttcg | | | | 360 |
| ccgtttgtat cctgtccctg ctgtggtacg cgtggcaata ctggaaggct acgtgcggat | | | | 420 |
| gggaggaggt ttacgtctgc tgcatcgagc tggtgttcat ctgtttcgaa ctctaccacg | | | | 480 |
| agttcgactc gccctgctcg ctgtacctca gcaccgccaa catcgtcaac tggctgagat | | | | 540 |
| actcagaatg gcttctctgt tgtccggtca ttttgatcca tctgtccaac gtcacgggcc | | | | 600 |
| tttcagacga ctacggcagg cgcaccatgg gcctgctggt gtcggatatc gccaccattg | | | | 660 |
| tgtttggcat cacagcagcc atgctggtca gctggcccaa gatcatcttc tacctgctcg | | | | 720 |
| gtttcaccat gtgctgctac accttctacc tggccgcaaa ggtgctgatc gagtcgttcc | | | | 780 |
| accaggttcc caagggcatc tgccgccacc tggtcaaggc catggccatc acctactacg | | | | 840 |
| ttggctggag cttcttcccc ctcattttcc tgttcggcca gtcgggcttc aagaagatct | | | | 900 |
| cgccctacgc cgacgtgatt gcgtcgtcct tcggtgatct catctccaag aacatgttcg | | | | 960 |
| gactgctggg tcatttcctg cgcgtcaaga tccatgagca catcttgaag cacggtgaca | | | | 1020 |
| tccgcaagac cactcacctg cgcatcgcgg gcgaggagaa ggaggttgag acctttgtgg | | | | 1080 |
| aggaggagga cgaggacacg gtgaagcact cgaccaagga gctcgccaac cgcggctcgt | | | | 1140 |
| tcatcgtcat gcgcggcaac atgaaggcgc agggcatcga tgtgcgcgcg tctctggaca | | | | 1200 |
| tggaggagga tgaggagggc ggcatgggca aaggcaaggg caagggcgcg ggcgctgcca | | | | 1260 |
| gcctgatgcc aggacgcgtc atcctcgccg tcccagacat ttccatggtg gacttcttcc | | | | 1320 |
| acgaccactt cgctcacctg ggcgcctcca tcgagctggt gccggcgctg ggcgtggaga | | | | 1380 |
| acacgctgct gctggtgcag caggccatgc agctgggcgg cctcgacttt gtgctggtgc | | | | 1440 |
| acccagagtt cctgcgcgac cgttcacaga atggcttggt cagtcgcctg aagatgaccg | | | | 1500 |
| gccacggcgt gtgcgcgttc gggtgggtgc cctctggccc | | | | 1540 |

<210> SEQ ID NO 8
<211> LENGTH: 715
<212> TYPE: PRT
<213> ORGANISM: Chloromonas augustae
<220> FEATURE:
<223> OTHER INFORMATION: channelopsin 1

<400> SEQUENCE: 8

```
Met Asp Thr Leu Ala Trp Val Ala Arg Glu Leu Leu Ser Thr Ala His
1               5                   10                  15

Asp Ala Thr Pro Ala Thr Ala Thr Pro Ser Thr Asp His Ser Thr Pro
            20                  25                  30

Ser Thr Asp His Gly Ser Gly Thr Phe Asn Val Thr Ile Thr Ile
        35                  40                  45

Gly Gly Gly His His Gly Gly His Ala Gly Pro Val Asp Asn Ser Ile
    50                  55                  60

Val Ile Gly Gly Ile Asp Gly Trp Ile Ala Ile Pro Ala Gly Asp Cys
65              70                  75                  80

Tyr Cys Ala Gly Trp Tyr Val Ser His Gly Ser Ser Phe Glu Ala Thr
                85                  90                  95

Phe Ala His Val Cys Gln Trp Ser Ile Phe Ala Val Cys Ile Leu Ser
            100                 105                 110

Leu Leu Trp Tyr Ala Trp Gln Tyr Trp Lys Ala Thr Cys Gly Trp Glu
        115                 120                 125

Glu Val Tyr Val Cys Cys Ile Glu Leu Val Phe Ile Cys Phe Glu Leu
    130                 135                 140

Tyr His Glu Phe Asp Ser Pro Cys Ser Leu Tyr Leu Ser Thr Ala Asn
145                 150                 155                 160

Ile Val Asn Trp Leu Arg Tyr Ser Glu Trp Leu Leu Cys Cys Pro Val
                165                 170                 175

Ile Leu Ile His Leu Ser Asn Val Thr Gly Leu Ser Asp Asp Tyr Gly
            180                 185                 190

Arg Arg Thr Met Gly Leu Leu Val Ser Asp Ile Ala Thr Ile Val Phe
        195                 200                 205

Gly Ile Thr Ala Ala Met Leu Val Ser Trp Pro Lys Ile Ile Phe Tyr
    210                 215                 220

Leu Leu Gly Phe Thr Met Cys Cys Tyr Thr Phe Tyr Leu Ala Ala Lys
225                 230                 235                 240

Val Leu Ile Glu Ser Phe His Gln Val Pro Lys Gly Ile Cys Arg His
                245                 250                 255

Leu Val Lys Ala Met Ala Ile Thr Tyr Tyr Val Gly Trp Ser Phe Phe
            260                 265                 270

Pro Leu Ile Phe Leu Phe Gly Gln Ser Gly Phe Lys Lys Ile Ser Pro
        275                 280                 285

Tyr Ala Asp Val Ile Ala Ser Ser Phe Gly Asp Leu Ile Ser Lys Asn
    290                 295                 300

Met Phe Gly Leu Leu Gly His Phe Leu Arg Val Lys Ile His Glu His
305                 310                 315                 320

Ile Leu Lys His Gly Asp Ile Arg Lys Thr Thr His Leu Arg Ile Ala
                325                 330                 335

Gly Glu Glu Lys Glu Val Glu Thr Phe Val Glu Glu Asp Glu Asp
            340                 345                 350

Thr Val Lys His Ser Thr Lys Glu Leu Ala Asn Arg Gly Ser Phe Ile
        355                 360                 365
```

Val Met Arg Gly Asn Met Lys Ala Gln Gly Ile Asp Val Arg Ala Ser
370                 375                 380

Leu Asp Met Glu Glu Asp Glu Glu Gly Gly Met Gly Lys Gly Lys Gly
385                 390                 395                 400

Lys Gly Ala Gly Ala Ala Ser Leu Met Pro Gly Arg Val Ile Leu Ala
            405                 410                 415

Val Pro Asp Ile Ser Met Val Asp Phe Phe His Asp His Phe Ala His
            420                 425                 430

Leu Gly Ala Ser Ile Glu Leu Val Pro Ala Leu Gly Val Glu Asn Thr
            435                 440                 445

Leu Leu Leu Val Gln Gln Ala Met Gln Leu Gly Gly Leu Asp Phe Val
450                 455                 460

Leu Val His Pro Glu Phe Leu Arg Asp Arg Ser Gln Asn Gly Leu Val
465                 470                 475                 480

Ser Arg Leu Lys Met Thr Gly His Gly Val Cys Ala Phe Gly Trp Val
                485                 490                 495

Pro Ser Gly Pro Met Arg Glu Ile Ile Glu Ser Ala Gly Val Asp Gly
            500                 505                 510

Trp Leu Asp Gly Pro Ser Phe Gly Thr Gly Ile Asp Gln Glu Gln Leu
            515                 520                 525

Ile Glu Leu Ile Gly Tyr Met Gln Ala Lys Arg Lys Phe Ser Asn Arg
530                 535                 540

Phe Gly Gly Gly Gly Gly Gly Lys Pro Gly Phe Ala Ser Gly Gly
545                 550                 555                 560

Gly Phe Gly Gly Lys Ser Gly Leu Glu Leu Ala Pro Ser Met Ser Gln
                565                 570                 575

Gly Ser Gly Val Pro Leu Leu Gln Gln Gln Asn Ser Met Met Arg Ala
            580                 585                 590

Pro Pro Ser Pro Met Pro Asn Asn Gly Met Met Asn Pro Met Met Asn
            595                 600                 605

Pro Met Met Gly Ala Gly Gly Asn Ile Met Met Thr Asn Met Gly
610                 615                 620

Gly Met Asn Gln Ala Ala Asn Pro Leu Tyr Gly Ala Pro Pro Ser Pro
625                 630                 635                 640

Leu Ser Ser Gln Pro Gly Ala Gly Met Tyr Gly Ala Pro Gln Gln Pro
                645                 650                 655

Gln Met Gly Ser Gln Gly Ser Met Tyr Asn Ser Gly Ser Gln Leu Gln
            660                 665                 670

His Gln Gln Ser Met Gln Gln Gln Gln Ala Ala Pro Ala Pro Ala
            675                 680                 685

Ala Asp Gly Gly Ser Glu Ala Glu Met Leu Lys Gln Leu Met Ser Glu
690                 695                 700

Ile Asn Arg Leu Lys Ala Glu Leu Gly Glu Ser
705                 710                 715

<210> SEQ ID NO 9
<211> LENGTH: 2671
<212> TYPE: DNA
<213> ORGANISM: Chlamydomonas yellowstonensis
<220> FEATURE:
<223> OTHER INFORMATION: channelopsin 1 (mRNA)

<400> SEQUENCE: 9
ataacccaca cgcccactgc catcgtggca aagcgcgcct tgtagtccag atggacaccc     60
tcgcttgggt tgcccgagag ctgctcagct caggccacgg cactgacacc gccaccgact    120

```
caggccacgg cactgatact tctggtggcc atgactctag ccacgatgcg gtcgcccaca      180
atgtgacgct gctcatcgcc ccccacatg ctggggggcca tgccgggccg accgacacct     240
cgcagcaaat cacaggcatc gatggctgga tcgccatccc cgcgggcgac tgctattgcg     300
ccggctggta tgtcagccac ggcagctcgt tcgaggcgac gttcgcgcac gtctgccagt    360
ggagcatttt cgccgtctgc gtgctgtcgc tgctgtggta cgcgtaccag tactggaagg    420
cgacgtgcga tgggaggag gtctacgtct gctgcattga gttggtgttc atctgcttcg     480
agctctacca cgagttcgac tcgccctgct ccctgtacct cagcacctcc aacgtcgtca    540
actggctgcg ctattcagaa tggctcctct gttgtccggt cattttgatc catctgtcca    600
acgtcacggg cctgtccgac gactacggcc gccgcaccat gggcctgctg gtctcggata    660
tcgccaccat cgtgttcggc gtcacggccg ccatgctggt caactggcca agatcatct    720
tctacctcat cggcttcacg atgtgctgct acaccttctt cctcgccgca aaggtgctga   780
tcgagtcgtt ccaccaggtg cccaagggca tctgccgcca cctcgtcaag gccatggcca  840
tcacctactt cgtcggctgg agcttcttcc cgctcatctt cctgttcggc cagtcgggct   900
tcaagaagat ctcgccctac gccgacgtca ttgcgtcgtc attcggtgac ctcatctcca  960
agaacgcctt tggaatgctg ggtcattttcc tgcgtgtcaa gatccacgag cacattctga 1020
agcacggcga catccgcaag accactcacc tgcgcattgc cggcgaggag aaggaggttg  1080
agacgtttgt ggaggaggag gacgaggaca cggcgaagca ctcgaccaag gagctggcga  1140
accgcggctc gtttatcgtc atgcgtgaca agatgaagga gcagggcatc gacgtccgcg  1200
cctcgctcga catggacgaa gatgaggagg cccgcaccgg caagggcaag ggcgcgggcg  1260
cgaccagtct ggtgccgggc cgcgtcatcc tcgccgtccc cgacatctcc atggtcgact  1320
tcttccatga tcactttgcc cacctgggcg cgtccatcga gctggtgccg cgcgctgggcg  1380
ttgagaacac gctgctgctg gtgcagcagg cgatgcagct gggcggcctc gacttcgtcc   1440
tcgtgcaccc agagttcctg cgcgaccgct cacagaacgg cctcgtgagc cgcctgaaga   1500
tgacgggcca cggcgtgtgc gcctttgggt gggtgccctc gggcccgatg cgcgagatca   1560
ttgagtcggc cggcgtcgac ggctggctgg acggcccctc gttttggcacg ggcatcgacc  1620
aggagcagct gatcgagctc atcggctaca tgcaggccaa gcgcaagttc ggcatgcgtt   1680
ttggcggcgg cggcgccagc aaggccggct acagctccga cggcggcttt ggcggcaagg   1740
gcatgcttga gatgcagccg tcgatgtccc agggcagcgg cgtgccgctg ctgcagcaga   1800
acaacagcat gatgcgcgca ccaccctcgc ccatgggcaa catggcgaac aacggcatga   1860
tgaacccgat gatgtcgatg aacaacccga tgatgggcgg cggcgccgtc atgatgacga   1920
gcatggggtc gatgcagcag gccgccaacc cgctctacgg cgcaccgccg agcccgctga   1980
gcagccagcc gggcgccggc atgtacggcg cgcccgcgca gccccagatg ggcagccagg   2040
gcagcatgca cggcagcatg tacgcggca gccagcagca gcaccagcag ccgcagcagg    2100
cggccgcggc gcccgccgct gccgacggcg gctcggaggc tgagatgctg aagcagctca   2160
tgagcgagat caaccgcctg aaggccgagc tcggcgagag ctgattcatg cgtttgcatg   2220
cttgtggcgc tctctctttg attgctgagc tgctggtgtc aattgactgt cgaggcggcg   2280
agtgaggaga cagtgcgcag tgaccttctc ctgcaccca tccaccacac gttgtgctgc    2340
acggttgtgt ctttcatctc ccccggcacc atctttccca tgttctgtgg ccaccctcga   2400
tgtctgccag gattttggac tgtgtcatga cgtgcaattt tgcgtccatc tgtgaggcac   2460
```

-continued

```
gtctgccgct gtgtgtgatc tcaggcattg catgaggacg caaggagccg tgtctggcgt    2520
gatccgctgt gtgtggtgtg atcgactgca tgaggtgtga tccgtggttg tcaagcgcga    2580
tcagcggttg caggcaatat cgtcggcaga gtgttggtaa cagaaagcat tgaggttgtg    2640
tactgcacga tgtgaatgtc atgatctgca g                                   2671
```

<210> SEQ ID NO 10
<211> LENGTH: 717
<212> TYPE: PRT
<213> ORGANISM: Chlamydomonas yellowstonensis
<220> FEATURE:
<223> OTHER INFORMATION: channelopsin 1 (mRNA)

<400> SEQUENCE: 10

```
Met Asp Thr Leu Ala Trp Val Ala Arg Glu Leu Leu Ser Ser Gly His
  1               5                  10                  15

Gly Thr Asp Thr Ala Thr Asp Ser Gly His Gly Thr Asp Thr Ser Gly
                 20                  25                  30

Gly His Asp Ser Ser His Asp Ala Val Ala His Asn Val Thr Leu Leu
             35                  40                  45

Ile Ala Pro Pro His Ala Gly Gly His Ala Gly Pro Thr Asp Thr Ser
         50                  55                  60

Gln Gln Ile Thr Gly Ile Asp Gly Trp Ile Ala Ile Pro Ala Gly Asp
 65                  70                  75                  80

Cys Tyr Cys Ala Gly Trp Tyr Val Ser His Gly Ser Ser Phe Glu Ala
                 85                  90                  95

Thr Phe Ala His Val Cys Gln Trp Ser Ile Phe Ala Val Cys Val Leu
            100                 105                 110

Ser Leu Leu Trp Tyr Ala Tyr Gln Tyr Trp Lys Ala Thr Cys Gly Trp
        115                 120                 125

Glu Glu Val Tyr Val Cys Cys Ile Glu Leu Val Phe Ile Cys Phe Glu
130                 135                 140

Leu Tyr His Glu Phe Asp Ser Pro Cys Ser Leu Tyr Leu Ser Thr Ser
145                 150                 155                 160

Asn Val Val Asn Trp Leu Arg Tyr Ser Glu Trp Leu Leu Cys Cys Pro
                165                 170                 175

Val Ile Leu Ile His Leu Ser Asn Val Thr Gly Leu Ser Asp Asp Tyr
            180                 185                 190

Gly Arg Arg Thr Met Gly Leu Val Ser Asp Ile Ala Thr Ile Val
        195                 200                 205

Phe Gly Val Thr Ala Ala Met Leu Val Asn Trp Pro Lys Ile Ile Phe
    210                 215                 220

Tyr Leu Ile Gly Phe Thr Met Cys Cys Tyr Thr Phe Leu Ala Ala
225                 230                 235                 240

Lys Val Leu Ile Glu Ser Phe His Gln Val Pro Lys Gly Ile Cys Arg
                245                 250                 255

His Leu Val Lys Ala Met Ala Ile Thr Tyr Phe Val Gly Trp Ser Phe
            260                 265                 270

Phe Pro Leu Ile Phe Leu Phe Gly Gln Ser Gly Phe Lys Lys Ile Ser
        275                 280                 285

Pro Tyr Ala Asp Val Ile Ala Ser Ser Phe Gly Asp Leu Ile Ser Lys
    290                 295                 300

Asn Ala Phe Gly Met Leu Gly His Phe Leu Arg Val Lys Ile His Glu
305                 310                 315                 320

His Ile Leu Lys His Gly Asp Ile Arg Lys Thr Thr His Leu Arg Ile
```

```
                        325                 330                 335
Ala Gly Glu Glu Lys Glu Val Glu Thr Phe Val Glu Glu Asp Glu
                    340                 345                 350

Asp Thr Ala Lys His Ser Thr Lys Glu Leu Ala Asn Arg Gly Ser Phe
                355                 360                 365

Ile Val Met Arg Asp Lys Met Lys Glu Gln Gly Ile Asp Val Arg Ala
            370                 375                 380

Ser Leu Asp Met Asp Glu Asp Glu Glu Ala Arg Thr Gly Lys Gly Lys
385                 390                 395                 400

Gly Ala Gly Ala Thr Ser Leu Val Pro Gly Arg Val Ile Leu Ala Val
                405                 410                 415

Pro Asp Ile Ser Met Val Asp Phe Phe His Asp His Phe Ala His Leu
            420                 425                 430

Gly Ala Ser Ile Glu Leu Val Pro Ala Leu Gly Val Glu Asn Thr Leu
                435                 440                 445

Leu Leu Val Gln Gln Ala Met Gln Leu Gly Gly Leu Asp Phe Val Leu
450                 455                 460

Val His Pro Glu Phe Leu Arg Asp Arg Ser Gln Asn Gly Leu Val Ser
465                 470                 475                 480

Arg Leu Lys Met Thr Gly His Gly Val Cys Ala Phe Gly Trp Val Pro
                485                 490                 495

Ser Gly Pro Met Arg Glu Ile Ile Glu Ser Ala Gly Val Asp Gly Trp
                500                 505                 510

Leu Asp Gly Pro Ser Phe Gly Thr Gly Ile Asp Gln Glu Gln Leu Ile
            515                 520                 525

Glu Leu Ile Gly Tyr Met Gln Ala Lys Arg Lys Phe Gly Met Arg Phe
530                 535                 540

Gly Gly Gly Gly Ala Ser Lys Ala Gly Tyr Ser Ser Asp Gly Gly Phe
545                 550                 555                 560

Gly Gly Lys Gly Met Leu Glu Met Gln Pro Ser Met Ser Gln Gly Ser
                565                 570                 575

Gly Val Pro Leu Leu Gln Gln Asn Asn Ser Met Met Arg Ala Pro Pro
            580                 585                 590

Ser Pro Met Gly Asn Met Ala Asn Asn Gly Met Met Asn Pro Met Met
                595                 600                 605

Ser Met Asn Asn Pro Met Met Gly Gly Gly Ala Val Met Met Thr Ser
            610                 615                 620

Met Gly Ser Met Gln Gln Ala Ala Asn Pro Leu Tyr Gly Ala Pro Pro
625                 630                 635                 640

Ser Pro Leu Ser Ser Gln Pro Gly Ala Gly Met Tyr Gly Ala Pro Ala
                645                 650                 655

Gln Pro Gln Met Gly Ser Gln Ser Met His Gly Ser Met Tyr Gly
            660                 665                 670

Gly Ser Gln Gln Gln His Gln Gln Pro Gln Ala Ala Ala Pro
                675                 680                 685

Ala Ala Ala Asp Gly Gly Ser Glu Ala Glu Met Leu Lys Gln Leu Met
            690                 695                 700

Ser Glu Ile Asn Arg Leu Lys Ala Glu Leu Gly Glu Ser
705                 710                 715

<210> SEQ ID NO 11
<211> LENGTH: 1000
<212> TYPE: DNA
<213> ORGANISM: Chlamydomonas raudensis
```

<220> FEATURE:
<223> OTHER INFORMATION: channelopsin 2 (mRNA)

<400> SEQUENCE: 11

```
gctccctcgc atcgcgcgag ctgcaccagc gccgccaggc cgatggcttc catggcattc      60
tccgcgattt cgcttgcctc cagtgcaatg aggtccctgc aggccagtgg cggcaacccc     120
ttcgagcacg acgcgccgcc tgacaactcc tgcgagctca ctccttacgg ctgcctcaac     180
gacttctact gcaaccctgc ctacggcctg cagacgcag gtataacta ctgctacgtg       240
cagtccgcct acggcaagct ggccatcgtg cagacggacc agctgtcttg gctgtactcg     300
catggaagct ctggcgcgaa ggccgcctcc atcgccttcc agtggcttgc ctttgccacc     360
gccgtcatcg gcctcatgtt ctacgcgtgg gacacctgga gggcgactac cggatgggag     420
gaggtgtacg tatgtacgat cgagcttatc aaggtgctga ttgagatctt caaggagttc     480
gagttcccct tgctccctgta ccttccaacc ggcaactggg tgctgtggct gagatacgca     540
gagtggctgc tcacttgtcc cgtgattctg atccatctct ccaacattac cggcctcaag     600
gacgactaca acaagcgcac gatgcgactg ctggtgtctg atattggctg catcgtgtgg     660
ggcgtgacct cggccatgac cgccggttac ctcaagtgga tcttcttcgc catcggcttg     720
ttgtacggct ccaacaccta cttccactct gccaaggtgt acatcgaggc ctaccacacc     780
gtgcccaagg gcaggcgccg cgtcattgtg cgcctgatgg cctactgctt ctacctcgcc     840
tggaccatgt tccccatcct gtttgccctc ggtcctgagg catgggcca gatgtccgcc     900
tacatgtcga caatcctcac gacgattgcc gacgtgctgt cgaagcagat ctggggtctg     960
ctgggccacc acctgcgcgt gaagatttac cagcacatcc                          1000
```

<210> SEQ ID NO 12
<211> LENGTH: 635
<212> TYPE: PRT
<213> ORGANISM: Chlamydomonas raudensis
<220> FEATURE:
<223> OTHER INFORMATION: channelopsin 2

<400> SEQUENCE: 12

```
Met Ala Ser Met Ala Phe Ser Ala Ile Ser Leu Ala Ser Ser Ala Met
1               5                   10                  15

Arg Ser Leu Gln Ala Ser Gly Gly Asn Pro Phe Glu His Asp Ala Pro
            20                  25                  30

Pro Asp Asn Ser Cys Glu Leu Thr Pro Tyr Gly Cys Leu Asn Asp Phe
        35                  40                  45

Tyr Cys Asn Pro Ala Tyr Gly Leu Ala Asp Ala Gly Tyr Asn Tyr Cys
    50                  55                  60

Tyr Val Gln Ser Ala Tyr Gly Lys Leu Ala Ile Val Gln Thr Asp Gln
65                  70                  75                  80

Leu Ser Trp Leu Tyr Ser His Gly Ser Ser Gly Ala Lys Ala Ala Ser
                85                  90                  95

Ile Ala Phe Gln Trp Leu Ala Phe Ala Thr Ala Val Ile Gly Leu Met
            100                 105                 110

Phe Tyr Ala Trp Asp Thr Trp Arg Ala Thr Thr Gly Trp Glu Glu Val
        115                 120                 125

Tyr Val Cys Thr Ile Glu Leu Ile Lys Val Leu Ile Glu Ile Phe Lys
    130                 135                 140

Glu Phe Glu Phe Pro Cys Ser Leu Tyr Leu Pro Thr Gly Asn Trp Val
145                 150                 155                 160
```

-continued

```
Leu Trp Leu Arg Tyr Ala Glu Trp Leu Leu Thr Cys Pro Val Ile Leu
            165                 170                 175

Ile His Leu Ser Asn Ile Thr Gly Leu Lys Asp Asp Tyr Asn Lys Arg
            180                 185                 190

Thr Met Arg Leu Leu Val Ser Asp Ile Gly Cys Ile Val Trp Gly Val
            195                 200                 205

Thr Ser Ala Met Thr Ala Gly Tyr Leu Lys Trp Ile Phe Phe Ala Ile
            210                 215                 220

Gly Leu Leu Tyr Gly Ser Asn Thr Tyr Phe His Ser Ala Lys Val Tyr
225                 230                 235                 240

Ile Glu Ala Tyr His Thr Val Pro Lys Gly Arg Arg Val Ile Val
                245                 250                 255

Arg Leu Met Ala Tyr Cys Phe Tyr Leu Ala Trp Thr Met Phe Pro Ile
                260                 265                 270

Leu Phe Ala Leu Gly Pro Glu Gly Met Gly Gln Met Ser Ala Tyr Met
            275                 280                 285

Ser Thr Ile Leu Thr Thr Ile Ala Asp Val Leu Ser Lys Gln Ile Trp
            290                 295                 300

Gly Leu Leu Gly His His Leu Arg Val Lys Ile Tyr Gln His Ile Leu
305                 310                 315                 320

Ile His Gly Asp Ile Arg Lys Lys Thr Thr Met Gln Val Gly Gly Glu
                325                 330                 335

Asp Val Glu Val Glu Glu Phe Val Asp Glu Asp Glu Glu Gly Val
            340                 345                 350

Arg Gln Ala Asn Thr Gln Leu Ala Asn Arg Glu Ser Phe Val His Met
            355                 360                 365

Ala Glu Gln Met Lys Lys Asn Gly Ile Glu Val Arg Ala Thr Tyr Asp
            370                 375                 380

Thr Gly Val Asp Lys Glu Met Gly His His His Val Glu Ala Gly Arg
385                 390                 395                 400

Ile Ile Leu Ala Val Pro Asp Met Ser Met Val Asp Phe Phe Arg Gln
                405                 410                 415

Gln Leu Ser Gln Met Pro Ala Pro Ile Glu Leu Val Pro Ala Leu Gly
            420                 425                 430

Ile Asp Asn Thr Val Gln Leu Val Gln Gln Ala Ala Ala Leu Gly Gly
            435                 440                 445

Cys Asp Phe Val Leu Val His Pro Glu Phe Leu Lys Asp Ala Ser Ser
450                 455                 460

Ser Gly Leu Val Thr Lys Leu Arg Met Met Gly Gln Arg Val Cys Ala
465                 470                 475                 480

Phe Gly Trp Ser Pro Met Gly Pro Gln Arg Glu Leu Ile Glu Ser Arg
                485                 490                 495

Gly Leu Asp Gly Trp Leu Glu Gly Pro Ser Phe Gly Ser Gly Ile Asp
            500                 505                 510

Arg His Gln Leu Thr Ala Leu Val Ser Arg Met Gln Met Met Arg Lys
            515                 520                 525

Ala Thr Met Gly Ser Gly Met Ala Asn Pro Met Ala Gln Gln Gln Gln
            530                 535                 540

Ser Phe Met Met His Gln Gln Asn Ser Ala His Asn Ser Phe Met Ile
545                 550                 555                 560

Gln Pro Gln Thr Gln Pro Gln Ala Asn Pro Leu Tyr Gly Ala Gln Met
                565                 570                 575

Gly Ser Gln Met Gly Ala Thr Thr Gly Ser Ala Leu Phe His Pro Ala
```

```
                      580                 585                 590
Ala Pro Gly Asn Ala Thr Pro Pro Ser Pro Ser Gly Ala Ala Asn Val
            595                 600                 605

Asn Glu Ala Glu Met Leu Gln Gln Leu Met Gly Glu Ile Thr Arg Leu
            610                 615                 620

Lys Ser Glu Leu Gly Gly Ser Gly Thr Pro Arg
625                 630                 635

<210> SEQ ID NO 13
<211> LENGTH: 20
<212> TYPE: DNA
<213> ORGANISM: Artificial Sequence
<220> FEATURE:
<223> OTHER INFORMATION: Forward primer for C. augustae, C.
      yellowstonen, C. raudensis
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u

<400> SEQUENCE: 13
tgcggntggg aggagrtnta                                              20

<210> SEQ ID NO 14
<211> LENGTH: 18
<212> TYPE: DNA
<213> ORGANISM: Artificial Sequence
<220> FEATURE:
<223> OTHER INFORMATION: reverse primer for C. augustae and C.
      yellowstonensis

<400> SEQUENCE: 14
agratrtgct crtgratc                                                18

<210> SEQ ID NO 15
<211> LENGTH: 18
<212> TYPE: DNA
<213> ORGANISM: Artificial sequence
<220> FEATURE:
<223> OTHER INFORMATION: reverse primer for C. raudensis
<220> FEATURE:
<221> NAME/KEY: misc_feature
<222> LOCATION: (10)..(10)
<223> OTHER INFORMATION: n is a, c, g, or t

<400> SEQUENCE: 15
rcccttsggn acsgtrtg                                                18

<210> SEQ ID NO 16
<211> LENGTH: 66
<212> TYPE: PRT
<213> ORGANISM: M.viride
<220> FEATURE:
<223> OTHER INFORMATION: Channelrhodopsin1 (MChR1)

<400> SEQUENCE: 16

Thr Cys Gly Trp Glu Val Trp Phe Val Ala Cys Ile Glu Thr Ser Ile
1               5                   10                  15

Tyr Ile Ile Ala Ile Thr Ser Glu Ala Asp Ser Pro Phe Thr Leu Tyr
            20                  25                  30

Leu Thr Asn Gly Gln Ile Ser Pro Gln Leu Arg Tyr Met Glu Trp Leu
        35                  40                  45
```

```
Met Thr Cys Pro Val Ile Leu Ile Ala Leu Ser Asn Ile Thr Gly Met
    50                  55                  60

Ala Glu
65

<210> SEQ ID NO 17
<211> LENGTH: 66
<212> TYPE: PRT
<213> ORGANISM: C.reinhardtii
<220> FEATURE:
<223> OTHER INFORMATION: Channelrhodopsin 1 (ChR1)

<400> SEQUENCE: 17

Thr Cys Gly Trp Glu Glu Ile Tyr Val Ala Thr Ile Glu Met Ile Lys
1               5                   10                  15

Phe Ile Ile Glu Tyr Phe His Glu Phe Asp Pro Ala Val Ile Tyr
            20                  25                  30

Ser Ser Asn Gly Asn Lys Thr Val Trp Leu Arg Tyr Ala Glu Trp Leu
            35                  40                  45

Leu Thr Cys Pro Val Ile Leu Ile His Leu Ser Asn Leu Thr Gly Leu
    50                  55                  60

Ala Asn
65

<210> SEQ ID NO 18
<211> LENGTH: 66
<212> TYPE: PRT
<213> ORGANISM: C.reinhardtii
<220> FEATURE:
<223> OTHER INFORMATION: Channelrhodopsin 2 (ChR2)

<400> SEQUENCE: 18

Thr Cys Gly Trp Glu Glu Ile Tyr Val Cys Ala Ile Glu Met Val Lys
1               5                   10                  15

Val Ile Leu Glu Phe Phe Phe Glu Phe Lys Asn Pro Ser Met Leu Tyr
            20                  25                  30

Leu Ala Thr Gly His Arg Val Gln Trp Leu Arg Tyr Ala Glu Trp Leu
            35                  40                  45

Leu Thr Cys Pro Val Ile Leu Ile His Leu Ser Asn Leu Thr Gly Leu
    50                  55                  60

Ser Asn
65

<210> SEQ ID NO 19
<211> LENGTH: 66
<212> TYPE: PRT
<213> ORGANISM: V.carteri
<220> FEATURE:
<223> OTHER INFORMATION: Channelrhodopsin 1 (VChR1)

<400> SEQUENCE: 19

Thr Cys Gly Trp Glu Glu Val Tyr Val Ala Leu Ile Glu Met Met Lys
1               5                   10                  15

Ser Ile Ile Glu Ala Phe His Glu Phe Asp Ser Pro Ala Thr Leu Trp
            20                  25                  30

Leu Ser Ser Gly Asn Gly Val Val Trp Met Arg Tyr Gly Glu Trp Leu
            35                  40                  45

Leu Thr Cys Pro Val Leu Leu Ile His Leu Ser Asn Leu Thr Gly Leu
    50                  55                  60
```

Lys Asp
65

<210> SEQ ID NO 20
<211> LENGTH: 66
<212> TYPE: PRT
<213> ORGANISM: V.carteri
<220> FEATURE:
<223> OTHER INFORMATION: Channelrhodopsin 2 (VChR2)

<400> SEQUENCE: 20

Thr Cys Gly Trp Glu Glu Val Tyr Val Cys Cys Val Glu Leu Thr Lys
1               5                   10                  15

Val Val Ile Glu Phe Phe His Glu Phe Asp Glu Pro Gly Met Leu Tyr
            20                  25                  30

Leu Ala Asn Gly Asn Arg Val Leu Trp Leu Arg Tyr Gly Glu Trp Leu
        35                  40                  45

Leu Thr Cys Pro Val Ile Leu Ile His Leu Ser Asn Leu Thr Gly Leu
    50                  55                  60

Lys Asp
65

<210> SEQ ID NO 21
<211> LENGTH: 288
<212> TYPE: PRT
<213> ORGANISM: C.augustae
<220> FEATURE:
<223> OTHER INFORMATION: Channelrhodopsin 1 (CaChR1)

<400> SEQUENCE: 21

Phe Asn Val Thr Ile Thr Ile Gly Gly Gly His His Gly Gly His Ala
1               5                   10                  15

Gly Pro Val Asp Asn Ser Ile Val Ile Gly Gly Ile Asp Gly Trp Ile
            20                  25                  30

Ala Ile Pro Ala Gly Asp Cys Tyr Cys Ala Gly Trp Tyr Val Ser His
        35                  40                  45

Gly Ser Ser Phe Glu Ala Thr Phe Ala His Val Cys Gln Trp Ser Ile
    50                  55                  60

Phe Ala Val Cys Ile Leu Ser Leu Leu Trp Tyr Ala Trp Gln Tyr Trp
65                  70                  75                  80

Lys Ala Thr Cys Gly Trp Glu Glu Val Tyr Val Cys Cys Ile Glu Leu
                85                  90                  95

Val Phe Ile Cys Phe Glu Leu Tyr His Glu Phe Asp Ser Pro Cys Ser
            100                 105                 110

Leu Tyr Leu Ser Thr Ala Asn Ile Val Asn Trp Leu Arg Tyr Ser Glu
        115                 120                 125

Trp Leu Leu Cys Cys Pro Val Ile Leu Ile His Leu Ser Asn Val Thr
    130                 135                 140

Gly Leu Ser Asp Asp Tyr Gly Arg Arg Thr Met Gly Leu Leu Val Ser
145                 150                 155                 160

Asp Ile Ala Thr Ile Val Phe Gly Ile Thr Ala Ala Met Leu Val Ser
                165                 170                 175

Trp Pro Lys Ile Ile Phe Tyr Leu Leu Gly Phe Thr Met Cys Cys Tyr
            180                 185                 190

Thr Phe Tyr Leu Ala Ala Lys Val Leu Ile Glu Ser Phe His Gln Val
        195                 200                 205

Pro Lys Gly Ile Cys Arg His Leu Val Lys Ala Met Ala Ile Thr Tyr
    210                 215                 220

```
Tyr Val Gly Trp Ser Phe Phe Pro Leu Ile Phe Leu Phe Gly Gln Ser
225                 230                 235                 240

Gly Phe Lys Lys Ile Ser Pro Tyr Ala Asp Val Ile Ala Ser Ser Phe
                245                 250                 255

Gly Asp Leu Ile Ser Lys Asn Ala Asn Arg Gly Ser Phe Ile Val Met
                260                 265                 270

Arg Gly Asn Met Lys Ala Gln Gly Ile Asp Val Arg Ala Ser Leu Asp
        275                 280                 285
```

<210> SEQ ID NO 22
<211> LENGTH: 288
<212> TYPE: PRT
<213> ORGANISM: C. yellowstonensis
<220> FEATURE:
<223> OTHER INFORMATION: Channelrhodopsin 1 (CyChR1)

<400> SEQUENCE: 22

```
His Asn Val Thr Leu Leu Ile Ala Pro Pro His Ala Gly Gly His Ala
1               5                   10                  15

Gly Pro Thr Asp Thr Ser Gln Gln Ile Thr Gly Ile Asp Gly Trp Ile
                20                  25                  30

Ala Ile Pro Ala Gly Asp Cys Tyr Cys Ala Gly Trp Tyr Val Ser His
            35                  40                  45

Gly Ser Ser Phe Glu Ala Thr Phe Ala His Val Cys Gln Trp Ser Ile
        50                  55                  60

Phe Ala Val Cys Val Leu Ser Leu Leu Trp Tyr Ala Tyr Gln Tyr Trp
65                  70                  75                  80

Lys Ala Thr Cys Gly Trp Glu Glu Val Tyr Val Cys Cys Ile Glu Leu
                85                  90                  95

Val Phe Ile Cys Phe Glu Leu Tyr His Glu Phe Asp Ser Pro Cys Ser
                100                 105                 110

Leu Tyr Leu Ser Thr Ser Asn Val Val Asn Trp Leu Arg Tyr Ser Glu
            115                 120                 125

Trp Leu Leu Cys Cys Pro Val Ile Leu Ile His Leu Ser Asn Val Thr
130                 135                 140

Gly Leu Ser Asp Asp Tyr Gly Arg Arg Thr Met Gly Leu Leu Val Ser
145                 150                 155                 160

Asp Ile Ala Thr Ile Val Phe Gly Val Thr Ala Ala Met Leu Val Asn
                165                 170                 175

Trp Pro Lys Ile Ile Phe Tyr Leu Ile Gly Phe Thr Met Cys Cys Tyr
            180                 185                 190

Thr Phe Phe Leu Ala Ala Lys Val Leu Ile Glu Ser Phe His Gln Val
        195                 200                 205

Pro Lys Gly Ile Cys Arg His Leu Val Lys Ala Met Ala Ile Thr Tyr
    210                 215                 220

Phe Val Gly Trp Ser Phe Phe Pro Leu Ile Phe Leu Phe Gly Gln Ser
225                 230                 235                 240

Gly Phe Lys Lys Ile Ser Pro Tyr Ala Asp Val Ile Ala Ser Ser Phe
                245                 250                 255

Gly Asp Leu Ile Ser Lys Asn Ala Asn Arg Gly Ser Phe Ile Val Met
                260                 265                 270

Arg Asp Lys Met Lys Glu Gln Gly Ile Asp Val Arg Ala Ser Leu Asp
        275                 280                 285
```

<210> SEQ ID NO 23

<211> LENGTH: 285
<212> TYPE: PRT
<213> ORGANISM: C.reinhardtii
<220> FEATURE:
<223> OTHER INFORMATION: Channelrhodopsin 1 (ChR1)

<400> SEQUENCE: 23

```
Val Ala Thr Gln Asp Gly Asp Val Tyr Phe His Arg Ala His Glu Arg
1               5                   10                  15

Met Leu Phe Gln Thr Ser Tyr Thr Leu Glu Asn Asn Gly Ser Val Ile
            20                  25                  30

Cys Ile Pro Asn Asn Gly Gln Cys Phe Cys Leu Ala Trp Leu Lys Asn
        35                  40                  45

Gly Thr Asn Ala Glu Lys Leu Ala Ala Asn Ile Leu Gln Trp Ile Thr
    50                  55                  60

Phe Ala Leu Ser Ala Leu Cys Leu Met Phe Tyr Gly Tyr Gln Thr Trp
65                  70                  75                  80

Lys Ser Thr Cys Gly Trp Glu Glu Ile Tyr Val Ala Thr Glu Met Ile
                85                  90                  95

Lys Phe Ile Ile Glu Tyr Phe His Glu Phe Asp Glu Pro Ala Val Ile
            100                 105                 110

Tyr Ser Ser Asn Gly Asn Lys Thr Val Trp Leu Arg Tyr Ala Glu Trp
        115                 120                 125

Leu Leu Thr Cys Pro Val Ile Leu Ile His Leu Ser Asn Leu Thr Gly
    130                 135                 140

Leu Ala Asn Asp Tyr Asn Lys Arg Thr Met Gly Leu Leu Val Ser Asp
145                 150                 155                 160

Ile Gly Thr Ile Val Trp Gly Thr Ala Ala Leu Ser Lys Gly Tyr Val
                165                 170                 175

Arg Val Ile Phe Phe Leu Met Gly Leu Cys Tyr Gly Ile Tyr Thr Phe
            180                 185                 190

Asn Ala Ala Lys Val Tyr Ile Glu Ala Tyr His Thr Val Pro Lys Gly
        195                 200                 205

Ile Cys Arg Asp Leu Val Arg Tyr Leu Ala Trp Leu Tyr Phe Cys Ser
    210                 215                 220

Trp Ala Met Phe Pro Val Leu Phe Leu Leu Gly Pro Glu Gly Phe Gly
225                 230                 235                 240

His Ile Asn Gln Phe Asn Ser Ala Ile Ala His Ala Ile Leu Asp Leu
                245                 250                 255

Ala Ser Lys Asn Ala Asn Arg Asp Ser Phe Ile Ile Met Arg Asp Arg
            260                 265                 270

Leu Lys Glu Lys Gly Phe Glu Thr Arg Ala Ser Leu Asp
        275                 280                 285
```

<210> SEQ ID NO 24
<211> LENGTH: 289
<212> TYPE: PRT
<213> ORGANISM: C.raudensis
<220> FEATURE:
<223> OTHER INFORMATION: Channelrhodopsin 2 (CrChR2)

<400> SEQUENCE: 24

```
Leu Thr Pro Tyr Gly Cys Leu Asn Asp Phe Tyr Cys Asn Pro Ala Tyr
1               5                   10                  15

Gly Leu Ala Asp Ala Gly Tyr Asn Tyr Cys Tyr Val Gln Ser Ala Tyr
            20                  25                  30

Gly Lys Leu Ala Ile Val Gln Thr Asp Gln Leu Ser Trp Leu Tyr Ser
```

His Gly Ser Ser Gly Ala Lys Ala Ser Ile Ala Phe Gln Trp Leu
                50                  55                  60

Ala Phe Ala Thr Ala Val Ile Gly Leu Met Phe Tyr Ala Trp Asp Thr
 65                  70                  75                  80

Trp Lys Ala Thr Thr Gly Trp Glu Glu Val Tyr Val Cys Thr Ile Glu
                 85                  90                  95

Leu Ile Lys Val Leu Ile Glu Ile Phe Lys Glu Phe Glu Ile Pro Cys
                100                 105                 110

Ser Leu Tyr Leu Pro Thr Gly Asn Trp Val Leu Trp Leu Arg Tyr Ala
                115                 120                 125

Glu Trp Leu Leu Thr Cys Pro Val Ile Leu Ile His Leu Ser Asn Ile
    130                 135                 140

Thr Gly Leu Lys Asp Asp Tyr Asn Lys Arg Thr Met Arg Leu Leu Val
145                 150                 155                 160

Ser Asp Ile Gly Cys Ile Val Trp Gly Val Thr Ser Ala Met Thr Val
                165                 170                 175

Gly Tyr Leu Lys Trp Ile Phe Phe Ala Ile Gly Leu Leu Tyr Gly Ser
                180                 185                 190

Asn Thr Tyr Phe His Ser Ala Lys Val Tyr Ile Glu Ala Tyr His Thr
                195                 200                 205

Val Pro Lys Gly Arg Cys Arg Val Ile Val Arg Leu Met Ala Tyr Cys
    210                 215                 220

Phe Tyr Leu Ala Trp Thr Met Phe Pro Ile Leu Phe Ala Leu Gly Pro
225                 230                 235                 240

Glu Gly Met Gly Gln Met Ser Ala Tyr Met Ser Thr Ile Leu Thr Thr
                245                 250                 255

Ile Ala Asp Val Leu Ser Lys Gln Ala Asn Arg Glu Ser Phe Val His
                260                 265                 270

Met Ala Glu Gln Met Lys Lys Asn Gly Ile Glu Val Arg Ala Thr Tyr
    275                 280                 285

Asp

<210> SEQ ID NO 25
<211> LENGTH: 283
<212> TYPE: PRT
<213> ORGANISM: C.reinhardtii
<220> FEATURE:
<223> OTHER INFORMATION: Channelrhodopsin 2 (ChR2)

<400> SEQUENCE: 25

Met Asp Tyr Gly Gly Ala Leu Ser Ala Val Gly Arg Glu Leu Leu Phe
 1               5                  10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110

```
Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Ala Ser Arg Glu Ser Phe Leu Val Met Arg Asp Lys Met Lys
                260                 265                 270

Glu Lys Gly Ile Asp Val Arg Ala Ser Leu Asp
        275                 280

<210> SEQ ID NO 26
<211> LENGTH: 217
<212> TYPE: PRT
<213> ORGANISM: Halobacter
<220> FEATURE:
<223> OTHER INFORMATION: Bacteriarhodopsin 1 (BR)

<400> SEQUENCE: 26

Gln Ala Gln Ile Thr Gly Arg Pro Glu Trp Ile Trp Leu Ala Leu Gly
1               5                   10                  15

Thr Ala Leu Met Gly Leu Gly Thr Leu Tyr Phe Leu Val Lys Gly Met
                20                  25                  30

Gly Val Ser Asp Pro Asp Ala Lys Lys Phe Tyr Ala Ile Thr Thr Leu
            35                  40                  45

Val Pro Ala Ile Ala Phe Thr Met Tyr Leu Ser Met Leu Leu Gly Tyr
        50                  55                  60

Gly Leu Thr Met Val Pro Phe Gly Gly Glu Gln Asn Pro Ile Tyr Trp
65                  70                  75                  80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
                100                 105                 110

Gly Ala Asp Gly Ile Met Ile Gly Thr Gly Leu Val Gly Ala Leu Thr
            115                 120                 125

Lys Val Tyr Ser Tyr Arg Phe Val Trp Trp Ala Ile Ser Thr Ala Ala
        130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
                180                 185                 190
```

```
Ser Glu Gly Ala Gly Ile Val Pro Leu Asn Ile Glu Thr Leu Leu Phe
        195                 200                 205
Met Val Leu Asp Val Ser Ala Lys Val
    210                 215
```

CDNA-DERIVED NUCLEIC ACIDS ENCODING RED-SHIFTED CHANNELRHODOPSINS

CROSS-REFERENCE TO RELATED APPLICATIONS

This present application is a continuation of U.S. patent application Ser. No. 14/053,129 filed Oct. 14, 2013 (now U.S. Pat. No. 9,102,747, issued Aug. 11, 2015), and is a continuation of U.S. patent application Ser. No. 13/420,352 (now U.S. Pat. No. 8,580,937, issued Nov. 12, 2013) which claims the benefit of U.S. Provisional Application Ser. No. 61/452,513 filed Mar. 14, 2011, each of which are herein incorporated by reference in their entireties for all purposes.

STATEMENT REGARDING FEDERALLY SPONSORED RESEARCH OR DEVELOPMENT

This invention was made with U.S. Government support under Grant Nos. RC1AG035779 and R37GM027750 awarded by the National Institutes of Health. The government has certain rights in the invention.

TECHNICAL FIELD

This disclosure generally relates to methods and compositions that utilize channelrhodopsins derived from algae, and more particularly to such channelrhodopsins having red-shifted improved characteristics for optogenetic applications or for use as therapeutic agents.

BACKGROUND

Optogenetics (reviewed by Deisseroth. *Nat Methods* 8 (1): 26-9, 2011), refers to a rapidly adapted approach of using new high-speed optical methods for probing and controlling genetically targeted neurons within intact neural circuits. Optogenetics involves the introduction of light-activated channels and enzymes that allow manipulation of neural activity with millisecond precision while maintaining cell-type resolution through the use of specific targeting mechanisms. Because the brain is a high-speed system, millisecond-scale temporal precision is central to the concept of optogenetics, which allows probing the causal role of specific action potential patterns in defined cells.

As traditional genetics has made use of "loss-of-function" or "gain of function" changes that result to determine the role and expression pattern of a particular protein. Similarly, optogenetics by definition will allow addition or deletion of precise activity patterns within specific cells in the brains of intact animals, including mammals in order to probe the role of a particular neural function. By achieving photonic control of neuronal firing control the action potential patterns involved in mammalian behavior can be determined and manipulated.

Light control of motility behavior (phototaxis and photophobic responses) in green flagellate algae is mediated by sensory rhodopsins homologous to phototaxis receptors and light-driven ion transporters in prokaryotic organisms. In the phototaxis process, excitation of the algal sensory rhodopsins leads to generation of transmembrane photoreceptor currents. When expressed in animal cells, the algal phototaxis receptors function as light-gated cation channels, which has earned them the name "channelrhodopsins." Channelrhodopsins have become useful molecular tools for light control of cellular activity.

Originally, the source of these light-activated channels and enzymes were several microbial opsins, including, Channelrhodopsin-2 (ChR2) a single-component light-activated cation channel from algae, which allowed millisecond-scale temporal control in mammals, required only one gene to be expressed in order to work, and responded to visible-spectrum light with a chromophore (retinal) that was already present and supplied to ChR2 by the mammalian brain tissue. The experimental utility of ChR2 was quickly proven in a variety of animal models ranging from behaving mammals to classical model organisms such as flies, worms, and zebrafish, and hundreds of groups have employed ChR2 and related microbial proteins to study neural circuits.

Four channelrhodopsins have been identified to date, ChR1 and ChR2 from *Chlamydomonas reinhardtii* (Sineshchekov, O. A., K.-H. Jung, and J. L. Spudich. Two rhodopsins mediate phototaxis to low- and high-intensity light in *Chlamydomonas reinhardtii*. *Proc. Natl. Acad. Sci. USA*. 99:8689-869, 2002.; Nagel, G., D. Ollig, M. Fuhrmann, S. Kateriya, A. M. Musti, E. Bamberg, and P. Hegemann. Channelrhodopsin-1: a light-gated proton channel in green algae. *Science*. 296:2395-2398, 2002; Nagel, G., T. Szellas, W. Huhn, S. Kateriya, N. Adeishvili, P. Berthold, D. Ollig, P. Hegemann, and E. Bamberg. Channelrhodopsin-2, a directly light-gated cation-selective membrane channel. *Proc. Natl. Acad. Sci. USA*. 100:13940-13945, 2003; Suzuki, T., K. Yamasaki, S. Fujita, K. Oda, M. Iseki, K. Yoshida, M. Watanabe, H. Daiyasu, H. Toh, E. Asamizu, S. Tabata, K. Miura, H. Fukuzawa, S. Nakamura, and T. Takahashi. Archaeal-type rhodopsins in *Chlamydomonas*: model structure and intracellular localization. *Biochem. Biophys. Res. Commun*. 301:711-717, 2003), and VChR1 and VChR2 from *Volvox carteri* (Zhang, F., M. Prigge, F. Beyriere, S. P. Tsunoda, J. Mattis, O. Yizhar, P. Hegemann, and K. Deisseroth. Red-shifted optogenetic excitation: a tool for fast neural control derived from *Volvox carteri*. *Nat. Neurosci*. 11:631-633, 2008; Kianianmomeni, A., K. Stehfest, G. Nematollahi, P. Hegemann, and A. Hallmann. Channelrhodopsins of *Volvox carteri* are photochromic proteins that are specifically expressed in somatic cells under control of light, temperature, and the sex inducer. *Plant. Physiol*. 151:347-366, 2009). They contain a 7-transmembrane-helix (7TM) domain characteristic of type 1 rhodopsins (Spudich, J. L., C.-S. Yang, K.-H. Jung, and E. N. Spudich. Retinylidene proteins: structures and functions from archaea to humans. *Annu. Rev. Cell Dev. Biol*. 16:365-392, 2000) followed by a conserved but more variable extended C-terminal region. The property of light-gated ion permeability exhibited by their 7TM domains, makes channelrhodopsins valuable tools for light-induced depolarization of cell membranes. When transfected into and expressed in excitable cells, e.g. defined subpopulations of rodent brain neurons, channelrhodopsins enable targeted light-activation of neuron firing in tissue culture and in living organisms (Boyden, E. S., F. Zhang, E. Bamberg, G. Nagel, and K. Deisseroth. Millisecond-time scale, genetically targeted optical control of neural activity. *Nat. Neurosci*. 8:1263-1268, 2005; Li, X., D. V. Gutierrez, M. G. Hanson, J. Han, M. D. Mark, H. Chiel, P. Hegemann, L. T. Landmesser, and S. Herlitze. Fast noninvasive activation and inhibition of neural and network activity by vertebrate rhodopsin and green algae channelrhodopsin. *Proc. Natl. Acad. Sci. USA*. 102:17816-17821, 2005; Nagel, G., M. Brauner, J. F. Liewald, N. Adeishvili, E. Bamberg, and A. Gottschalk. Light activation of channelrhodopsin-2 in excitable cells of *Caenorhabditis elegans* triggers rapid behavioral responses. *Curr. Biol*. 15:2279-2284, 2005). This optogenetic approach, offers temporal and spatial resolution superior to that of conventional electrical or chemical stimulation. Today, channelrhodopsins are widely used in both neuronal and non-neuronal systems, such as glial, muscle and embryonic stem cells as a tool for controlled plasma membrane depolarization (reviewed by Deisseroth, 2011, ibid).

Several intrinsic properties of the four known channelrhodopsins limit their application as optogenetic tools (reviewed in Lin, J. Y. A user's guide to channelrhodopsin variants: features, limitations and future developments. *Exp. Physiol.* 96:19-25, 2010; Hegemann, P., and A. Moglich. Channelrhodopsin engineering and exploration of new optogenetic tools. *Nat. Methods.* 8:39-42, 2011). The most widely used ChR2 has maximal spectral sensitivity at 470 nm but excitation at longer wavelengths is preferable to minimize light scattering by biological tissues. VChR1 is a red-shifted channelrhodopsin variant, but it has slower current kinetics compromising the fidelity of neuronal spiking at moderate to high stimulation frequencies. Another limiting property is that photocurrents generated by all channelrhodopsins in response to a pulse of continuous light decrease to a plateau level, a process called "inactivation." In the most commonly used ChR2 this decrease can be as large as 80% from the peak amplitude, which correspondingly decreases the light-induced membrane depolarization, requiring more intense or longer light pulses to trigger neuronal action potentials or induce other biological action. This limitation is further aggravated by low unitary conductance of channelrhodopsins, which is less than that of common ion channels, as estimated by the whole-cell current noise analysis (Feldbauer, K., D. Zimmermann, V. Pintschovius, J. Spitz, C. Bamann, and E. Bamberg. Channelrhodopsin-2 is a leaky proton pump. *Proc. Natl. Acad. Sci. USA.* 106:12317-12322, 2009; Lin, J. Y., M. Z. Lin, P. Steinbach, and R. Y. Tsien. Characterization of engineered channelrhodopsin variants with improved properties and kinetics. *Biophys. J.* 96:1803-1814, 2009).

SUMMARY

The presently disclosed methods and compositions are based, in part, on the discovery and identification of certain novel channelrhodopsins, several of which are red-shifted, derived from algae that when cloned and expressed by mammalian cells were active for light-activation of neuron firing. The use of these channelrhodopsins would improve optogenetic techniques and applications and they can be used to aid in diagnosis, prevention, and/or treatment of neuronal or neurologic disorders, such as but not limited to Parkinson's disease, as well as for ocular disorders. Also described are methods and compositions of red-shifting the absorbance maxima of channelrhodopsins.

Figure 24:
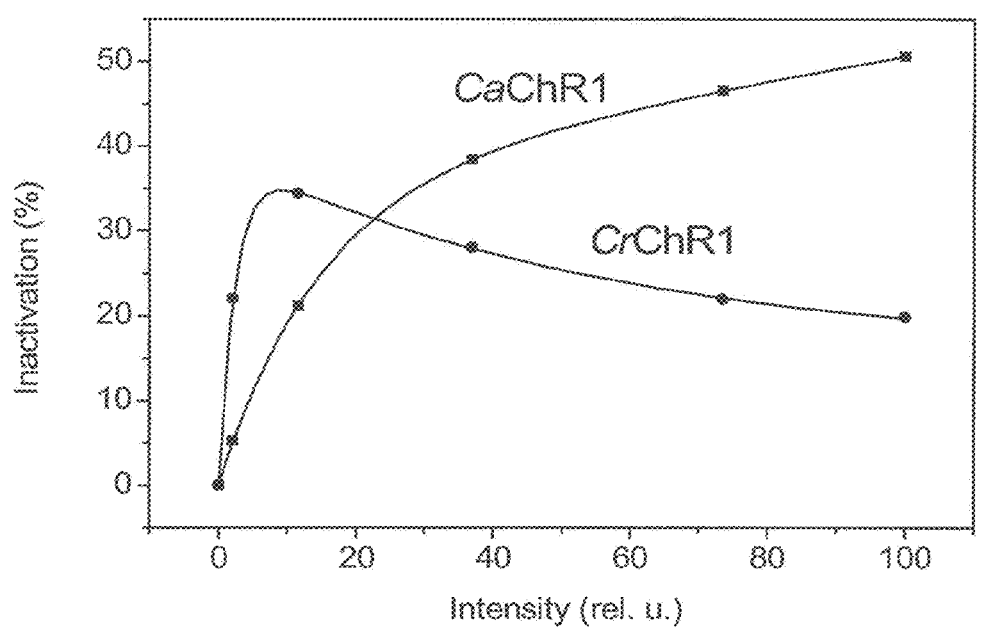
FIG. 24 illustrates the dependence of light inactivation (calculated as the difference between the peak and plateau amplitudes shown in FIGS. 21 and 22, relative to the peak amplitude) on the stimulus intensity for currents generated by CaChR1 from *C. augustae* (squares) and CrChR1 from *C. raudensis* (circles).

Excitation light was as in FIG. 24. Experimental data (dots) were fitted with two exponential functions (solid lines).

Figure 29:
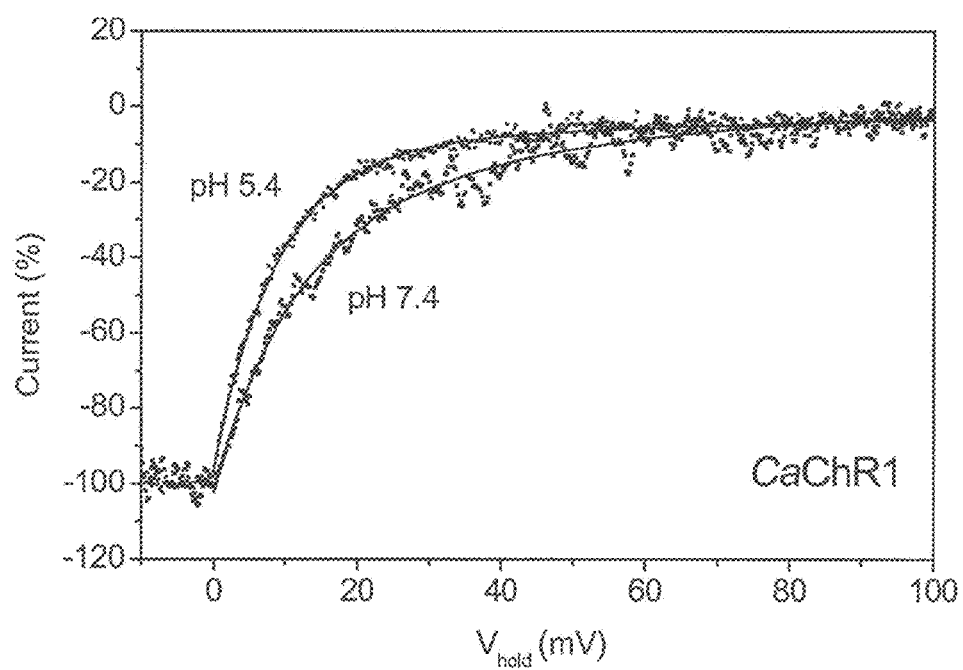

FIG. 29 illustrates normalized current decay traces recorded from cells transfected with CaChR1 from *C. augustae* at holding potential ($V_{hold}$) −60 mV. Traces at the bath pH 7.4 or 5.4 were recorded from the same cell. Zero time corresponds to the end of a 2-s excitation light pulse. Excitation light was as in FIG. 25. Experimental data (dots) were fitted with two exponential functions (solid lines).

Figure 30:
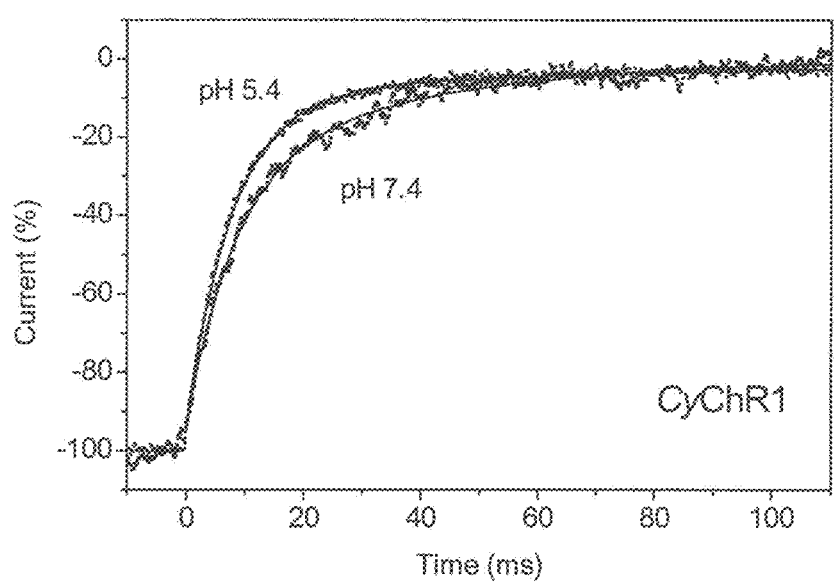

FIG. 30 illustrates normalized current decay traces recorded from cells transfected with, CyChR1 from *C. yellowstonensis* at holding potential ($V_{hold}$) −60 mV. Traces at the bath pH 7.4 or 5.4 were recorded from the same cell. Zero time corresponds to the end of a 2-s excitation light pulse. Excitation light was as in FIG. 26. Experimental data (dots) were fitted with two exponential functions (solid lines).

Figure 31:
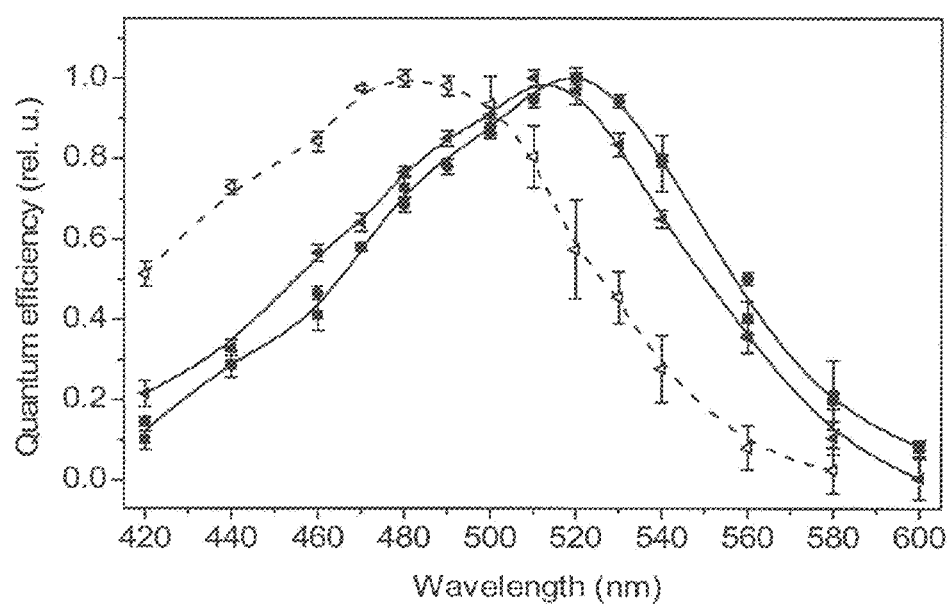

FIG. 31 illustrates the action spectra of photoelectric currents generated in HEK293 cells by CaChR1 from *C. augustae* at the bath pH 7.4 (squares), pH 5.4 (circles) or pH 9.0 (solid triangles). For comparison, the action spectrum of CrChR1 from *C. reinhardtii* measured at pH 7.4 is shown in panel A (open triangles, dashed line).

Figure 32:
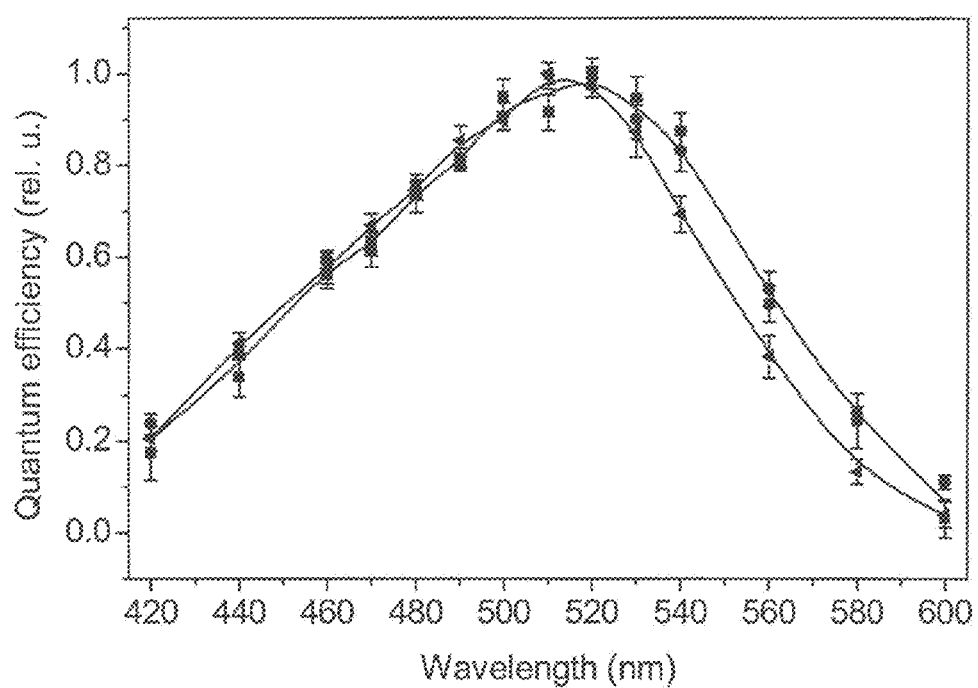

FIG. 32 illustrates the action spectra of photoelectric currents generated in HEK293 cells by CyChR1 from *C. yellowstonensis* at the bath pH 7.4 (squares), pH 5.4 (circles) or pH 9.0 (solid triangles).

Figure 33:
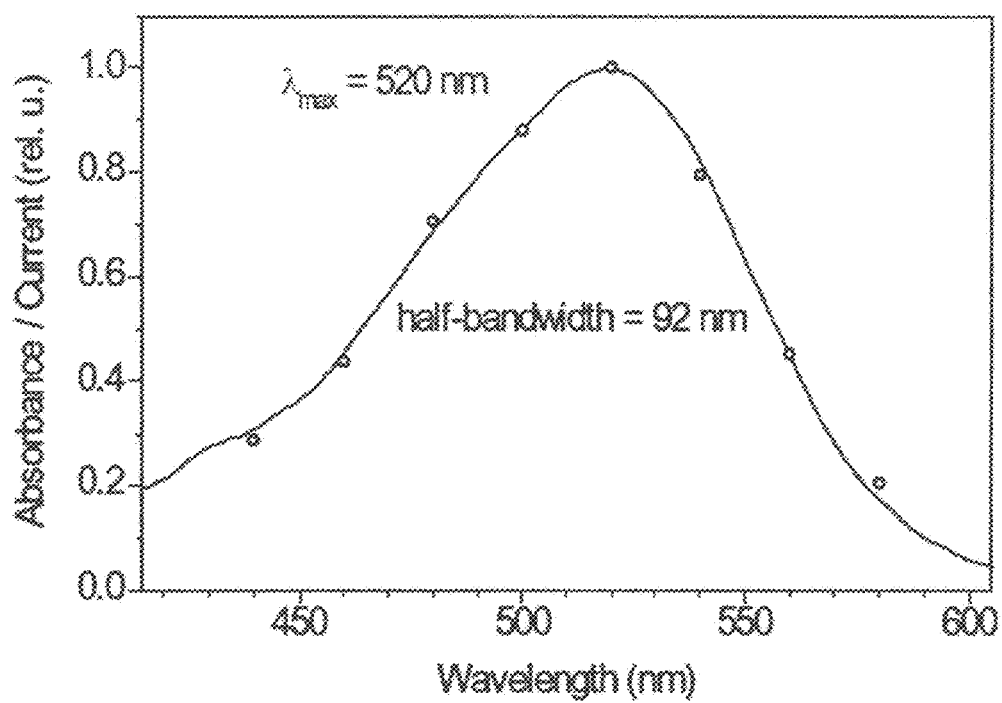

FIG. 33 shows a comparison of the absorption spectrum of purified CaChR1 from *C. augustae* in detergent (line) with the action spectrum of photocurrents (open circles), pH 7.4.

Figure 34:
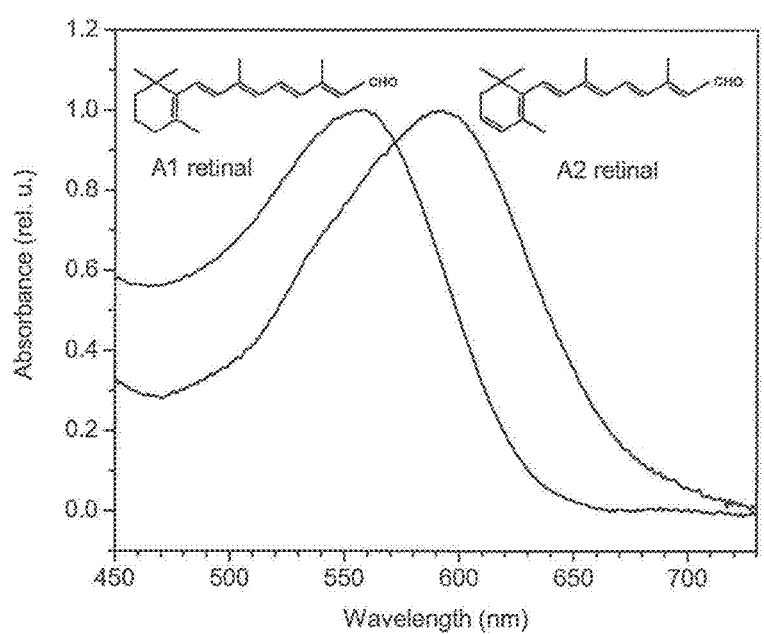

FIG. 34 shows absorption spectra of *E. coli* cells expressing the proton pump AR-3 upon reconstitution with A1 or A2 retinal.

Figure 35:
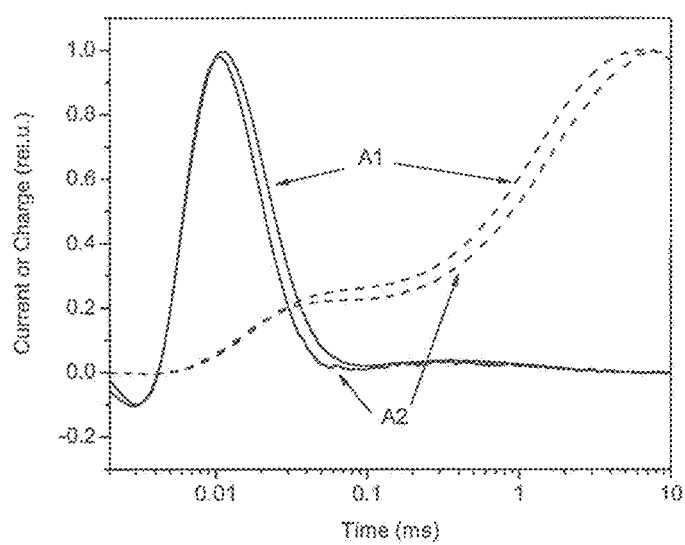

FIG. 35 illustrates photoinduced electrical signals by AR-3 expressed in *E. coli* and reconstituted with A1 or A2 retinal. Solid lines, current traces; dashed lines; transmembrane charge transfer (calculated as area under the current traces). Both sets of curves were normalized for easier kinetics comparison.

Figure 36:
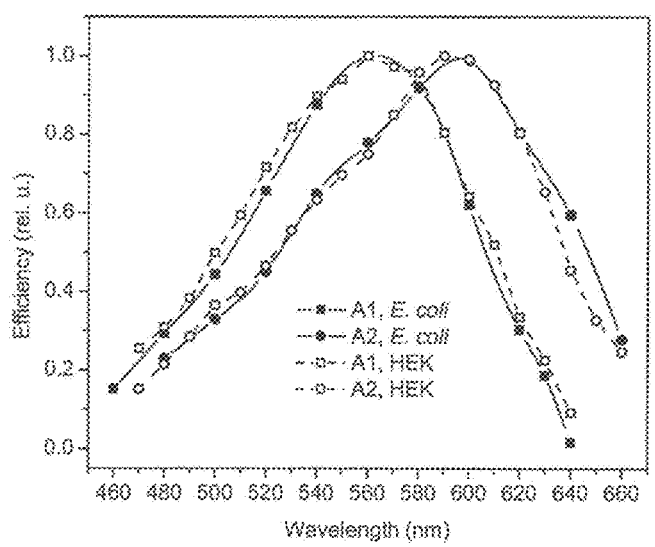

FIG. 36 illustrates action spectra of charge movement by AR-3 expressed in *E. coli* cells (solid symbols, solid lines) or HEK293 cells (open symbols, dashed lines) in the presence of A1 retinal (lines with squares) or A2 retinal (lines with circles).

Figure 37:
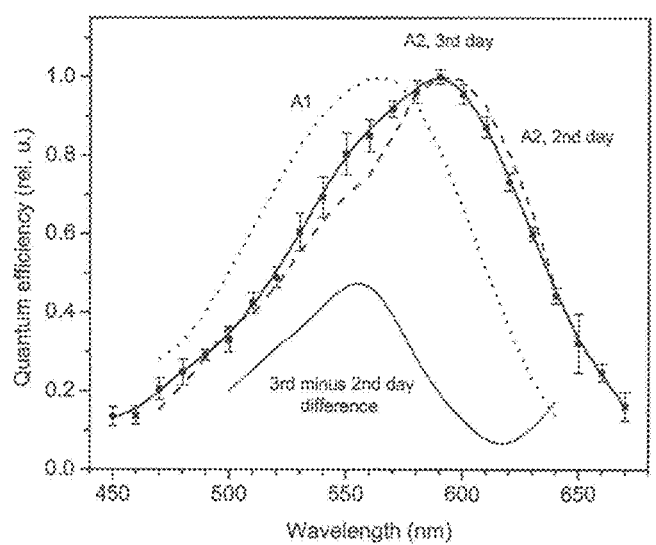

FIG. 37 illustrates action spectra of photocurrents generated by AR-3 at two (dashed line) or three (solid squares, thick solid line) days after the addition of exogenous A2 retinal to HEK293 cells. Dotted line, action spectrum of photocurrent generated by A1-reconstituted AR-3 from FIG. 36; thin solid line, smoothed difference between the 3 d day spectrum and the 2nd day spectrum.

Figure 38:
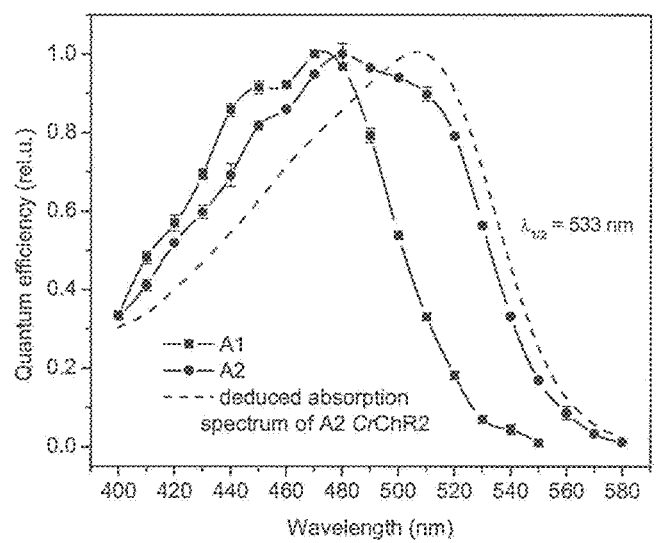

FIG. 38 illustrates action spectra of photoinduced currents generated by CrChR2 from *C. reinhardtii* in HEK cells upon incubation with A1 retinal (line with solid squares), or A2 retinal (line with solid circles). The dashed line shows a deduced spectrum of pure A2-reconstituted CrChR2.

Figure 39:
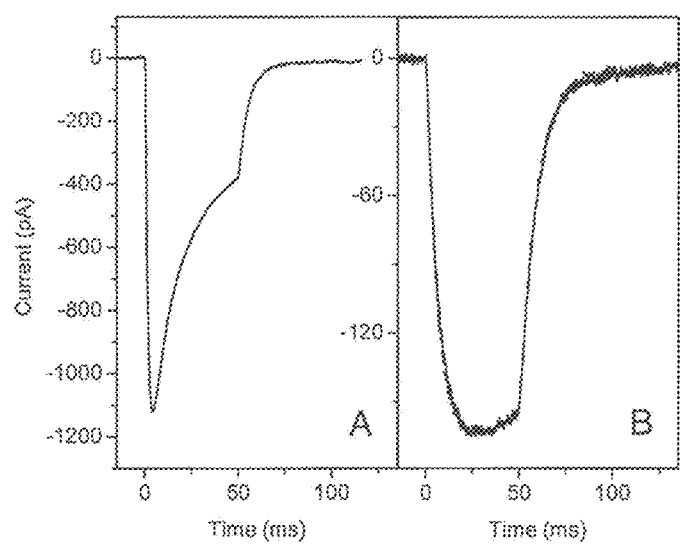

FIGS. 39A-39B illustrate (A) photoelectric currents generated by CrChR2 from *C. reinhardtii*, reconstituted with A2 retinal in response to high-intensity stimuli ($\sim 10^{22}$ photons× $m^2 \times s^{-1}$) at 520 nm. (B) Comparison of the current kinetics at low intensity ($<10^{20}$ photons×$m^2 \times s^{-1}$) in response to 440 nm light, mostly absorbed by the A1 retinal-reconstituted, and 530 nm light, mostly absorbed by the A2 retinal-reconstituted pigment.

Figure 40:
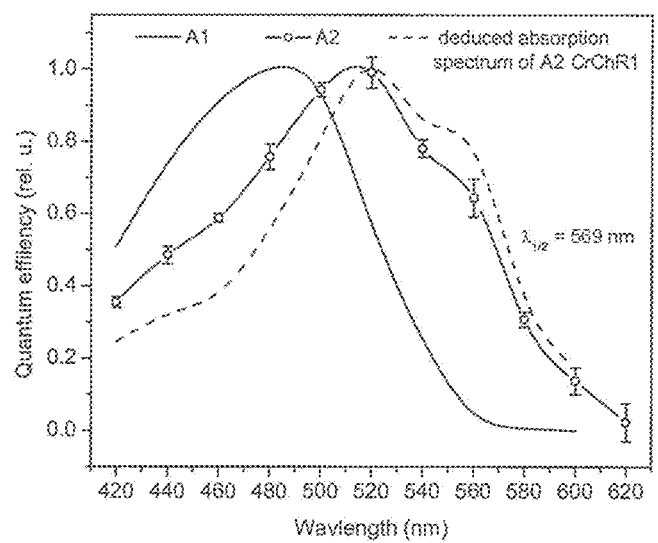

FIG. 40 illustrates action spectra of photocurrents generated by CrChR1 from *C. reinhardtii* in HEK293 cells incubated with A2 retinal (open squares, black line), or A1 retinal (solid line). The dashed line shows the deduced spectrum of pure A2 retinal-reconstituted CrChR1.

Figure 41:
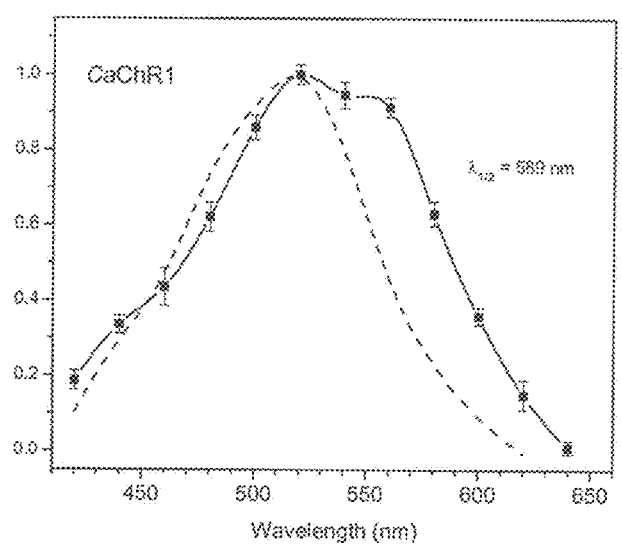

FIG. 41 illustrates action spectra of photocurrents generated by CaChR1 from *C. augustae* in HEK293 cells incubated with A2 retinal (solid squares, solid line), or A1 retinal (dashed line).

Figure 42:
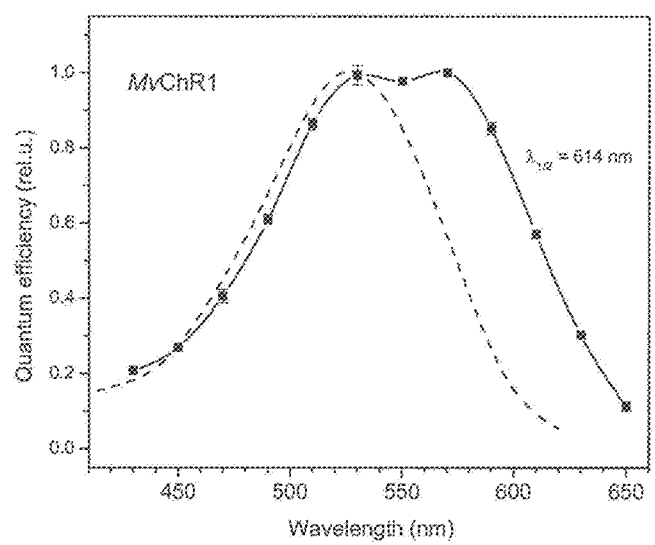

FIG. 42 illustrates action spectra of photocurrents generated by MvChR1 from *M. viride* in HEK293 cells incubated with A2 retinal (solid squares, solid line), or A1 retinal (dashed line), adopted from the examples below.

Figure 43:
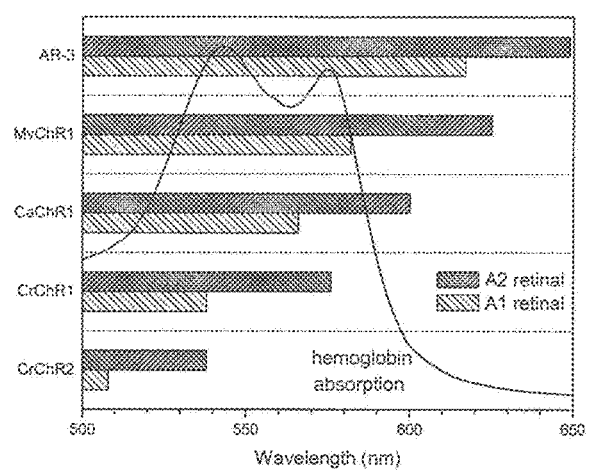

FIG. 43 illustrates the extension of the long-wavelength spectral boundary of the proton pump AR-3 and various channelrhodopsins by incubation with A2 retinal. Bars show the spectral bands with more than 1/e of maximal efficiency for the pigments reconstituted with A1 (cross-hatched pattern) or A2 (hatched pattern) retinal. The absorption spectrum of hemoglobin (oxidized+reduced) is shown for comparison.

Figure 44:
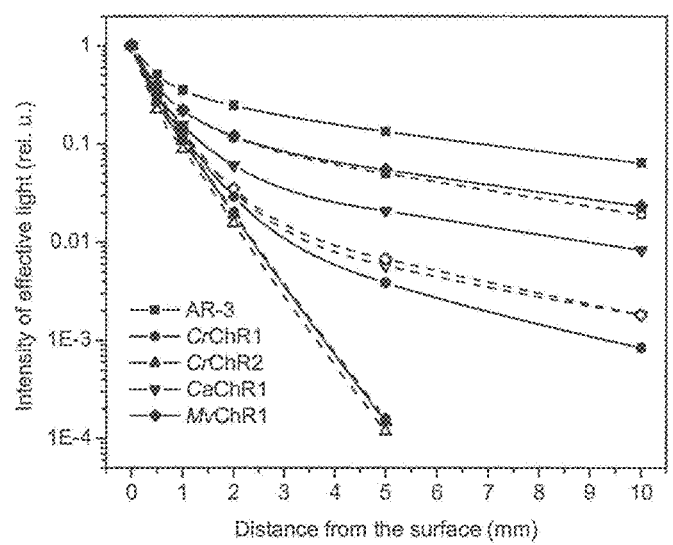

FIG. 44 illustrates a theoretical estimation of the total number of actinic photons absorbed over the visible range by the tested rhodopsins at different depths of brain tissue (for more details see text). Solid symbols and lines, pigments reconstituted with A2 retinal; open symbols and dashed lines, pigments with A1 retinal. Squares AR-3; circles, CrChR1 from *C. reinhardtii*; triangles, CrChR2 from *C. reinhardtii*; inverted triangles, CaChR1 from *C. augustae*; diamonds, MvChR1 from *M. viride*.

Figure 45:
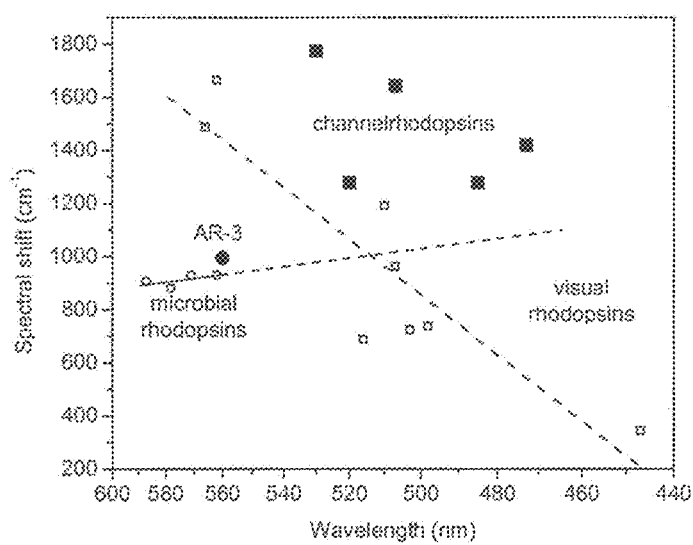

FIG. 45 illustrates spectral shifts of AR-3 (solid circle) and channelrhodopsins (solid squares) compared to the literature data for other microbial rhodopsins (small open circles) and visual pigments (small open squares) adapted from (Dartnall, H. J., and Lythgoe, J. N. (1965) The spectral clustering of visual pigments, *Vision Res.* 5, 81-100; Tokunaga, F., and Ebrey, T. (1978) The blue membrane: the 3-dehydroretinal-based artificial pigment of the purple membrane, *Biochemistry* 17, 1915-1922; Spudich, J. L., McCain, D. A., Nakanishi, K., Okabe, M., Shimizu, N., Rodman, H., Honig, B., and Bogomolni, R. A. (1986) Chromophore/protein interaction in bacterial sensory rhodopsin and bacteriorhodopsin, *Biophys. J.* 49, 479-483; Lanyi, J. K., Zimanyi, L., Nakanishi, K., Derguini, F., Okabe, M., and Honig, B. (1988) Chromophore/protein and chromophore/anion interactions in halorhodopsin, *Biophys. J.* 53, 185-191; Bridges, C. D. (1967) Spectroscopic properties of porphyropsins, *Vision Res.* 7, 349-369; Wald, G., Brown, P. K., and Smith, P. H. (1953) Cyanopsin, a new pigment of cone vision, *Science* 118, 505-508; Parry, J. W., and Bowmaker, J. K. (2000) Visual pigment reconstitution in intact goldfish retina using synthetic retinaldehyde isomers, *Vision Res.* 40, 2241-2247).

DESCRIPTION OF THE SEQUENCE LISTING

The Sequence Listing shows the amino acid sequences of three red-shifted type 1 rhodopsin domains (MChR1, SEQ ID NO: 1; CaChR1, SEQ ID NO: 2 and CyChR1, SEQ ID NO: 3) derived from the channelrhodopsin 1 of *Mesostigma viride* (nucleic acid in SEQ ID NO: 5 and translated amino acid SEQ ID NO: 6); *Chlamydomonas augustae* (nucleic acid in SEQ ID NO: 7 and translated amino acid SEQ ID NO: 8) and *Chlamydomonas yellowstonensis* (nucleic acid in SEQ ID NOS: 9 and translated amino acid SEQ ID NO:10), respectively. Also provided is rhodopsin domain CraChR2 (CrChR2) of SEQ ID NO: 4, which was derived from *Chlamydomonas raudensis* (nucleic acid in SEQ ID NO: 11 and translated amino acid SEQ ID NO: 12)

DETAILED DESCRIPTION

Definitions

In this disclosure, the use of the singular includes the plural, the word "a" or "an" means "at least one," and the use of "or" means "and/or," unless specifically stated otherwise. Furthermore, the use of the term "including," as well as other forms, such as "includes" and "included," is not limiting. Also, terms such as "element" or "component" encompass both elements and components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls As used herein, and unless otherwise indicated, the term neuron mediated disorders for which the present methods and compositions may be used include, but are not limited to, neuronal dysfunctions, disorders of the brain, the central nervous system, the peripheral nervous system, neurological conditions, disorders of memory and leaning disorders, cardiac arrhythmias, Parkinson's disease, ocular disorders, spinal cord injury among others.

As used herein, and unless otherwise indicated, the term ocular disorders for which the present methods and compositions may be used to improve one or more parameters of vision include, but are not limited to, developmental abnormalities that affect both anterior and posterior segments of the eye. Anterior segment disorders include, but are not limited to, glaucoma, cataracts, corneal dystrophy, keratoconus. Posterior segment disorders include, but are not limited to, blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders.

As used herein, and unless otherwise indicated, the terms "treat," "treating," "treatment" and "therapy" contemplate an action that occurs while a patient is suffering from an ocular disorder that reduces the severity of one or more symptoms or effects of an ocular disorder. Where the context allows, the terms "treat," "treating," and "treatment" also refers to actions taken toward ensuring that individuals at increased risk of a neuron mediated disorder or ocular disorders, are able to receive appropriate surgical and/or other medical intervention prior to onset of a neuron mediated disorder or ocular disorder. As used herein, and unless otherwise indicated, the terms "prevent," "preventing," and "prevention" contemplate an action that occurs before a patient begins to suffer from a neuron mediated disorder or ocular disorder, that delays the onset of, and/or inhibits or reduces the severity of a neuron mediated disorder or ocular disorder.

As used herein, and unless otherwise indicated, the terms "manage," "managing," and "management" encompass preventing, delaying, or reducing the severity of a recurrence of an ocular disorder in a patient who has already suffered from such a disease, disorder or condition. The terms encompass modulating the threshold, development, and/or duration of the ocular disorder or changing how a patient responds to a neuron mediated disorder or ocular disorder.

As used herein, and unless otherwise specified, a "therapeutically effective amount" of a compound is an amount sufficient to provide any therapeutic benefit in the treatment or management of a neuron mediated disorder or ocular disorder, or to delay or minimize one or more symptoms associated with a neuron mediated disorder or ocular disorder. A therapeutically effective amount of a compound means an amount of the compound, alone or in combination with one or more other therapies and/or therapeutic agents that provide any therapeutic benefit in the treatment or management of a neuron mediated disorder or ocular disorder. The term "therapeutically effective amount" can encompass an amount that alleviates a neuron mediated disorder or ocular disorder, improves or reduces an ocular disorder, improves overall therapy, or enhances the therapeutic efficacy of another therapeutic agent.

As used herein, and unless otherwise specified, a "prophylactically effective amount" of a compound is an amount sufficient to prevent or delay the onset of a neuron mediated disorder or ocular disorder, or one or more symptoms associated with an ocular disorder or prevent or delay its recurrence. A prophylactically effective amount of a compound means an amount of the compound, alone or in combination with one or more other treatment and/or prophylactic agent that provides a prophylactic benefit in the prevention of a neuron mediated disorder or ocular disorder. The term "prophylactically effective amount" can encompass an amount that prevents a neuron mediated disorder or ocular disorder, improves overall prophylaxis, or enhances the prophylactic efficacy of another prophylactic agent. The "prophylactically effective amount" can be prescribed prior to, for example, the development of a neuron mediated disorder or ocular disorder.

As used herein, "patient" or "subject" includes mammalian organisms which are capable of suffering from an ocular disorder as described herein, such as human and non-human mammals, for example, but not limited to, rodents, mice, rats, non-human primates, companion animals such as dogs and cats as well as livestock, e.g., sheep, cow, horse, etc.

As used herein, the term "conservative substitution" generally refers to amino acid replacements that preserve the structure and functional properties of a protein or polypeptide. Such functionally equivalent (conservative substitution) peptide amino acid sequences include, but are not limited to, additions or substitutions of amino acid residues within the amino acid sequences encoded by a nucleotide sequence that result in a silent change, thus producing a functionally equivalent gene product. Conservative amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, a "redshift" is a shift to longer wavelength. In contrast a "blueshift" would be a shift to shorter wavelength. These terms apply to both light-emitting and light-absorbing objects.

Light control of motility behavior (phototaxis and photophobic responses) in green flagellate algae is mediated by sensory rhodopsins homologous to phototaxis receptors and light-driven ion transporters in prokaryotic organisms. In the phototaxis process, excitation of the algal sensory rhodopsins leads to generation of transmembrane photoreceptor currents. When expressed in animal cells, the algal phototaxis receptors function as light-gated cation channels, which has earned them the name "channelrhodopsins." Channelrhodopsins have become useful molecular tools for light control of cellular activity.

Described herein in some embodiments are compositions and methods for use in generating and obtaining red-shifted channelrhodopsins from algae that are superior to those currently available. Channelrhodopsins are phototaxis receptors that function as light-gated cation channels when transfected into animal cells, are used for photoactivation of neuron firing. Desired properties for such optogenetic uses are red-shifted absorption to minimize light-scattering by biological tissue, minimal inactivation in sustained light, and rapid kinetics of channel closure to allow high-frequency repetitive neuron photostimulation. The previously identified homologs from *Chlamydomonas reinhardtii* and *Volvox carteri* and their genetically engineered variants exhibit some of these properties, but none exhibits all.

As used herein, the channelopsin is the apoprotein, while channelrhodopsin is the protein and retinal. Strictly speaking the amino acid sequences (identified in SEQ ID NOS: 1-4) define the opsin, but this is also the sequence of the rhodopsin, which is the same.

By screening phototaxis receptor currents among several algal species, several red-shifted channelrhodopsins with rapid kinetics were identified and characterized. In some embodiments, the disclosed methods provide a technology that facilities the identification and characterization of particularly useful channelrhodopsins from algae (such as but not limited to, *Mesostigma viride, Chlamydomonas augustae, Chlamydomonas yellowstonensis*, Chlorophyceae, *Chlamydomonas reinhardtii, Acetabularia, Ulva, Pyramimonas, Platymonas (Tetraselmis)*.

In some embodiments, provided are amino acid and nucleic acid sequences of functional domains of novel channelrhodopsins that are also functionally characterized. Three of these channelrhodopsins have been determined to have red-shifted absorption maxima and functional type 1 rhodopsin domains of the channelrhodopsins were cloned and identified as MvChR1 or MChR1 (SEQ ID NO: 1) which was derived from channelrhodopsin 1 of *Mesostigma viride* (SEQ ID NOS: 5 and 6, EMBL entry JF922293.1); CaChR1 (SEQ ID NO: 2) which was derived from channelrhodopsin 1 of *Chlamydomonas augustae* (SEQ ID NO: 7 and 8, EMBL entry JN596951.1; and CyChR1 (SEQ ID NO: 3) which was derived from channelrhodopsin 1 *Chlamydomonas yellowstonensis* (SEQ ID NOS: 9 and 10, see EMBL entry JN596948.1).

Also provided, in some embodiments, is the use and composition of a fourth novel channelrhodopsin domain, identified as CraChR or CrChR (SEQ ID NO: 4) which was derived from channelrhodopsin 2 of *Chlamydomonas raudensis* (SEQ ID NOS: 11 and 12, EMBL entry JN596949.1., in one publication this was referred to as CraChR2 (Hou, S.-Y., Govorunova, E. G., Ntefidou, M., Lane, C. E., Spudich, E. N., Sineshchekov, O. A., and Spudich, J. L. Diversity of *Chlamydomonas* channelrhodopsins, *Photochem. Photobiol.*, 88: 119-128, 2012).

In other embodiments, are methods compositions that provide channelrhodopsins with improved properties and characteristics that enhance the application of these compositions in, among other things, optogenetic techniques. These embodiments involve, among others, the enhancement of the long-wavelength sensitivity, by inducing a redshift in absorption maxima.

Optogenetic techniques involve the introduction of light-activated channels and enzymes that allow manipulation of neural activity and control of neuronal function. Thus, in some embodiments, the disclosed methods and compositions can be introduced into cells and facilitate the manipulation of the cells activity and function.

Optogenetic techniques, and thus the disclosed methods and compositions, can be used to, among other things, characterize the functions of complex neural circuits and information processing in the normal brain and during various neurological conditions; functionally map the cerebral cortex; characterize and manipulate the process of learning and memory; characterize and manipulate the process of synaptic transmission and plasticity; provide light-controlled induction of gene expression; provide optical control of cell motility and other activities.

Clinical applications of the disclosed methods and compositions include, but are not limited to, optogenetic approaches to therapy such as, but are not limited to, restoration of vision by introduction of channelrhodopsins in post-receptor neurons in the retina for ocular disorder gene-therapy treatment of age-dependent macular degeneration, diabetic retinopathy, and retinitis pigmentosa, as well as other conditions which result in loss of photoreceptor cells; control of cardiac function by using channelrhodopsins incorporated into excitable cardiac muscle cells in the atrioventricular bundle (bundle of His) to control heart beat rhythm rather than an electrical pacemaker device; restoration of dopamine-related movement dysfunction in Parkinsonian patients; amelioration of depression; recovery of breathing after spinal cord injury; provide noninvasive control of stem cell differentiation and assess specific contributions of transplanted cells to tissue and network function.

In some embodiments, particular red-shifted channelrhodopsins with rapid kinetics are provided, including, MChR1 (SEQ ID NO: 1) which was derived from *Mesostigma viride*; CaChR1 (SEQ ID NO: 2) which was derived from *Chlamydomonas augustae*; and CyChR1 (SEQ ID NO: 3) which was derived from *Chlamydomonas yellowstonensis* may be used to enhance, among other things, optogenetic techniques and optogenetic approaches to therapy.

Channelrhodopsins, functional or active portions thereof, such as but not limited to the type 1 rhodopsin domain, and functional equivalents include, but are not limited to, naturally occurring versions of channelrhodopsin and those that are orthologs and homologs, and mutant versions of channelrhodopsin, whether naturally occurring or engineered (by site directed mutagenesis, gene shuffling, or directed evolution, as described in, for example, U.S. Pat. No. 5,837,458). Also included are the use of degenerate nucleic acid variants (due to the redundancy of the genetic code) of the disclosed an algae derived channelrhodopsin polynucleotide sequences.

In some embodiments, are isolated nucleic acid molecules comprising a nucleotide sequence that encodes the type 1 rhodopsin domain of a red-shifted channelrhodopsin derived from algae. In some embodiments, the type 1 rhodopsin domain encodes the peptides whose sequence is described in a group consisting of SEQ ID NO: 1, SEQ ID NO: 2 or SEQ ID NO: 3. In some embodiments, are isolated nucleic acid molecules comprising a nucleotide sequence that encodes the amino acid sequence shown in SEQ ID NO: 1, SEQ ID NO: 2 or SEQ ID NO: 3. In some embodiments, are expression vectors comprising a nucleic acid sequence that encodes the amino acid sequences of SEQ ID NO: 1, SEQ ID NO: 2 or SEQ ID NO: 3. In some embodiments, are host cells comprising a expression vector comprising a nucleic acid sequence that encodes the amino acid sequences of SEQ ID NO: 1, SEQ ID NO: 2 or SEQ ID NO: 3.

In some embodiments, are isolated nucleic acid molecules comprising a nucleotide sequence that encodes the rhodopsin domain of a channelrhodopsin derived from algae. In some embodiments, the rhodopsin domain encodes the peptides whose sequence is described in SEQ ID NO: 4. In some embodiments, are isolated nucleic acid molecules comprising a nucleotide sequence that encodes the amino acid sequence shown in SEQ ID NO: 4. In some embodiments, are expression vectors comprising a nucleic acid sequence that encodes the amino acid sequences of SEQ ID NO: 4. In some embodiments, are host cells comprising a expression vector comprising a nucleic acid sequence that encodes the amino acid sequences of SEQ ID NO: 4.

In some embodiments, are isolated peptides comprising a sequence that encodes the type 1 rhodopsin domain of a red-shifted channelrhodopsin derived from algae. In some embodiments, are isolated peptides comprising an amino acid sequence of a group consisting of SEQ ID NO: 1, SEQ ID NO: 2 or SEQ ID NO: 3.

In some embodiments, are isolated peptides comprising a sequence that encodes the rhodopsin domain of a channelrhodopsin derived from algae. In some embodiments, are isolated peptides comprising an amino acid sequence of SEQ ID NO: 4. In some embodiments, are isolated peptides comprising an amino acid sequence of a group consisting of SEQ ID NO: 1, SEQ ID NO: 2 or SEQ ID NO: 3 and function as a channelrhodopsin. In some embodiments, are isolated peptides comprising an amino acid sequence of SEQ ID NO: 4 and function as a channelrhodopsin.

In some embodiments, are isolated nucleic acid molecules comprising a nucleotide sequence that encodes the type 1 rhodopsin of a red-shifted channelrhodopsin derived from algae. In some embodiments, the type 1 rhodopsin encodes a peptide whose sequence is described in a group consisting of SEQ ID NO: 6, SEQ ID NO: 8 or SEQ ID NO: 10. In some embodiments, are isolated nucleic acid molecules comprising a nucleotide sequence that encodes the amino acid sequence shown in SEQ ID NO: 6, SEQ ID NO: 8 or SEQ ID NO: 10. In some embodiments, are expression vectors comprising a nucleic acid sequence that encodes the amino acid sequences of SEQ ID NO: 6, SEQ ID NO: 8 or SEQ ID NO: 10. In some embodiments, are host cells comprising a expression vector comprising a nucleic acid sequence that encodes the amino acid sequences of SEQ ID NO: 6, SEQ ID NO: 8 or SEQ ID NO: 10.

In some embodiments, are peptides comprising a sequence that encodes the type 1 rhodopsin domain of a red-shifted channelrhodopsin derived from algae. In some embodiments, are isolated peptides comprising an amino acid sequence of a group consisting of SEQ ID NO: 6, SEQ ID NO: 8 or SEQ ID NO: 10. In some embodiments, are isolated peptides comprising a sequence that encodes the rhodopsin domain of channelrhodopsin derived from algae. In some embodiments, the isolated peptides comprise an amino acid sequence of SEQ ID NO: 12.

In some embodiments, are isolated nucleic acid molecules wherein said nucleic acid molecule has a sequence is selected from the group consisting of SEQ ID NO: 5, SEQ ID NO: 7, SEQ ID NO: 9 or SEQ ID NO: 11. In some embodiments, are expression vectors comprising a nucleic acid sequence selected from the group consisting of SEQ ID NO: 5, SEQ ID NO: 7, SEQ ID NO: 9 or SEQ ID NO: 11. In some embodiments, are host cells comprising a expression vector comprising a nucleic acid sequence selected from the group consisting of SEQ ID NO: 5, SEQ ID NO: 7, SEQ ID NO: 9 or SEQ ID NO: 11. In some embodiments, an isolated nucleic acid comprises a nucleotide sequence that encodes the type 1 rhodopsin domain of a red-shifted channelrhodopsin derived from algae. In some embodiments, the nucleotide sequence encodes at least 16 contiguous amino acids of SEQ ID NO: 1, SEQ ID NO: 2, or SEQ ID NO: 3. In some embodiments, the nucleotide sequence encodes at least 20 contiguous amino acids of SEQ ID NO: 1, SEQ ID NO: 2 or SEQ ID NO: 3. In some embodiments, the nucleotide sequence encodes at least 35 contiguous amino acids of SEQ ID NO: 1, SEQ ID NO: 2 or SEQ ID NO: 3. In some embodiments, the nucleotide sequence encodes at least 50 contiguous amino acids of SEQ ID NO:1, SEQ ID NO: 2 or SEQ ID NO: 3. In some embodiments, the nucleotide sequence encodes at least 75 contiguous amino acids of SEQ ID NO:1, SEQ ID NO:2 or SEQ ID NO:3. In some embodiments, the nucleotide sequence encodes at least 33 contiguous amino acids of SEQ ID NO: 1, SEQ ID NO: 2 or SEQ ID NO: 3. In some embodiments, the nucleotide sequence encodes a peptide comprising SEQ ID NO: 1, SEQ ID NO: 2 or SEQ ID NO: 3.

In some embodiments, an isolated polypeptide encodes the type 1 rhodopsin domain of a red-shifted channelrhodopsin derived from algae. In some embodiments, an isolated polypeptide comprising the amino acid sequence of SEQ ID NO: 1, SEQ ID NO: 2 or SEQ ID NO: 3. In some embodiments, the isolated polypeptide has at least 85% homology to the amino acid sequence of SEQ ID NO:1, SEQ ID NO:2 or SEQ ID NO:3. In some embodiments, a protein composition comprises a polypeptide having the amino acid sequence of SEQ ID NO: 1, SEQ ID NO: 2 or SEQ ID NO: 3.

In some embodiments, an isolated nucleic acid comprises a nucleotide sequence that encodes the rhodopsin domain of a novel channelrhodopsin derived from *C. raudensis*. In some embodiments, the nucleotide sequence encodes at least 16 contiguous amino acids of SEQ ID NO: 4. In some embodiments, the nucleotide sequence encodes at least 20 contiguous amino acids of SEQ ID NO: 4. In some embodiments, the nucleotide sequence encodes at least 35 contiguous amino acids of SEQ ID NO: 4. In some embodiments, the nucleotide sequence encodes at least 50 contiguous amino acids of SEQ ID NO: 4. In some embodiments, the nucleotide sequence encodes at least 75 contiguous amino acids of SEQ ID NO: 4. In some embodiments, the nucleotide sequence encodes at least 33 contiguous amino acids of SEQ ID NO: 4. In some embodiments, the nucleotide sequence encodes a peptide comprising SEQ ID NO: 4.

In some embodiments, an isolated polypeptide encodes the rhodopsin domain of a channelrhodopsin derived from *C. raudensis*. In some embodiments, an isolated polypeptide comprising the amino acid sequence of SEQ ID NO: 4. In some embodiments, the isolated polypeptide has at least 85% homology to the amino acid sequence of SEQ ID NO: 4. In some embodiments, a protein composition comprises a polypeptide having the amino acid sequence of SEQ ID NO: 4.

In some embodiments, an isolated nucleic acid comprising a nucleotide sequence that encodes a functional domain of a channelrhodopsin of *Mesostigma viride, Chlamydomonas augustae, Chlamydomonas yellowstonensis* or *Chlamydomonas raudensis*. In some embodiments are isolated nucleic acid that encodes at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200, 225, 250, 275, 300, 325, 350, 375, 400, 500, 600, 700, 800, 900 or more contiguous amino acids of SEQ ID NO: 1, SEQ ID NO: 2, SEQ ID NO: 3, SEQ ID NO: 4, SEQ ID NO: 6, SEQ ID NO: 8, SEQ ID NO: 10 SEQ ID NO: 12 or fragments thereof. Further, in some embodiments, any range derivable between any of the above-described integers.

In other embodiments, the present invention provides for an isolated polypeptide or an isolated nucleic acid encoding a polypeptide having between about 70% and about 75%; or more preferably between about 75% and about 80%; or more preferably between about 80% and 90%; or even more preferably between about 90% and about 99% of amino acids that are identical to the amino acids of SEQ ID NO: 1, SEQ ID NO: 2, SEQ ID NO:3, SEQ ID NO: 4, SEQ ID NO: 6, SEQ ID NO: 8, SEQ ID NO: 10, SEQ ID NO: 12 or fragments thereof. The percent identity or homology is determined with regard to the length of the relevant amino acid sequence. Therefore, if a polypeptide of the present invention is comprised within a larger polypeptide, the percent homology is determined with regard only to the portion of the polypeptide that corresponds to the polypeptide of the present invention and not the percent homology of the entirety of the larger polypeptide.

In other embodiments, the present invention provides for an isolated nucleic acid encoding a polypeptide having between about 70% and about 75%; or more preferably between about 75% and about 80%; or more preferably between about 80% and 90%; or even more preferably between about 90% and about 99% of amino acids that are identical to the amino acids of SEQ ID NO: 5, SEQ ID NO: 7, SEQ ID NO: 9, SEQ ID NO: 11 or fragments thereof.

In some embodiments, the nucleic acid segments, regardless of the length of the coding sequence itself, may be combined with other DNA sequences, such as promoters, enhancers, polyadenylation signals, additional restriction enzyme sites, multiple cloning sites, other coding segments, and the like.

In certain embodiments the invention provides an isolated nucleic acid obtained by amplification from a template nucleic acid using a primer selected from the group consisting of SEQ ID NO: 13, SEQ ID NO: 14, and SEQ ID NO: 15.

In some embodiments, a recombinant host cell comprising one of the nucleic acid sequences described. In some embodiments, a protein composition comprising one of the polypeptides described.

In some embodiments, are methods of treating a neuronal disorder, comprising: (a) delivering to a target neuron a nucleic acid expression vector that encodes a type 1 rhodopsin domain of a red-shifted channelrhodopsin derived from algae, expressible in said target neuron, said vector comprising an open reading frame encoding the type 1 rhodopsin domain of a red-shifted channelrhodopsin, operatively linked to a promoter sequence, and optionally, a transcriptional regulatory sequence; and (b) expressing said vector in said target neuron, wherein the expressed rhodopsin activates said target neuron upon exposure to light. In some embodiments, the type 1 rhodopsin domain is encoded by SEQ ID NOS: 1-3.

In some embodiments, are methods of treating a neuronal disorder, comprising: (a) delivering to a target neuron a nucleic acid expression vector that encodes a rhodopsin domain of a channelrhodopsin derived from algae, expressible in said target neuron, said vector comprising an open reading frame encoding the rhodopsin domain of a channelrhodopsin, operatively linked to a promoter sequence, and optionally, a transcriptional regulatory sequence; and (b) expressing said vector in said target neuron, wherein the expressed rhodopsin activates said target neuron upon exposure to light. In some embodiments, the rhodopsin domain is encoded by SEQ ID NO: 4.

In some embodiments, are methods of restoring light sensitivity to a retina, comprising: (a) delivering to a retinal neuron a nucleic acid expression vector that encodes a type 1 rhodopsin domain of a red-shifted channelrhodopsin derived from algae, expressible in the retinal neuron; said vector comprising an open reading frame encoding the type 1 rhodopsin domain of a red-shifted channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring light sensitivity to said retina or a portion thereof. In some embodiments, the type 1 rhodopsin domain is encoded by SEQ ID NOS: 1-3.

In some embodiments, are methods of restoring light sensitivity to a retina, comprising: (a) delivering to a retinal neuron a nucleic acid expression vector that encodes a rhodopsin domain of a red-shifted channelrhodopsin derived from algae, expressible in the retinal neuron; said vector comprising an open reading frame encoding the rhodopsin domain of a red-shifted channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring light sensitivity to said retina or a portion thereof. In some embodiments, the type 1 rhodopsin domain is encoded by SEQ ID NO: 4.

In some embodiments, are methods of restoring photosensitivity to a retina of a subject suffering from vision loss or blindness in whom retinal photoreceptor cells are degenerating or have degenerated and died, said method comprising: (a) delivering to the retina of said subject a nucleic acid vector that encodes a type 1 rhodopsin domain of a red-shifted channelrhodopsin derived from algae expressible in a retinal neuron; said vector comprising an open reading frame encoding the type 1 rhodopsin domain of a red-shifted channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring photosensitivity to said retina or a portion thereof. In some embodiments, the type 1 rhodopsin domain is encoded by SEQ ID NOS: 1-3.

In some embodiments, are methods of restoring photosensitivity to a retina of a subject suffering from vision loss or blindness in whom retinal photoreceptor cells are degenerating or have degenerated and died, said method comprising: (a) delivering to the retina of said subject a nucleic acid vector that encodes a rhodopsin domain of a red-shifted channelrhodopsin derived from algae expressible in a retinal neuron; said vector comprising an open reading frame encoding the rhodopsin domain of a red-shifted channelrhodopsin operatively linked to a promoter sequence, and optionally, a transcriptional regulatory sequence; and (b) expressing said vector in said retinal neuron, wherein the expressed rhodopsin renders said retinal neuron photosensitive, thereby restoring photosensitivity to said retina or a portion thereof. In some embodiments, the type 1 rhodopsin domain is encoded by SEQ ID NO: 4.

In some embodiments, are any of the disclosed methods, wherein the type 1 rhodopsin domain of a red-shifted channelrhodopsin having the amino acid sequence of all or part of SEQ ID NOS: 1, 2 or 3, or a biologically active fragment thereof that retains the biological activity of the encoded type 1 rhodopsin domain of a red-shifted channelrhodopsin or a biologically active conservative amino acid substitution variant of SEQ ID NOS: 1, 2 or 3 or of said fragment.

In some embodiments, are any of the disclosed methods, wherein the rhodopsin domain of a red-shifted channelrhodopsin having the amino acid sequence of all or part of SEQ ID NO: 4, or a biologically active fragment thereof that retains the biological activity of the encoded rhodopsin domain of a red-shifted channelrhodopsin or a biologically active conservative amino acid substitution variant of SEQ ID NO: 4 or of said fragment.

In some embodiments, are any of the disclosed methods wherein the expression vectors include, but are not limited to, AAV viral vector. In some embodiments, are any of the disclosed methods wherein the promoter is a constitutive promoter. In some embodiments, are any of the disclosed methods wherein the constitutive promoter includes, but is not limited to, a CMV promoter or a hybrid CMV enhancer/chicken β-actin (CAG) promoter. In some embodiments, are any of the disclosed methods wherein the promoter includes, but is not limited to, an inducible and/or a cell type-specific promoter.

In some embodiments, a method of treating a neuronal disorder comprises: (a) delivering to a target neuron a nucleic acid expression vector that encodes a type 1 rhodopsin domain of a red-shifted channelrhodopsin derived from algae, expressible in said target neuron; said vector comprising an open reading frame encoding the type 1 rhodopsin domain of a red-shifted channelrhodopsin operatively linked to a promoter sequence, and optionally, transcriptional regulatory sequences; and (b) expressing the expression vector in the target neuron, wherein the expressed channelrhodopsin activates the target neuron upon exposure to light. In some embodiments an above-described expression vector also comprises one or more transcriptional regulatory sequences operably linked to the promoter and type 1 rhodopsin domain sequences. In some embodiments, the type 1 rhodopsin domain of a red-shifted channelrhodopsin has the amino acid sequence of all or part of SEQ ID NOS: 1, 2 or 3 and the rhodopsin domain sequences of SEQ ID NO:4, or a biologically active fragment thereof that retains the biological activity of the encoded rhodopsin domain of a channelrhodopsin or is a biologically active conservative amino acid substitution variant of SEQ ID NOS: 1, 2, 3 or 4 or of said fragment. In some embodiments, the expression vector comprises an AAV viral vector. In some embodiments, the promoter is a constitutive promoter. In some embodiments, the constitutive promoter is a CMV promoter or a hybrid CMV enhancer/chicken β-actin (CAG) promoter. In some embodiments, the promoter is an inducible and/or a cell type-specific promoter.

In some embodiments, a method of restoring light sensitivity to a retina comprises: (a) delivering to a retinal neuron in a subject a nucleic acid expression vector that encodes a type 1 rhodopsin domain of a red-shifted channelrhodopsin derived from algae, expressible in the retinal neuron; said expression vector comprising an open reading frame encoding the type 1 rhodopsin domain of a red-shifted channelrhodopsin operatively linked to a promoter sequence, and optionally, one or more transcriptional regulatory sequences; and (b) expressing the expression vector in the retinal neuron, wherein the expressed rhodopsin renders the retinal neuron photosensitive, thereby restoring light sensitivity to the retina or a portion thereof. In some embodiments, the type 1 rhodopsin domain of a red-shifted channelrhodopsin has the amino acid sequence of all or part of SEQ ID NOS: 1-3 and therhodopsin domain sequences of SEQ ID NO: 4, or a biologically active fragment thereof that retains the biological activity of the encoded type 1 rhodopsin domain of a red-shifted channelrhodopsin or is a biologically active conservative amino acid substitution variant of SEQ ID NOS: 1-3 and the rhodopsin domain sequences of SEQ ID NO: 4, or of said fragment. In some embodiments, the expression vector comprises an AAV viral vector. In some embodiments, the promoter is a constitutive promoter. In some embodiments, the constitutive promoter is a CMV promoter or a hybrid CMV enhancer/chicken β-actin (CAG) promoter. In some embodiments, the promoter is an inducible and/or a cell type-specific promoter.

In some embodiments, a method of restoring photosensitivity to a retina of a subject suffering from vision loss or blindness in whom retinal photoreceptor cells are degenerating or have degenerated and died comprises: (a) delivering to the retina of the subject a nucleic acid expression vector that encodes a type 1 rhodopsin domain of a red-shifted channelrhodopsin derived from algae expressible in retinal neurons; said expression vector comprising an open reading frame encoding the type 1 rhodopsin domain of a red-shifted channelrhodopsin operatively linked to a promoter sequence, and optionally, transcriptional regulatory sequences; and (b) expressing the expression vector in the retinal neuron, wherein the expression of the rhodopsin renders the retinal neuron photosensitive, thereby restoring photosensitivity to said retina or a portion thereof. In some embodiments, the type 1 rhodopsin domain of a red-shifted channelrhodopsin has the amino acid sequence of all or part of SEQ ID NOS: 1-3 and the rhodopsin domain sequences of SEQ ID NO: 4, or a biologically active fragment thereof that retains the biological activity of the encoded type 1 rhodopsin domain of a red-shifted channelrhodopsin or is a biologically active conservative amino acid substitution variant of SEQ ID NOS: 1-3 and the rhodopsin domain sequences of SEQ ID NO: 4, or of said fragment. In some embodiments, the expression vector comprises an AAV viral vector. In some embodiments, the promoter is a constitutive promoter. In some embodiments, the constitutive promoter is a CMV promoter or a hybrid CMV enhancer/chicken β-actin (CAG) promoter. In other embodiments, the promoter is an inducible and/or a cell type-specific promoter.

To identify algal species were screened for candidates of new channelrhodopsins with desirable characteristics, using the photoelectrophysiological population assay for recording rhodopsin-mediated photocurrents. EST and homology cloning was also used to identify new channelopsin sequences in several algal species.

Exemplified below are the specifics of the process. MChR1 (SEQ ID NO: 1) which was derived from channelrhodopsin 1 of *Mesostigma viride* (SEQ ID NOS: 5 and 6, EMBL entry JF922293.1); CaChR1 (SEQ ID NO: 2) which was derived from channelrhodopsin 1 of *Chlamydomonas augustae* (SEQ ID NO: 7 and 8, EMBL entry JN596951.1; and CyChR1 (SEQ ID NO: 3) which was derived from channelrhodopsin 1 *Chlamydomonas yellowstonensis* (SEQ ID NOS: 9 and 10, see EMBL entry JN596948.1) were cloned and expressed and are established as proteins having the most red-shifted spectral sensitivities so far reported, matches or surpasses known channelrhodopsins' channel kinetics, undergoes minimal inactivation upon sustained illumination, and exhibits pH-independent spectral sensitivity of membrane depolarization. This combination of properties makes MChR1 (SEQ ID NO: 1), CaChR1 (SEQ ID NO: 2) and CyChR1 (SEQ ID NO: 3) particularly useful as a more precise and versatile agent for control of neuronal activity as well as for optogenetic uses.

In some embodiments, the cloning and analysis of new channelopsins from a phylogenetically different alga expands the set of the currently available optogenetic techniques by introducing a fast, red-shifted and little-inactivated channelrhodopsin species, and also contributes to our understanding of the sequence determinants of channelrhodopsin function. Furthermore, retinal neurons not normally sensitive to direct light located in the retinas of blind mice, such as retinal ganglion cells (RGCs) and bipolar cells, can respond to light when a green algae protein called channelrhodopsin-2 (ChR2), or a biologically active fragment or a conservative amino acid substitution variant thereof, is inserted into the neuronal cell membranes. In some embodiments the described channelrhodopsins may be used to transform retinal neurons not normally sensitive to direct light located in the retinas. In some embodiments, are methods and compositions of a novel channelrhodopsin 2 domain, identified as CraChr (CrChR) (SEQ ID NO: 4) which was derived from channelopsin 2 of *Chlamydomonas raudensis* (SEQ ID NOS: 11 and 12, EMBL entry JN596949.1).

In some embodiments, molecular engineered variants (some with improved activity) of the described red-shifted channelrhodopsins by site-specific mutagenesis and chimera construction. In some embodiments, the channelrhodopsins serve as receptors for phototaxis and the photophobic response. Their photoexcitation initiates depolarization of the cell membrane.

In some embodiments, the type 1 rhodopsin domains of several channelrhodopsins were cloned and determined to have channel activity when they were expressed in mammalian HEK293 cells. Using these methods new channelrhodopsin variants, were determined to have improved properties with regards to, among other things, optogenetics. It has a more red-shifted spectral sensitivity at neutral pH than the previously available most red-shifted VChR1, and surpasses VChR1 by faster current kinetics and smaller inactivation, all of which makes these type 1 rhodopsin domains better suited for, among other things, rapid control of neuronal activity.

The presently disclosed compositions and methods exemplified herein, demonstrate that that screening flagellate species by measuring rhodopsin-mediated photoelectric currents in vivo is an efficient method for identifying source organisms from which new channelrhodopsins with characteristics desirable for optogenetic applications can be isolated, cloned and expressed. Such screening cannot be performed by measuring phototaxis itself, i.e., the behavioral response, because even if an alga demonstrates phototaxis, it is not necessarily mediated by a channelrhodopsin. As evidenced by a well-known example is Euglena, which uses a flavin-binding adenylyl cyclase as a receptor for light control of motility. The properties of properties of the cell's channelrhodopsins can only be probed in algal cells by measuring photoelectric responses.

Several channelrhodopsins were identified and characterized. MChR1 (SEQ ID NO: 1) which was derived from *Mesostigma viride*; CaChR1 (SEQ ID NO: 2) which was derived from *Chlamydomonas augustae*; and CyChR1 (SEQ ID NO: 3) which was derived from *Chlamydomonas yellowstonensis*.

MChR1 is a channelrhodopsin that was cloned from the flagellate alga *M. viride* identified as a candidate species by the above approach. When MChR1 was expressed in HEK cells it was determined that: (a) it exhibits the most red-shifted absorption among all studied channelrhodopsins; (b) its current kinetics is significantly faster than that of the other known red-shifted channelrhodopsin VChR1; (c) it showed lower inactivation than VChR1 when stimulated with light of the same wavelength; and (d) the spectral sensitivity of channel activity was pH-independent. These four qualities are highly desirable for an optogenetic tool intended for high-frequency control of rapid neuronal spiking.

MChR1 is expected to retain its excellent properties when expressed in neurons, because it has been shown earlier that photocurrents generated by channelrhodopsins in HEK cells were quantitatively indistinguishable from those generated in neurons using channelrhodopsin-2 (30).

Figure 15:
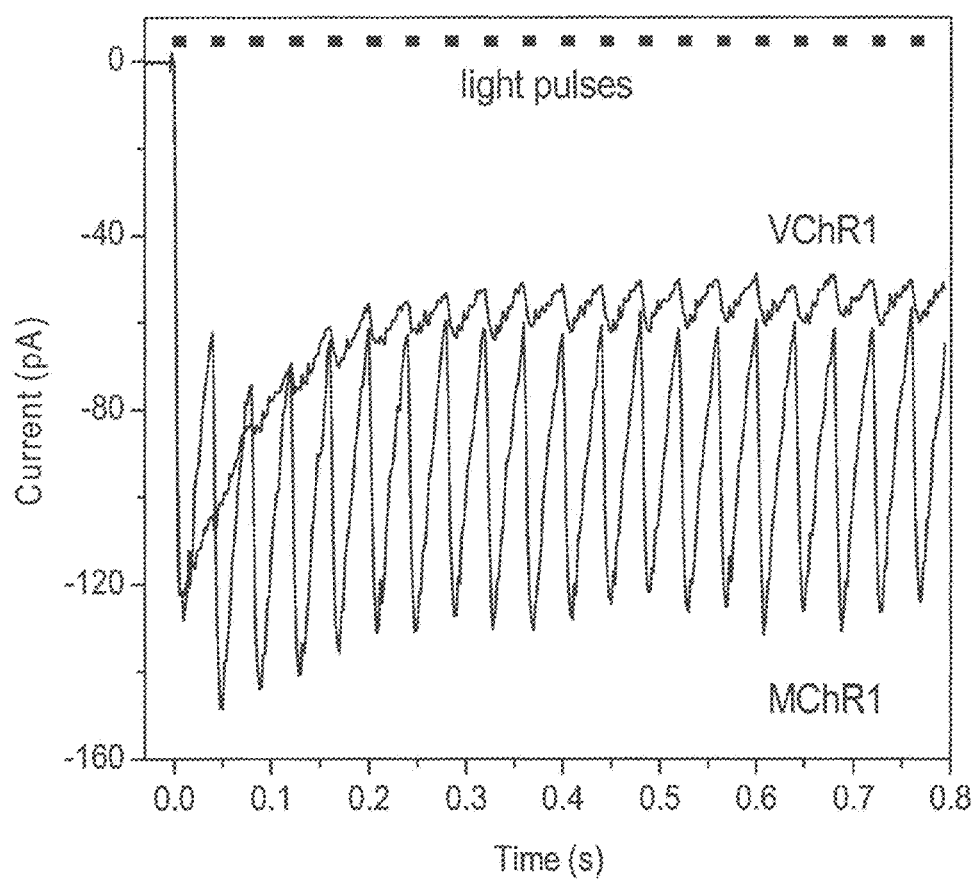
FIG. 15 illustrates photoresponses generated by MChR1 from *M. viride* and VChR1 from *V. carteri* expressed in HEK293 cells upon 25 Hz stimulation with 530 nm light.
Figure 16:
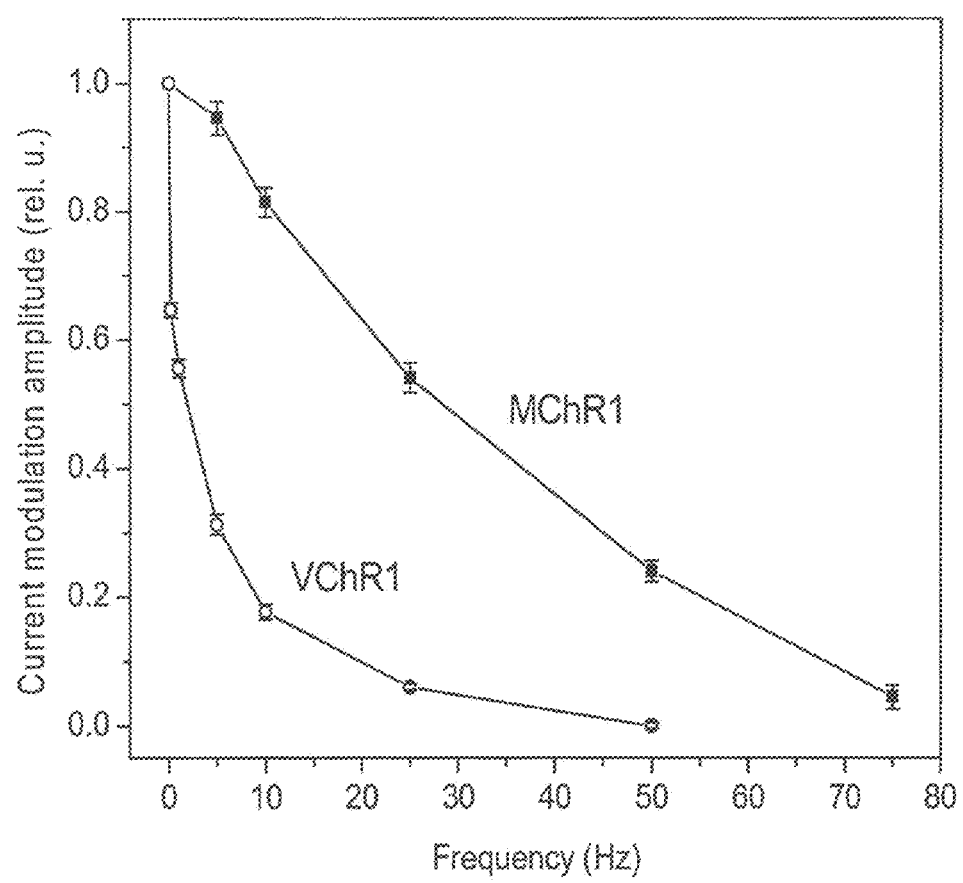
FIG. 16 illustrates the dependence of the amplitude modulation on the stimulus frequency for MChR1 from *M. viride* (filled squares) and VChR1 from *V. carteri* (open circles). Data are the mean values±SEM of 8 successive frequency changes in opposite direction.

The utility of MChR1 and VChR1 for neurologic applications was established by measuring their responses to high-frequency stimulation in mammalian HEK cells. At 25 Hz stimulus frequency the photocurrent generated by MChR1 was modulated to at least 50% amplitude, whereas that generated by VChR1 showed practically no modulation (as demonstrated in FIG. 15). The much higher degree of amplitude modulation in MChR1, as compared to VChR1, derives not only from the faster current decay, but also from the significantly less inactivation of the photocurrent by a series of light pulses (as demonstrated in FIG. 15). Consequently, at the level of 50% amplitude modulation MChR1 demonstrated ~15-fold better frequency response than VChR1 (as demonstrated in FIG. 16). In native cells, the faster photocycle of MChR1, as compared to VChR1, is better adapted for the higher rotation frequency of the unicellular *M. viride* than that of colonial *V. carteri*.

The MChR1 sequence significantly expands channelrhodopsin diversity, as it deviates from other known channelrhodopsins in several important aspects, which refines the sequence criteria for light-gated channel activity.

Sequence analysis of the previously known four channelrhodopsin homologs identified an array of five Glu residues in the predicted second transmembrane helix as a conserved structural feature suggested to contribute to forming a water-containing channel. This hypothesis was tested by analysis of ChR2 mutants in which each individual Glu residue was replaced by Ala.

Photocurrents generated by all these mutants were affected in either amplitude, kinetics, or inactivation, confirming their involvement in channel function in ChR2. However, while the use of the current methods and compositions should not be limited by any particular theory, results indicate that two of these Glu residues (corresponding to E83 and E97 in the ChR2 sequence) are not required for channel activity at least in some channelrhodopsins, because (a) in MChR1, which behaves as a typical channelrhodopsin in HEK cells, they are replaced by non-carboxylated residues; and (b) their introduction in MChR1 actually inhibited photocurrents. Similarly, it has been suggested from analysis of the four previously known channelrhodopsins that the presence of a His residue at the position of the proton donor (D95 in BR) may be functionally important. MChR1 lacks this feature since it contains Ala at this position, but substitution by His or Arg at this site each led to suppression of channel activity. This amino acid position may be significant but the presence of His at this site is not required for channelrhodopsin functionality. On the other hand, residues that form the predicted hydrogen-bond between putative helices C and D (C128 and D156 according to ChR2 numbering) are conserved in MChR1. MChR1 lacks a Glu residue at the position of E87 in ChR1, and its spectral sensitivity is independent of external pH.

Photocurrents generated by CaChR1 and CyChR1 differ from that of ChR1 in their kinetics, inactivation and light dependence. The dependence of the spectral sensitivity of CaChR1- and CyChR1-generated currents on the external pH are consistent with the role of the residue in the position of Glu87 (ChR1 numbering) in color tuning, as both these proteins also contain a Glu residue in this position (Glu94 and Glu95, respectively). In contrast, MChR1, which contains a non-carboxylated residue in this position, does not show the spectral shift over the entire tested pH range from 5.3 to 9. This residue was suggested to contribute to the formation of a trimodal counterion of the protonated Schiff base characteristic of ChR1-like channelrhodopsins in contrast to ChR2-like ones. Therefore, protonation/deprotonation of this residue would be anticipated to alter the chromophore polarity and change the absorption spectrum. Interestingly, in both CaChR1 and CyChR1 the spectral transition occurs at a pH several units higher than that in ChR1. Moreover, CaChR1 and CyChR1 differ from the earlier known ChR1 in that the spectral maxima of their protonated forms is at 520 nm, compared to 497 nm of ChR1. The red-shifted spectrum of VChR1, peaking at 530 nm, has been attributed to the residues in the positions of Ser141 and Ala215 (BR numbering), which differentiates this protein from all other known channelrhodopsins. However, both CaChR1 and CyChR1 contain Gly and Ser, respectively, in these positions, as do all other known channelopsins except VChR1, i.e., their red-shifted spectral sensitivity must be due to other structural reasons. This result suggests the involvement of additional structural factors defining the pH dependence of the spectral sensitivity.

Comparative sequence analysis reveals that both CaChR1 and CyChR1 differ from ChR1 and, in fact, from all other reported channelrhodopsins, in the residues found in the positions of Glu194 and Glu204 (BR numbering). Glu194 is conserved in all prior reported channelopsins, except CaChR1 and CyChR1, in which it is replaced by Ser. Conversely, the position of Glu204 is occupied by Ser in all previously described channelopsins, but it is Asp in CaChR1 and CyChR1. In BR, Glu194 and Glu204 are part of the extracellular hydrogen-bonded network that forms the proton release pathway and are known to contribute to the pH dependence of spectral transitions. These residues may also play a role in regulation of the pH dependence and/or color tuning in channelrhodopsins. Replacement of Ser with Glu at the site corresponding to Glu204 in BR led to the total abolishment of channel activity in MChR1, suggesting the importance of this site for channelrhodopsin function.

One of the major challenges for optogenetic applications, especially in living animals, are scattering of the stimulating light by biological tissues and its absorption by hemoglobin. Optogenetic tools with long-wavelength absorption would exhibit minimal light attenuation from these effects, but most microbial rhodopsins do not fall into this category. For instance, the absorption maximum of ChR2, which possesses several other useful properties and is thereby most frequently used as a depolarizing tool in optogenetics, is 470 nm. Several approaches have been taken to attempt to acquire red-shifted variants to reduce the light-attenuation by scatter and absorption in tissue: (i) searching for natural red-shifted channelrhodopsin variants in different algae (such as those described herein); (ii) chimera construction; and (iii) site-directed mutagenesis. All of these approaches have in common modification of the apoprotein, and all have proved somewhat successful, although in some cases a desired spectral shift was accompanied by negative effects such as slowing down of the current kinetics, or a decrease in the current amplitude.

Long-wavelength absorption by optogenetic tools is desirable to increase the penetration depth of the stimulus light by minimizing tissue scattering and absorption by hemoglobin. In some embodiments, the long-wavelength sensitivity of optogenetic microbial rhodopsins is enhanced using 3,4-Dehydroretinal (A2 retinal). A2 retinal (3,4-dehydroretinal) is a natural retinoid, its 11-cis form being found in photoreceptor cells of certain invertebrates, fish and amphibians, where it may constitute the only retinal, or an additional chromophore to A1 retinal. The presence of an additional double bond in the β-ionone ring of the chromophore results in pigments that absorb light at longer wavelengths, as compared to those formed with A1 (regular) retinal. Variations in A1/A2 ratio cause natural adaptive tuning of spectral sensitivity of vision in the organisms during adaptation to external conditions. Reconstitution of bleached microbial rhodopsins (bacteriorhodopsin, halorhodopsin, sensory rhodopsins I and II) in vitro with all-trans A2 retinal also shifts their absorption spectra to longer wavelengths. In some embodiments, spectral properties of optogenetic tools were modified by incorporation of all-trans A2 retinal. The addition of A2 retinal, both ion pumps and channelrhodopsins form functional pigments with significantly red-shifted absorption. Despite the presence of residual endogenous A1 retinal in HEK293 cells, large extension of spectral sensitivity to longer wavelengths was observed.

In the examples below it is shown that A2 retinal reconstitutes a fully functional archaerhodopsin-3 (AR-3) proton pump and four channelrhodopsin variants (CrChR1, CrChR2, CaChR1 and MvChR1). Substitution of A1 by A2 retinal significantly shifted the spectral sensitivity of all tested rhodopsins to longer wavelengths without altering other aspects of their function. The spectral shift upon substitution of A1 by A2 in AR-3 was ~1,000 cm$^{-1}$, close to that of other long-wavelength microbial rhodopsins. Notably, in all tested channelrhodopsins the shifts were 1.4-1.8-fold larger than in other microbial or visual rhodopsins. In the case of CrChR1, binding of A2 retinal raised the pKa of a spectral-tuning carboxylate residue, which contributed to the overall spectral shift.

In some embodiments, the long-wavelength sensitivity of optogenetic microbial rhodopsins is enhanced using 3,4-Dehydroretinal (A2 retinal).

In some embodiments, chromophore substitution provides a complementary strategy to improve the efficiency of optogenetic tools. A2 retinal reconstitutes a fully functional archaerhodopsin-3 (AR-3) proton pump and four channelrhodopsin variants (CrChR1, CrChR2, CaChR1 and MvChR1). Substitution of A1 by A2 retinal significantly shifted the spectral sensitivity of all tested rhodopsins to longer wavelengths without altering other aspects of their function. The spectral shift upon substitution of A1 by A2 in AR-3 was ~1,000 cm$^{-1}$, close to that of other long-wavelength microbial rhodopsins. Notably, in all tested channelrhodopsins the shifts were 1.4-1.8-fold larger than in other microbial or visual rhodopsins. In the case of CrChR1, binding of A2 retinal raised the pKa of a spectral-tuning carboxylate residue, which contributed to the overall spectral shift.

Channelrhodopsin Amino Acid Sequences:

The peptide amino acid sequences that can be used in various embodiments including the channelrhodopsin amino acid sequences described herein (SEQ ID NOS.: 1-4, 6, 8 and 10), as well as analogues and derivatives thereof and functional fragments such as but not limited to the type 1 rhodopsin domain. In fact, in some embodiments the any desired peptide amino acid sequences encoded by particular nucleotide sequences can be used, as is the use of any polynucleotide sequences encoding all, or any portion, of desired peptide amino acid sequences. The degenerate nature of the genetic code is well-known, and, accordingly, each channelrhodopsin peptide amino acid-encoding nucleotide sequence is generically representative of the well-known nucleic acid "triplet" codon, or in many cases codons, that can encode the amino acid. As such, as contemplated herein, the channelrhodopsin peptide amino acid sequences described herein, when taken together with the genetic code (see, e.g., "Molecular Cell Biology," Table 4-1 at page 109 (Darnell et al., eds., W. H. Freeman & Company, New York, N.Y., 1986)), are generically representative of all the various permutations and combinations of nucleic acid sequences that can encode such amino acid sequences.

Such functionally equivalent peptide amino acid sequences (conservative substitutions) include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Conservative amino acid substitutions may alternatively be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5). The use of the hydropathic amino acid index in conferring interactive biological function on a protein is understood in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other embodiments amino acid substitutions that are within ±1 are included, and in yet other embodiments amino acid substitutions within ±0.5 are included.

Conservative amino acid substitutions may alternatively be made on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5) and tryptophan (-3.4). In making changes based upon similar hydrophilicity values, in certain embodiments the substitution of amino acids whose hydrophilicity values are within ±2 is included, in certain embodiments those that are within ±1 are included, and in certain embodiments those within ±0.5 are included.

Fusion Proteins:

The use of fusion proteins in which a polypeptide or peptide, or a truncated or mutant version of peptide is fused to an unrelated protein, polypeptide, or peptide, and can be designed on the basis of the desired peptide encoding nucleic acid and/or amino acid sequences described herein. Such fusion proteins include, but are not limited to: IgFc fusions, which stabilize proteins or peptides and prolong half-life in vivo; fusions to any amino acid sequence that allows the fusion protein to be anchored to the cell membrane; or fusions to an enzyme, fluorescent protein, or luminescent protein that provides a marker function.

In certain embodiments, a fusion protein may be readily purified by utilizing an antibody that selectively binds to the fusion protein being expressed. In alternate embodiments, a fusion protein may be purified by subcloning peptide encoding nucleic acid sequence into a recombination plasmid, or a portion thereof, is translationally fused to an amino-terminal (N-terminal) or carboxy-terminal (C-terminal) tag consisting of six histidine residues (a "His-tag"; see, e.g., Janknecht et al., Proc. Natl. Acad. Sci. USA 88:8972-8976, 1991). Extracts from cells expressing such a construct are loaded onto Ni$^{2+}$ nitriloacetic acid-agarose columns, and histidine-tagged proteins are selectively eluted with imidazole-containing buffers.

Recombinant Expression:

While the desired peptide amino acid sequences described can be chemically synthesized (see, e.g., "Proteins: Structures and Molecular Principles" (Creighton, ed., W. H. Freeman & Company, New York, N.Y., 1984)), large polypeptides sequences may advantageously be produced by recombinant DNA technology using techniques well-known in the art for expressing nucleic acids containing a nucleic acid sequence that encodes the desired peptide. Such methods can be used to construct expression vectors containing peptide encoding nucleotide sequences and appropriate transcriptional and translational control signals. These methods include, for example, in vitro recombinant DNA techniques, synthetic techniques, and in vivo genetic recombination (see, e.g., "Molecular Cloning, A Laboratory Manual," supra, and "Current Protocols in Molecular Biology," supra). Alternatively, RNA and/or DNA encoding desired peptide encoding nucleotide sequences may be chemically synthesized using, for example, synthesizers (see, e.g., "Oligonucleotide Synthesis: A Practical Approach" (Gait, ed., IRL Press, Oxford, United Kingdom, 1984)).

A variety of host-expression vector systems may be utilized to express peptide encoding nucleotide sequences. When the desired peptide or polypeptide is soluble or a soluble derivative, the peptide or polypeptide can be recovered from the host cell culture, i.e., from the host cell in cases where the peptide or polypeptide is not secreted, and from the culture media in cases where the peptide or polypeptide is secreted by the host cell. However, suitable expression systems also encompass engineered host cells that express the desired polypeptide or functional equivalents anchored in the cell membrane. Purification or enrichment of the desired peptide from such expression systems can be accomplished using appropriate detergents and lipid micelles, and methods well-known to those skilled in the art. Furthermore, such engineered host cells themselves may be used in situations where it is desired not only to retain the structural and functional characteristics of the peptide, but to assess biological activity, e.g., in certain drug screening assays.

In certain applications, transient expression systems are desired. However, for long-term, high-yield production of recombinant proteins or peptides, stable expression is generally preferred. For example, cell lines that stably express the desired protein, polypeptide, peptide, or fusion protein may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for about 1-2 days in an enriched media, and then switched to a selective media. The selectable marker in the recombinant plasmid confers resistance to the selection, and allows cells to stably integrate the plasmid into their chromosomes and grow to form foci, which in turn can be cloned and expanded into cell lines. This method may advantageously be used to engineer cell lines that express the desired gene products or portions thereof. Such engineered cell lines may be particularly useful in screening and evaluation of compounds that affect the endogenous activity of a desired protein, polypeptide or peptide.

A number of selection systems may be used, including, but not limited to, the herpes simplex virus thymidine kinase (Wigler et al., *Cell* 11:223-232, 1977), hypoxanthine-guanine phosphoribosyltransferase (Szybalska and Szybalski, *Proc. Natl. Acad. Sci. USA* 48:2026-2034, 1962), and adenine phosphoribosyltransferase (Lowy et al., *Cell* 22:817-823, 1980) genes, which can be employed in tk⁻, hgprt⁻ or aprt⁻ cells, respectively. Anti-metabolite resistance can also be used as the basis of selection for the following genes: dihydrofolate reductase (dhfr), which confers resistance to methotrexate (Wigler et al., *Proc. Natl. Acad. Sci. USA* 77:3567-3570, 1980, and O'Hare et al., *Proc. Natl. Acad. Sci. USA* 78:1527-1531, 1981); guanine phosphoribosyl transferase (gpt), which confers resistance to mycophenolic acid (Mulligan and Berg, *Proc. Natl. Acad. Sci. USA* 78:2072-2076, 1981); neomycin phosphotransferase (neo), which confers resistance to the aminoglycoside G-418 (Colbere-Garapin et al., *J. Mol. Biol.* 150:1-14, 1981); and hygromycin B phosphotransferase (hpt), which confers resistance to hygromycin (Santerre et al., *Gene* 30:147-156, 1984).

Host cells/expression systems that may be used for purpose of providing compositions to be used in the disclosed methods include, but are not limited to, microorganisms such as bacteria (e.g., *E. coli, B. subtilis*) transformed with a recombinant bacteriophage DNA, plasmid DNA, or cosmid DNA expression vector containing a desired peptide encoding nucleotide sequence; yeast (e.g., *Saccharomyces cerevisiae, Pichia pastoris*) transformed with a recombinant yeast expression vector containing a desired peptide encoding nucleotide sequence; insect cell systems infected with a recombinant virus expression vector (e.g., baculovirus) containing a desired peptide encoding nucleotide sequence; plant cell systems infected with a recombinant virus expression vector (e.g., cauliflower mosaic virus, CaMV; tobacco mosaic virus, TMV), or transformed with a recombinant plasmid expression vector (e.g., Ti plasmid), containing a desired peptide encoding nucleotide sequence; or mammalian cell systems (e.g., COS, CHO, BHK, 293, 3T3) harboring a recombinant expression construct containing a desired peptide encoding nucleotide sequence and a promoter derived from the genome of mammalian cells (e.g., metallothionein promoter) or from mammalian viruses (e.g., the adenovirus late promoter, the vaccinia virus 7.5K promoter).

In bacterial systems, a number of different expression vectors may be advantageously selected depending upon the use intended for the desired gene product being expressed. For example, when a large quantity of such a protein is to be produced, such as for the generation of pharmaceutical compositions comprising a desired peptide, or for raising antibodies to the protein, vectors that direct the expression of high levels of fusion protein products that are readily purified may be desirable. Such vectors include, but are not limited to: the *E. coli* expression vector pUR278 (Ruther and Müller-Hill, *EMBO J.* 2:1791-1794, 1983), in which a desired peptide encoding sequence may be ligated individually into the vector in frame with the lacZ coding region so that a fusion protein is produced; pIN vectors (Inouye and Inouye, *Nucleic Acids Res.* 13:3101-3110, 1985, and Van Heeke and Schuster, *J. Biol. Chem.* 264:5503-5509, 1989); and the like. pGEX vectors (GE Healthcare, Piscataway, N.J.) may also be used to express a desired peptide moiety as a fusion protein with glutathione S-transferase (GST). In general, such fusion proteins are soluble and can easily be purified from lysed cells by adsorption to glutathione-agarose beads, followed by elution in the presence of free glutathione. The pGEX vectors are designed to include thrombin or factor Xa protease cleavage sites so that the cloned desired peptide encoding gene product can be released from the GST moiety.

In an exemplary insect system, *Autographa californica* nuclear polyhedrosis virus (AcNPV) is used as a vector to express a desired peptide encoding sequence. The virus grows in *Spodoptera frugiperda* cells. A desired peptide encoding sequence may be cloned individually into a non-essential region (for example the polyhedrin gene) of the virus, and placed under control of an AcNPV promoter (for example the polyhedrin promoter). Successful insertion of a desired peptide encoding sequence will result in inactivation of the polyhedrin gene and production of non-occluded recombinant virus (i.e., virus lacking the proteinaceous coat coded for by the polyhedrin gene). The recombinant viruses are then used to infect *Spodoptera frugiperda* cells in which the inserted polynucleotide is expressed (see, e.g., Smith et al., *J. Virol.* 46:584-593, 1983, and U.S. Pat. No. 4,215,051).

In mammalian host cells, a number of viral-based expression systems may be utilized. In cases where an adenovirus is used as an expression vector, a desired peptide encoding nucleotide sequence may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing desired peptide products in infected hosts (see, e.g., Logan and Shenk, *Proc. Natl. Acad. Sci. USA* 81:3655-3659, 1984). Specific initiation signals may also be required for efficient translation of inserted desired peptide encoding nucleotide sequences. These signals include the ATG initiation codon and adjacent sequences. In some cases exogenous translational control signals, including, perhaps, the ATG initiation codon, may be provided. Furthermore, the initiation codon should be in phase with the reading frame of the desired peptide encoding coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Nevins, *CRC Crit. Rev. Biochem.* 19:307-322, 1986).

In yeast, a number of vectors containing constitutive or inducible promoters may be used. For a review, see, e.g., "Current Protocols in Molecular Biology," supra, Ch. 13, Bitter et al., *Meth. Enzymol.* 153:516-544, 1987, "DNA Cloning," Vol. II, Ch. 3 (Glover, ed., IRL Press, Washington, D.C., 1986); Bitter, *Meth. Enzymol.* 152:673-684, 1987, "The Molecular Biology of the Yeast *Saccharomyces*: Life Cycle and Inheritance" (Strathern et al., eds., Cold Spring Harbor Press, Cold Spring Harbor, N.Y., 1981), and "The Molecular Biology of the Yeast *Saccharomyces*: Metabolism and Gene Expression" (Strathern et al., eds., Cold Spring Harbor Press, Cold Spring Harbor, N.Y., 1982).

In plants, a variety of different plant expression vectors can be used, and expression of a desired peptide encoding sequence may be driven by any of a number of promoters. For example, viral promoters such as the 35S RNA or 19S RNA promoters of CaMV (Brisson et al., *Nature* 310:511-514, 1984), or the coat protein promoter of TMV (Takamatsu et al., *EMBO J.* 6:307-311, 1987) may be used. Alternatively, plant promoters such as the promoter of the small subunit of RUBISCO (Coruzzi et al., *EMBO J.* 3:1671-1679, 1984, and Broglie et al., *Science* 224:838-843, 1984), or heat shock promoters, e.g., soybean hsp17.5-E or hsp17.3-B (Gurley et al., *Mol. Cell. Biol.* 6:559-565, 1986) may be used. These constructs can be introduced into plant cells using, for example, Ti plasmids, Ri plasmids, plant virus vectors, direct DNA transformation, microinjection, or electroporation. For reviews of such techniques, see, e.g., Weissbach and Weissbach, in "Methods in Plant Molecular Biology," Section VIII (Schuler and Zielinski, eds., Academic Press, Inc., New York, N.Y., 1988), and "Plant Molecular Biology," $2^{nd}$ Ed., Ch. 7-9 (Grierson and Covey, eds., Blackie & Son, Ltd., Glasgow, Scotland, United Kingdom, 1988).

In addition, a host cell strain may be chosen that modulates the expression of the inserted desired peptide encoding sequence, or modifies and processes the desired peptide encoding nucleic acid sequence in a desired fashion. Such modifications (e.g., glycosylation) and processing (e.g., cleavage) of protein products may affect certain functions of the protein. Different host cells have characteristic and specific mechanisms for post-translational processing and modification of proteins and peptides. Appropriate cell lines or host systems can be chosen to ensure the correct or desired modification and processing of the desired protein, polypeptide, or peptide expressed. To this end, eukaryotic host cells that possess the cellular machinery for desired processing of the primary transcript, and glycosylation and/or phosphorylation of desired peptide encoding nucleic acid sequence be used. Such mammalian host cells include, but are not limited to, Chinese hamster ovary (CHO), VERO, baby hamster kidney (BHK), HeLa, monkey kidney (COS), MDCK, 293, 3T3, WI38, human hepatocellular carcinoma (e.g., Hep G2), and U937 cells.

Compositions as Therapeutics:

The use of channelrhodopsins, or active fragments thereof such as but not limited to the type 1 rhodopsin domain as therapeutics. In certain embodiments the presently disclosed compositions and are used to improve optogenetic techniques and applications as well as can be used to aid in diagnosis, prevention, and/or treatment of among other things neuron mediated disorders, neurologic disorders (such as Parkinson's disease) and as therapy for ocular disorders.

In certain embodiments the presently disclosed compositions can be administered in combination with one or more additional compounds or agents ("additional active agents") for the treatment, management, and/or prevention of among other things neuron mediated disorders, neurologic disorders (such as Parkinson's disease) and as therapy for ocular disorders. Such therapies can be administered to a patient at therapeutically effective doses to treat or ameliorate, among other things, neuron mediated disorders, neurologic disorders (such as Parkinson's disease) and as therapy for ocular disorders. A therapeutically effective dose refers to that amount of the compound sufficient to result in any delay in onset, amelioration, or retardation of disease symptoms.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, expressed as the ratio $LD_{50}/ED_{50}$. Compositions that exhibit large therapeutic indices are preferred. Compounds that exhibit toxic side effects may be used in certain embodiments, however, care should usually be taken to design delivery systems that target such compositions preferentially to the site of affected tissue, in order to minimize potential damage to uninfected cells and, thereby, reduce side effects.

Data obtained from cell culture assays and animal studies can be used in formulating a range of dosages for use in humans. The dosages of such compositions lie preferably within a range of circulating concentrations that include the $ED_{50}$ with little or no toxicity. The dosage may vary within this range depending on the dosage form employed and the route of administration utilized. For any composition, the therapeutically effective dose can be estimated initially from cell culture assays. A dose may be formulated in animal models to achieve a circulating plasma concentration range that includes the $IC_{50}$ (i.e., the concentration of the test composition that achieves a half-maximal inhibition of symptoms) as determined in cell culture. Such information can be used to more accurately determine useful doses in humans. Plasma levels may be measured, for example, by high performance liquid chromatography.

When the therapeutic treatment of among other things neurologic disorders (such as Parkinson's disease) and as therapy for ocular disorders is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies help establish safe doses.

Additionally, the bioactive agent may be coupled or complexed with a variety of well established compositions or structures that, for instance, enhance the stability of the bioactive agent, or otherwise enhance its pharmacological properties (e.g., increase in vivo half-life, reduce toxicity, etc.).

Such therapeutic agents can be administered by any number of methods known to those of ordinary skill in the art including, but not limited to, inhalation, subcutaneous (sub-q), intravenous (I.V.), intraperitoneal (I.P.), intramuscular (I.M.), or intrathecal injection, or topically applied (transderm, ointments, creams, salves, eye drops, and the like), as described in greater detail below.

Pharmaceutical Compositions:

Pharmaceutical compositions for use in accordance with the presently described compositions may be formulated in conventional manners using one or more physiologically acceptable carriers or excipients.

The pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to: amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences," 18$^{th}$ Ed. (Gennaro, ed., Mack Publishing Company, Easton, Pa., 1990)).

Additionally, the described therapeutic peptides can be linked to a half-life extending vehicle. Certain exemplary half-life extending vehicles are known in the art, and include, but are not limited to, the Fc domain, polyethylene glycol, and dextran (see, e.g., PCT Patent Application Publication No. WO 99/25044).

These agents may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The agents may also be formulated as compositions for rectal administration such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. For example, agents may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Active compositions can be administered by controlled release means or by delivery devices that are well-known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Exemplary sustained release matrices include, but are not limited to, polyesters, hydrogels, polylactides (see, e.g., U.S. Pat. No. 3,773,919 and European Patent Application Publication No. EP 058,481), copolymers of L-glutamic acid and gamma ethyl-L-glutamate (see, e.g., Sidman et al., *Biopolymers* 22:547-556, 1983), poly(2-hydroxyethyl-methacrylate) (see, e.g., Langer et al., *J. Biomed. Mater. Res.* 15:167-277, 1981, and Langer, *Chemtech* 12:98-105, 1982), ethylene vinyl acetate (Langer et al., supra), and poly-D(–)-3-hydroxybutyric acid (European Patent Application Publication No. EP 133,988). Sustained release compositions may include liposomes, which can be prepared by any of several methods known in the art (see, e.g., Eppstein et al., *Proc. Natl. Acad. Sci. USA* 82:3688-3692, 1985, and European Patent Application Publication Nos. EP 036,676, EP 088, 046, and EP 143,949). Suitable controlled-release formulations known to those of ordinary skill in the art, including those described herein, can be readily selected for use with the presently disclosed compositions. Certain embodiments encompass single unit dosage forms suitable for oral administration such as, but not limited to, tablets, capsules, gelcaps, and caplets that are adapted for controlled-release.

All controlled-release pharmaceutical products have a common goal of improving therapy over that achieved by their non-controlled counterparts. Ideally, use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of active ingredient that promptly produces the desired therapeutic effect, and gradually and continually release other amounts of active ingredient to maintain this level of therapeutic or prophylactic effect over an extended period of time. In order to maintain this relatively constant level of active ingredient in the body, the drug must be released from the dosage form at a rate that will replace the amount of active ingredient being metabolized and excreted from the body. Controlled-release of an active ingredient can be stimulated by various conditions including, but not limited to, pH, temperature, enzymes, water, or other physiological conditions or compositions.

In some cases, active ingredients of the disclosed methods and compositions are preferably not administered to a patient at the same time or by the same route of administration. Therefore, in some embodiments are kits that, when used by the medical practitioner, can simplify the administration of appropriate amounts of active ingredients to a patient.

A typical kit comprises a single unit dosage form of one or more of the therapeutic agents disclosed, alone or in combination with a single unit dosage form of another agent that may be used in combination with the disclosed compositions. Disclosed kits can further comprise devices that are used to administer the active ingredients. Examples of such devices include, but are not limited to, syringes, drip bags, patches, and inhalers.

Disclosed kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the disclosed formulations do not contain any alcohols or other co-solvents, oils or proteins.

Channelrhodopsin Nucleic Acid Sequences:

Channelrhodopsin nucleic acid sequences for use in the disclosed methods and compositions include, but are not limited to, the active portion of the presently disclosed algal derived red-shifted channelrhodopsins (SEQ ID NOS: 5, 7 and 9), including but not limited to those described, such as but not limited to the nucleic acid sequences that encode the type 1 rhodopsin domain, an active portion of the presently disclosed algal derived red-shifted channelrhodopsins, such as but not limited to the type 1 or rhodopsin domains disclosed (SEQ ID NOS: 1, 2, 3 or 4)

In some embodiments, the use of an active portion of a presently disclosed algal derived red-shifted channelrhodopsin, such as but not limited to the type 1 rhodopsin domain, includes all or portions of the sequences described herein (and expression vectors comprising the same), and additionally contemplates the use of any nucleotide sequence encoding a contiguous an active portion of the presently disclosed algal derived red-shifted channelrhodopsins, such as but not limited to the type 1 rhodopsin domain, open reading frame (ORF) that hybridizes to a complement of a channelrhodopsin or channelopsin sequence described herein under highly stringent conditions, e.g., hybridization to filter-bound DNA in 0.5 M NaHPO$_4$, 7% sodium dodecyl sulfate (SDS), 1 mM EDTA at 65EC, and washing in 0.1×SSC/0.1% SDS at 68EC ("Current Protocols in Molecular Biology," Vol. 1 and 2 (Ausubel et al., eds., Green Publishing Associates, Incorporated, and John Wiley & Sons, Incorporated, New York, N.Y., 1989)), and encodes a functionally equivalent channelrhodopsin (or active portion thereof, such as but not limited to the type 1 rhodopsin domain) gene product or the active portion thereof. Additionally contemplated is the use of any nucleotide sequence that hybridizes to the complement of a DNA sequence that encodes a channelrhodopsin amino acid sequence under moderately stringent conditions, e.g., washing in 0.2×SSC/0.1% SDS at 42EC ("Current Protocols in Molecular Biology," supra), yet still encodes a functionally equivalent channelrhodopsin product. Functional equivalents of channelrhodopsin include, but are not limited to, naturally occurring versions of channelrhodopsin present in other species (orthologs and homologs), and mutant versions of channelrhodopsin, whether naturally occurring or engineered (by site directed mutagenesis, gene shuffling, or directed evolution, as described in, for example, U.S. Pat. No. 5,837,458) or active portion thereof, such as but not limited to the type 1 rhodopsin domain. The disclosure also includes the use of degenerate nucleic acid variants (due to the redundancy of the genetic code) of the identified channelrhodopsin polynucleotide sequences.

Additionally contemplated is the use of polynucleotides encoding channelrhodopsin ORFs, or their functional equivalents, encoded by polynucleotide sequences that are about 99, 95, 90, or about 85 percent similar to the corresponding regions of the an algae derived channelrhodopsin sequences described herein (as measured by BLAST sequence comparison analysis using, for example, the University of Wisconsin GCG sequence analysis package (SEQUENCHER 3.0, Gene Codes Corporation, Ann Arbor, Mich.) using default parameters).

Transgenic Animals:

The present disclosure provides methods and compositions for the creation and use of both human and non-human transgenic animals that carry an algae derived channelrhodopsin transgene in all their cells, as well as non-human transgenic animals that carry an algae derived channelrhodopsin transgene in some, but not all their cells, for example in certain neuronal cells. Human and non-human mammals of any species, including, but not limited to, mice, rats, rabbits, guinea pigs, pigs, micro-pigs, goats, and non-human primates, e.g., baboons, monkeys, and chimpanzees, can be used to generate transgenic animals carrying an algae derived channelrhodopsin polynucleotide (and/or expressing an algae derived polypeptide) may be integrated as a single transgene or in concatamers, e.g., head-to-head or head-to-tail tandems. An algae derived channelrhodopsin transgene may also be selectively introduced into and activated in a particular cell-type (see, e.g., Lakso et al., *Proc. Natl. Acad. Sci. USA* 89:6232-6236, 1992). The regulatory sequences required for such a cell-type specific activation will depend upon the particular cell-type of interest, and will be apparent to those of skill in the art.

Should it be desired that an algae derived channelrhodopsin, or fragment thereof, transgene be integrated into the chromosomal site of the endogenous copy of the mammalian channelrhodopsin gene, gene targeting is generally preferred. Briefly, when such a technique is to be utilized, vectors containing some nucleotide sequences homologous to the endogenous channelrhodopsin gene are designed for the purpose of integrating, via homologous recombination with chromosomal sequences, into and disrupting the function of the endogenous channelrhodopsin gene (i.e., "knockout" animals). In this way, the expression of the endogenous channelrhodopsin gene may also be eliminated by inserting non-functional sequences into the endogenous channelrhodopsin gene. The transgene may also be selectively introduced into a particular cell-type, thus inactivating the endogenous channelrhodopsin gene in only that cell-type (see, e.g., Gu et al., *Science* 265:103-106, 1994). The regulatory sequences required for such a cell-type specific inactivation will depend upon the particular cell-type of interest, and will be apparent to those of skill in the art.

Any technique known in the art may be used to introduce a channelrhodopsin, or fragment thereof, transgene into animals to produce the founder lines of transgenic animals. Such techniques include, but are not limited to: pronuclear microinjection (U.S. Pat. No. 4,873,191); retrovirus-mediated gene transfer into germ lines (van der Putten et al., *Proc. Natl. Acad. Sci. USA* 82:6148-6152, 1985); gene targeting in embryonic stem cells (Thompson et al., *Cell* 56:313-321, 1989); electroporation of embryos (Lo, *Mol. Cell. Biol.* 3:1803-1814, 1983); sperm-mediated gene transfer (Lavitrano et al., *Cell* 57:717-723, 1989); and positive-negative selection, as described in U.S. Pat. No. 5,464,764. For a review of such techniques, see, e.g., Gordon, *Int. Rev. Cytol.* 115:171-229, 1989.

Once transgenic animals have been generated, the expression of the recombinant channelrhodopsin gene, or fragment thereof, may be assayed utilizing standard techniques. Initial screening may be accomplished by Southern blot analysis or PCR techniques to analyze animal tissues to assay whether integration of the channelrhodopsin transgene has taken place. The level of mRNA expression of the channelrhodopsin transgene in the tissues of the transgenic animals may also be assessed using techniques that include, but are not limited to, Northern blot analysis of cell-type samples obtained from the animal, in situ hybridization analysis, and RT-PCR. Samples of an algae derived channelrhodopsin-expressing tissue can also be evaluated immunocytochemically using antibodies selective for the channelrhodopsin transgene product.

In certain embodiments, the invention concerns isolated nucleic acid segments and recombinant vectors which encode a protein or peptide that includes within its amino acid sequence an amino acid sequence of a channelrhodopsin or a functional portions or variant thereof, such as those identified and cloned: MChR1 (SEQ ID NO: 1), CaChR1 (SEQ ID NO: 2), CyChR1 (SEQ ID NO: 3) and CraChR2 (SEQ ID NO: 4). In some embodiments, a portion of a channelrhodopsin and has relatively few amino acids which are not identical to, or a biologically functional equivalent of, the amino acids of the full-length channelrhodopsin. The term "functional equivalent" is well understood in the art. Accordingly, sequences which have between about 70% and about 80%; or more preferably, between about 85% and about 90%; or even more preferably, between about 90 and 95% and about 99%; of amino acids which are identical or functionally equivalent to the amino acids of the identified and cloned: MChR1 (SEQ ID NO: 1), CaChR1 (SEQ ID NO: 2), CyChR1 (SEQ ID NO: 3) or CraChR2 (SEQ ID NO:-4) will be sequences which are essentially as set forth in SEQ ID NOS: 1-4.

The nucleic acid segments of the present invention, regardless of the length of the coding sequence itself, may be combined with other sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to nucleic acids that encode the polypeptides of SEQ ID NOS: 1-4, such as about 10 to 15 or 20, 30, or 40 or so nucleotides, and which are up to 2000 or so base pairs in length. DNA segments with total lengths of about 8000, 7000, 6000, 5000, 4000, 3000, 2000, 1000, 500, 200, 100 and about 50 base pairs in length are also contemplated to be useful.

In some embodiments, isolated nucleic acids that encode the amino acids of a channelrhodopsin or fragment thereof and recombinant vectors incorporating nucleic acid sequences which encode a channelrhodopsin protein or peptide and that includes within its amino acid sequence an amino acid sequence in accordance with SEQ ID NOS: 1-4. In some embodiments, a purified nucleic acid segment that encodes a protein that encodes a channelrhodopsin or fragment thereof, the recombinant vector may be further defined as an expression vector comprising a promoter operatively linked to said channelrhodopsin-encoding nucleic acid segment.

In additional embodiments, is a host cell, made recombinant with a recombinant vector comprising channelrhodopsin-encoding nucleic acid segments. The recombinant host cell may be a prokaryotic cell or a eukaryotic cell. As used herein, the term "engineered" or "recombinant" cell is intended to refer to a cell into which a recombinant gene, such as a gene encoding a channelrhodopsin, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a copy of a genomic gene or a cDNA gene, or will include genes positioned adjacent to a promoter not naturally associated with the particular introduced gene. In some embodiments, nucleic acid molecules having sequence regions consisting of contiguous nucleotide stretches of about 14, 15-20, 30, 40, 50, or even of about 100 to about 200 nucleotides or so, identical or complementary to the channelrhodopsin-encoding nucleic acid sequences.

Transgene Based Therapies:

The nucleic acids sequences that encode an active portion of the presently disclosed red-shifted channelrhodopsins, include but are not limited to the type 1 rhodopsin domains identified in SEQ ID NOS: 1-3 or the rhodopsin domain sequences of SEQ ID NO: 4.

In certain embodiments the presently disclosed compositions and are used to improve optogenetic techniques and applications as well as can be used to aid in diagnosis, prevention, and/or treatment of neurologic disorders, such as but not limited to Parkinson's disease, as well as for ocular disorders.

In some embodiments, methods and compositions are used to identify and characterize multiple channelrhodopsins derived from algae. The cloning and expression of the type 1 rhodopsin domain of the channelrhodopsins and expression in mammalian cells demonstrates that these channelrhodopsins have improved characteristics that can be used for optogenetic applications as well as therapeutic agents.

For example, a disclosed method and composition may be used in, among other things, retinal gene therapy for mammals (as described in, among others, U.S. Pat. Nos. 5,827,702, 7,824,869 and US Patent Publication Number 20100015095 as well as in WIPO publications WO 2000/15822 and WO 1998/48097). A genetically engineered ocular cell is produced by contacting the cell with an exogenous nucleic acid under conditions in which the exogenous nucleic acid is taken up by the cell for expression. The exogenous nucleic acid is described as a retrovirus, an adenovirus, an adeno-associated virus or a plasmid. Retinal gene transfer of a reporter gene, green fluorescent protein (GFP), using a recombinant adeno-associated virus (rAAV) was demonstrated in normal primates (Bennett, J et al. 1999 *Proc. Natl. Acad. Sci. USA* 96, 9920-25). The rescue of photoreceptors using gene therapy in a model of rapid degeneration of photoreceptors using mutations of the RP65 gene and replacement therapy with the normal gene to replace or supplant the mutant gene (See, for example, US Patent Publication No. 2004/0022766) has been used to treat a naturally-occurring dog model of severe disease of retinal degenerations—the RPE65 mutant dog, which is analogous to human LCA. By expressing photosensitive membrane-channels or molecules in surviving retinal neurons of the diseased retina by viral based gene therapy method, the present invention may produce permanent treatment of the vision loss or blindness with high spatial and temporal resolution for the restored vision.

In some embodiments, introduction and expression of channelrhodopsins, such as those described herein, inocular neuronal cells, for example, impart light sensitivity to such retinas and restoring one or more aspects of visual responses and functional vision to a subject suffering from such degeneration. By restoring light sensitivity to a retina lacking this capacity, due to disease, a mechanism for the most basic light-responses that are required for vision is provided. In some embodiments, the functional domains of channelrhodopsins, such as MChR1, CaChR1, CyChR1 and CrChR2 may be used to restore light sensitivity to the retinas that have undergone rod and cone degeneration by expressing the channelrhodopsin in inner retinal neurons in vivo. In some embodiments these channelrhodopsins may be introduced using techniques that include, but are not limited to, retinal implants, cortical implants, lateral geniculate nucleus implants, or optic nerve implants In some embodiments, the red-shifted channelrhodopsins are inserted into the retinal neurons that survived after the rods and cones have died in an area or portion of the retina of a subject, using the transfer of nucleic acids, alone or within an expression vector. Such expression vectors may be constructed, for example, by introduction of the desired nucleic acid sequence into a virus system known to be of use for gene therapy applications, such as, but not limited to, AAV, retroviruses and alike.

In some embodiments the red-shifted channelrhodopsins may be inserted into retinal interneurons. These cells then can become light sensitive and send signals via the optic nerve and higher order visual pathways to the visual cortex where visual perception occurs, as has been demonstrated electrophysiologicly in mice. In some embodiments, among other routes, intravitreal and/or subretinal injections may be used to deliver channelrhodopsin molecules or virus vectors expressing the same.

In some embodiments, the active portion of the presently disclosed algal derived red-shifted channelrhodopsins, such as but not limited to the type 1 rhodopsin domain of these channelrhodopsins, can be used to restore light sensitivity to a retina, by delivering to retinal neurons a nucleic acid expression vector that encodes algal derived red-shifted channelrhodopsins (such as but not limited to the type 1 rhodopsin domain of these channelrhodopsins) that is expressible in the neurons, which vector comprises an open reading frame encoding the rhodopsin, and operatively linked thereto, a promoter sequence, and optionally, transcriptional regulatory sequences; and expressing the vector in the neurons, thereby restoring light sensitivity.

In certain embodiments the channel rhodopsin can be algal derived red-shifted channelrhodopsins such as, but not limited to functional domains of channelrhodopsins, such as MChR1, CaChR1, CyChR1 and CrChR2, or a biologically active fragment or conservative amino acid substitution variant thereof, such as but not limited to the type 1 rhodopsin domain. The vector system may be recombinant AAV, the promoter may be a constitutive promoter such as, but not limited to, a CMV promoter or a hybrid CMV enhancer/chicken β-actin promoter (CAG).

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the invention. These examples are illustrations of the methods and systems described herein and are not intended to limit the scope of the invention. The type 1 rhodopsin domain of a channelrhodopsin derived from *Mesostigma viride*, MChR1; CaChR1, the type 1 rhodopsin domain of a channelrhodopsin derived from *Chlamydomonas augustae* and CyChR1 the type 1 rhodopsin domain of a channelrhodopsin derived from *Chlamydomonas yellowstonensis* as identified herein were chosen to exemplify how these channelrhodopsins can be identified, cloned, expressed, characterized and used. Non-limiting examples of such include, but are not limited to

EXAMPLES

Channelopsins Derived from *Mesostigma Viride*

Example 1

Source and Growth of Algae

*Mesostigma viride* strain CCMP2046 (aka NIES 296) was obtained from the Provasoli-Guillard National Center for the Culture of Marine Phytoplankton. Cells were grown at 25° C. in modified Jaworski medium (the concentration of Ca(NO$_3$)$_2$ was increased to 0.17 mM; 0.5 mM KNO$_3$, 0.15 µM ZnSO$_4$ and 0.04 µM CoCl$_2$ were added) under a 12 h light (~3,000 lux): 12 h dark cycle.

Example 2

Rhodopsin-Mediated Photocurrents in Algae Cells

Currents were measured with the population assay described in (Sineshchekov, O. A., E. G. Govorunova, A. Der, L. Keszthelyi, and W. Nultsch. Photoelectric responses in phototactic flagellated algae measured in cell suspension. *J. Photochem. Photobiol. B: Biol.* 13:119-134, 1992). Two platinum wires immersed in a cell suspension pick up an electrical current generated in response to a unilateral excitation flash from a Vibrant HE 35511 Tunable Laser (OPOTEK Inc., Carlsbad, Calif.) set at desired wavelengths. The signal was amplified by a low-noise current amplifier (Model 428, Keithley Instruments, Cleveland, Ohio) and digitized by a Digidata 1322A supported by pClamp 10 software (both Molecular Devices, Union City, Calif.).

Example 3

Cloning and Expression of *M. Viride* Channelrhodopsin

Total RNA was extracted from 500 ml of 1 week-old culture of *M. viride* using Trizol reagent (Invitrogen, Carlsbad, Calif.). Synthesis of 3' and 5' RACE-ready first-strand cDNAs and 3' and 5' RACE PCR were carried out using the SMARTer RACE cDNA amplification kit (Clontech Laboratories, Takara Bio Company, Mountain View, Calif.) using primers designed according to the opsin sequence fragment found in the Taxonomically Broad EST Database Taxonomically Broad EST Database (O'Brien et al. Nucleic Acids Res. January; 35 (Database issue): D445-D451, 2007). The overlapping RACE fragments were combined by fusion PCR, cloned into pCR2.1-TOPO vector (Invitrogen) and fully sequenced. The 7TM domain (encoding residues 1-331) was inserted between BamHI and NotI sites to replace the VChR1 sequence in the pcDNA3.1/VChR1-EYFP mammalian expression vector provided by K. Deisseroth (Stanford University). The presence of a fluorescent tag is not expected to affect channelrhodopsin properties, as has been shown by quantitative comparison of photocurrents generated by YFP-, mCherry- and myc-tagged ChR2 (Nikolic, K., N. Grossman, M. S. Grubb, J. Burrone, C. Toumazou, and P. Degenaar. Photocycles of channelrhodopsin-2. *Photochem. Photobiol.* 85:400-411, 2009). Point mutations were introduced using the QuikChange XL Site-Directed Mutagenesis Kit (Stratagene, La Jolla, Calif.). HEK293 cells were transfected using the TransPass COS/293 transfection reagent (New England Biolabs, Ipswich, Mass.). All-trans-retinal (stock solution in ethanol) was added to a final concentration 2.5 µM.

Example 4

Photoreceptor Activity

Whole-Cell Patch Clamp Recording:
Measurements were performed 24-48 h after transfection with an Axopatch 200B amplifier (Molecular Devices, Union City, Calif.). The signals were digitized with a Digidata 1440A using pClamp 10 software (both from Molecular Devices). Patch pipettes with resistances 2-5 MΩ were fabricated from borosilicate glass and filled with the following solution (in mM): KCl 126, MgSO$_4$ 2, CaCl$_2$ 0.5, EGTA 5, glucose 20, HEPES 25, pH 7.2. The bath solution contained (in mM): NaCl 150, CaCl$_2$ 1.8, KCl 4, MgCl$_2$ 1, glucose 5, HEPES 10, pH 7.4. Unless otherwise indicated, the holding potential was −60 mV. Light excitation was provided by a Polychrome IV light source (T.I.L.L. Photonics GMBH, Grafelfing, Germany) pulsed with a mechanical shutter (Uniblitz Model LS6, Vincent Associates, Rochester, N.Y.). The light intensity was attenuated with the built-in Polychrome system or with neutral density filters.

Figure 1:
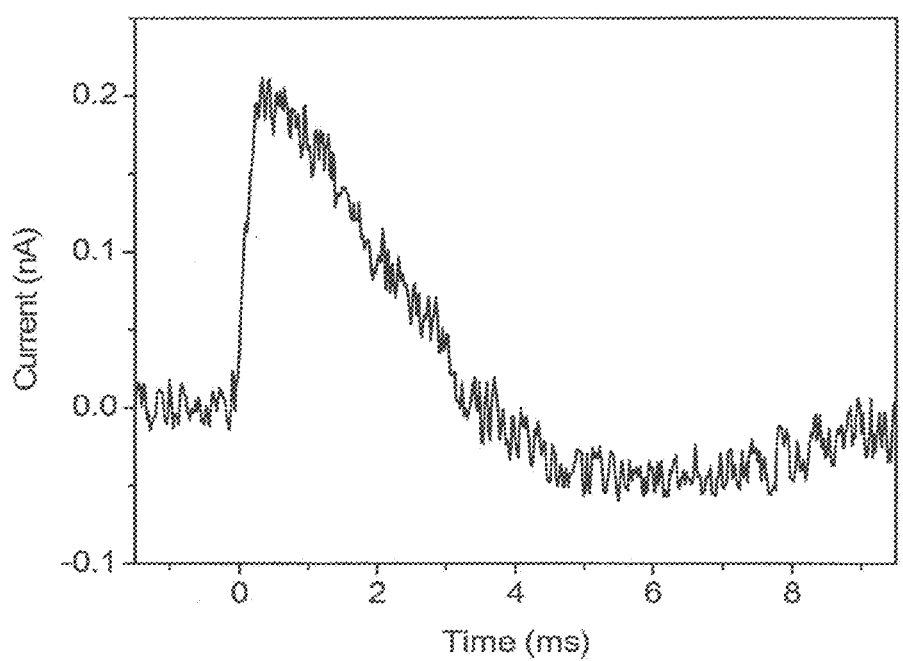
FIG. 1 depicts the photoelectric response in a suspension of native cells of *Mesostigma viride*. Unilateral excitation with a 6-ns-laser pulse at 530 nm.
Figure 2:
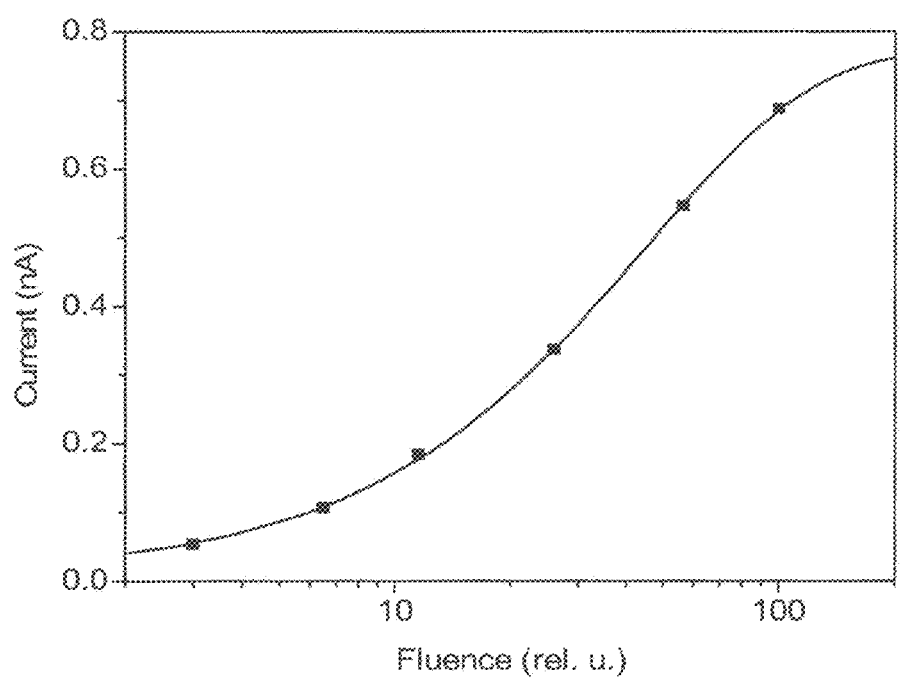
FIG. 2 depicts fluence-response dependence of the photoreceptor current. Excitation: broad-band 520 nm light from the photoflash.

Rhodopsin-Mediated Photoelectric Currents in *M. viride* Cells:

Photoreceptor currents in native *M. viride* cells were measured in cell suspensions under unilateral laser flash excitation. The response was similar to those previously observed in other phototactic flagellates with the intrachloroplast eyespots. However, it was significantly faster, with a peak time of <0.5 ms and a half-rise time of 100 µs (as shown in FIG. 1). In addition, photocurrents in *M. viride* lacked a kinetic contribution of the late (delayed) photoreceptor current discovered earlier in green algae to the recorded signal (as shown in FIG. 1). The second component was also not found in the fluence-response dependence (as shown in FIG. 2), which was well fit with a single exponential function that saturated at about the same light intensities as previously studied early photoreceptor currents in other flagellate algae. However, in contrast to other flagellates, the curve in *M. viride* was well fit without introducing an additional low-saturating component, which means that the amplified current component did not contribute to the signals.

Figure 3:
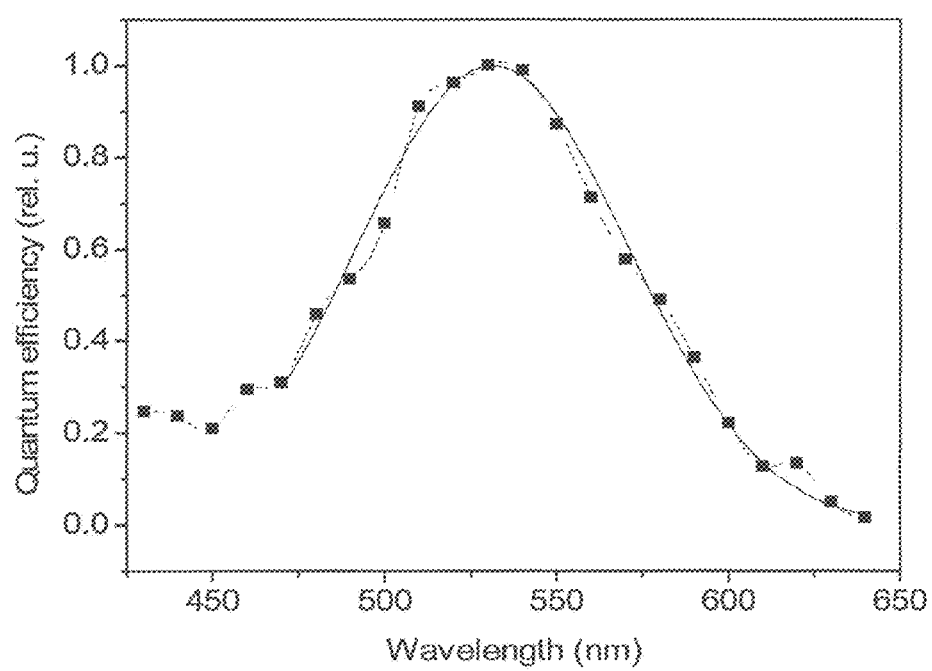
FIG. 3 depicts the action spectrum of the photoreceptor current in native *M. viride* cells. Solid line, Gaussian fit of the main peak, maximum 531 nm, half-bandwidth ~93 nm.

The action spectrum for the photoreceptor current in suspensions of *M. viride* cells is shown in FIG. 3. The spectral sensitivity was estimated by calculating the mean value of the current response between 50 µs and 2 ms. The first 50 µs was omitted because during this time a fast photosynthetic signal developed. To completely eliminate the contribution of this signal, the traces were further corrected by subtracting the responses evoked by a 680-nm laser flash. This wavelength is ineffective for generation of channelrhodopsin-mediated currents or motility responses in flagellates, but is absorbed by the photosynthetic pigments. The spectrum was corrected for photon density, taking into account the logarithmic fluence-response dependence (FIG. 2). The spectral maximum at 531 nm was determined by Gaussian fit of the main peak (the solid line in FIG. 3). The 90-nm half-bandwidth of the spectrum is typical of retinal proteins, indicating that a single rhodopsin species is responsible for the light-induced currents in *M. viride*. Significant light-sensitivity of the electric response is observed even beyond 620 nm. This long-wavelength action spectrum and the fast kinetics of the photoelectric current identified this organism as a candidate for source for cloning a channelrhodopsin that would facilitate and improve optogenetics applications.

Example 5

Primary Structure *M. Viride* Opsin

Figure 4:
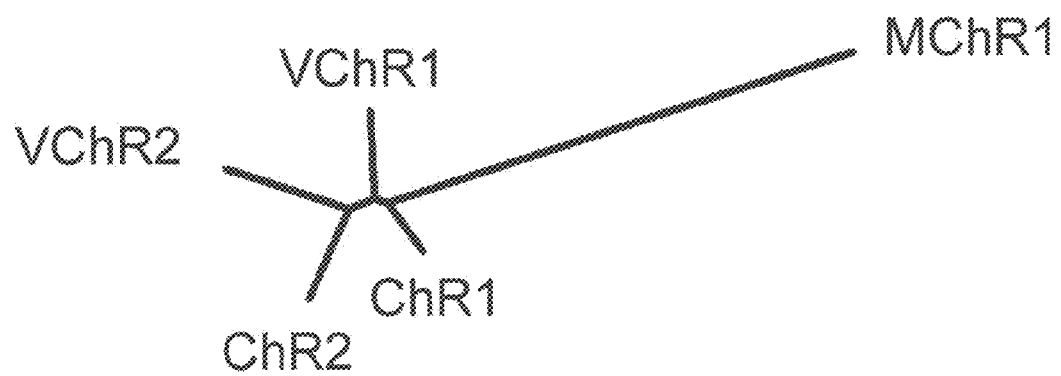
FIG. 4 illustrates a phylogenetic tree of the channelrhodopsin family constructed by the Neighbour-Joining method. In this figure, ChR1 is channelrhodopsin 1 from *C. reinhardtii*; ChR2 is channelrhodopsin 2 from *C. reinhardtii*; VChR1 is channelrhodopsin 1 from *V. carteri*; VChR2 is channelrhodopsin 2 from *V. carteri*; and MChR1 is channelrhodopsin 1 from *M. viride*.

The opsin sequence cloned from *M. viride* (593 residues, peptide sequence provided as SEQ ID NO: 1) consists of a 7TM domain and an extended C-terminal domain, as is characteristic of other known channelrhodopsins. The channelopsin is the apoprotein, while channelrhodopsin is the protein and retinal. Strictly speaking the amino acid sequences (SEQ ID NOS:1-4) define the opsin, but this is also the sequence of the rhodopsin, which is the same. Most of the residues known to form the retinal-binding pockets of other sensory rhodopsins and BR were conserved. However, overall homology of this sequence to other channelrhodopsins is lower than between any two of them: its 7TM domain shows 38% identity and 52% similarity with ChR1, 35% and 51% with ChR2, 36% and 51% with VChR1, and 37% and 53% with VChR2. The genomes of C. reinhardtii and V. carteri are completely sequenced, and each contains only two channelopsin genes. Complete genomic information is not available for M. viride and there is a possibility that its genome also contains more than one channelopsin. Based on sequence homology the M. viride protein could not be distinguished as a channelrhodopsin 1 or 2 since it is only slightly closer to the two channelrhodopsin 1 sequences (FIG. 4). Also this sequence lacks two structural features that differentiate ChR1/VChR1 from ChR2/VChR2. First, there is no Glu residue corresponding to E87 (ChR1 numbering), which is implicated by mutagenesis as required for the pH-dependent spectral shift characteristic of ChR1/VChR1 (Tsunoda, S. P., and P. Hegemann. Glu 87 of channelrhodopsin-1 causes pH-dependent color tuning and fast photocurrent inactivation. *Photochem. Photobiol.* 85:564-569, 2009). Also the position of Y226 (ChR1)/N187 (ChR2), conserved in VChR1 and VChR2, respectively, is one of the molecular determinants of spectral sensitivity, desensitization and kinetics, by which ChR1 differs from ChR2 (Wang, H., Y. Sugiyama, T. Hikima, E. Sugano, H. Tomita, T. Takahashi, T. Ishizuka, and H. Yawo. Molecular determinants differentiating photocurrent properties of two channelrhodopsins from *Chlamydomonas. J. Biol. Chem.* 284:5685-5696, 2009). In the M. viride protein this site is occupied by a Trp residue.

In the two known channelrhodopsin pairs, the more red-shifted one is defined as channelrhodopsin 1. The spectral sensitivity of M. viride channelrhodopsin is more red-shifted than that of any previously known species, including the most red-shifted VChR1 (see below). Therefore, it was named MChR1 (and not 2).

Unexpectedly, several residues in the 7TM region previously considered as defining features of the channelrhodopsin family based on the four known homologs, were not conserved in MChR1, as described below under Example 7, below. The C-terminal domain of MvR1 shows even lower homology to that of other channelrhodopsins than the 7TM domain.

Example 6

Channel Activity in Mammalian Cells

Figure 6:
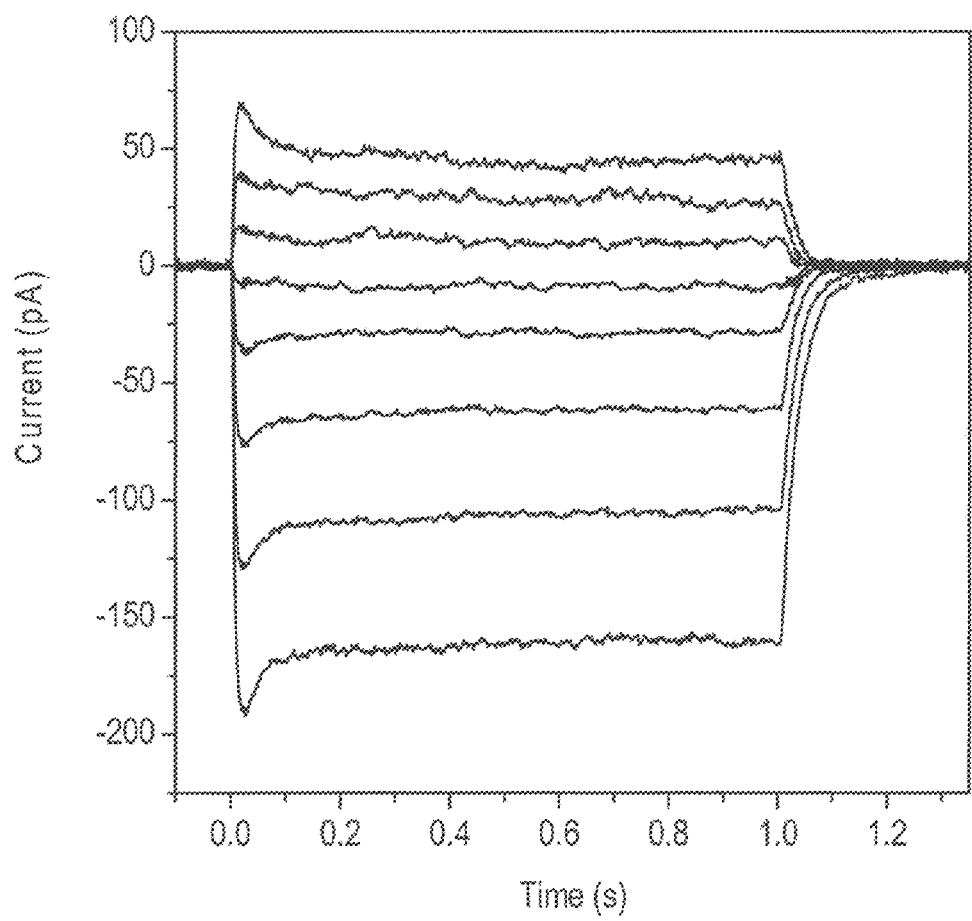
FIG. 6 illustrates photocurrents in HEK293 cells expressing the 7TM-domain of MChR1 from *M. viride* recorded by the whole-cell patch clamp method at different holding potentials changed in 20 mV steps from −100 mV (the bottom trace) to +40 mV (the top trace).
Figure 7:
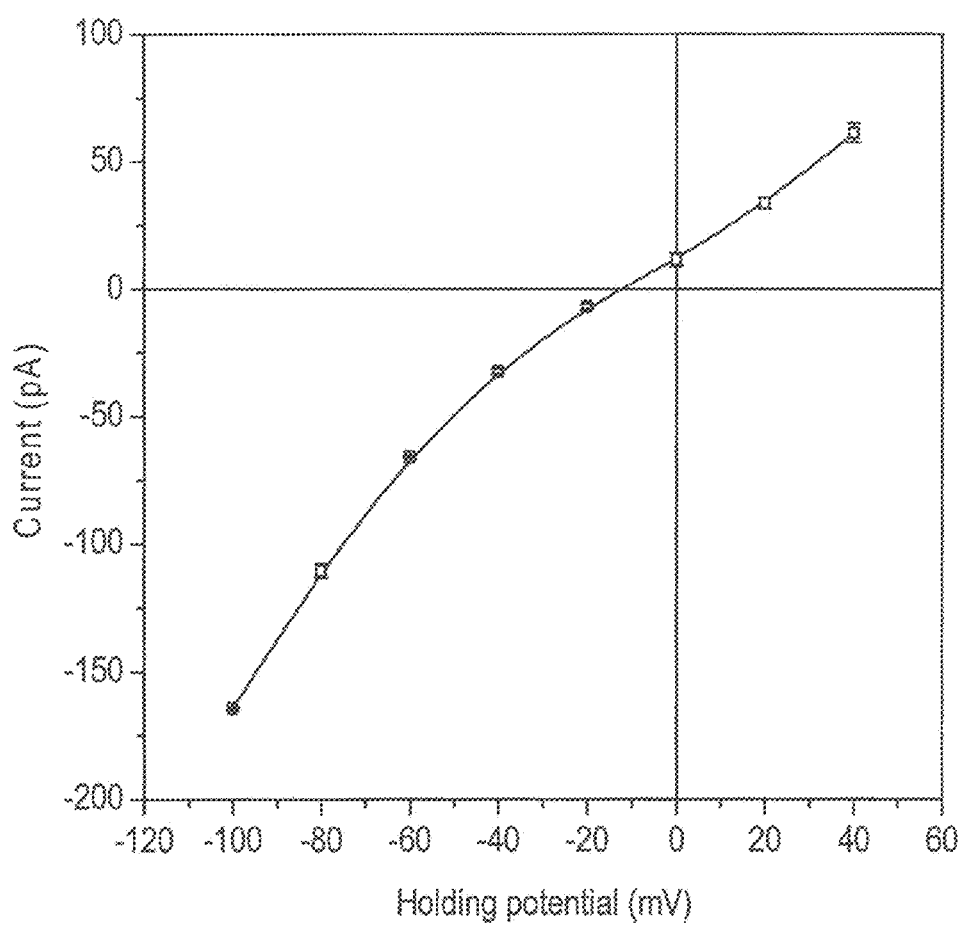
FIG. 7 illustrates current-voltage dependencies of the peak current (squares, solid line) and the plateau level (circles, dashed line). Data are the mean values±SEM of four successive scans.
Figure 8:
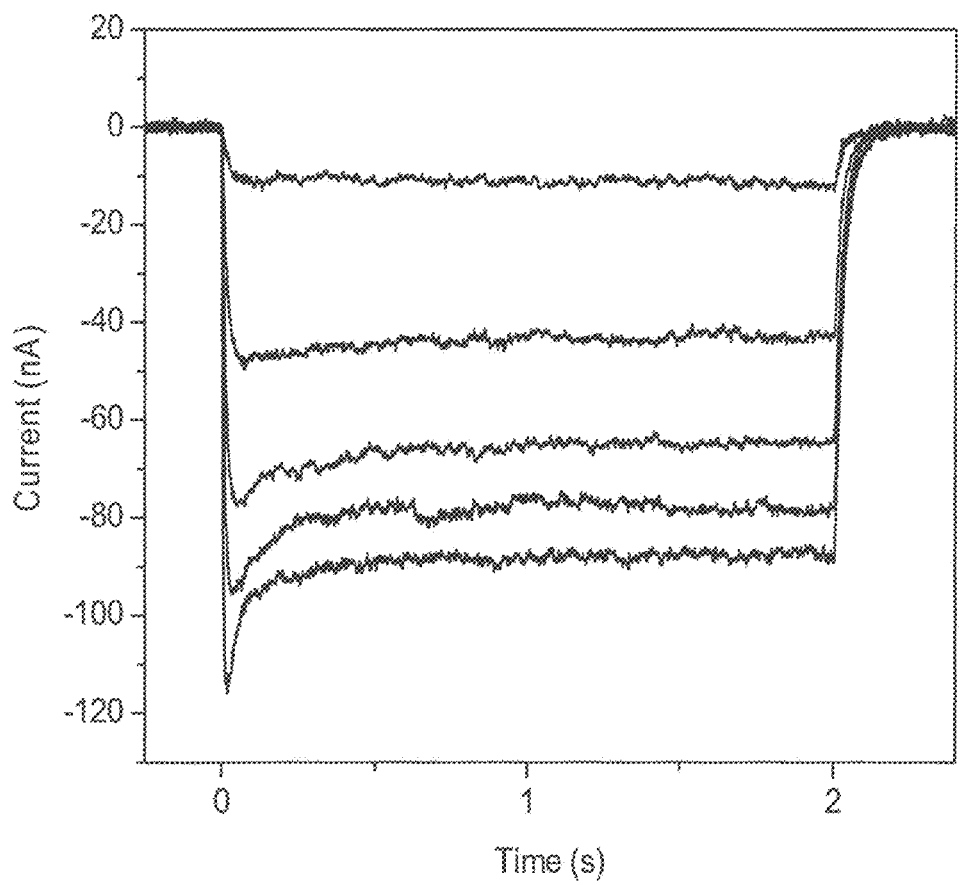
FIG. 8 illustrates photocurrents in HEK293 cells expressing the 7TM-domain of MChR1 from *M. viride* recorded by the whole-cell patch clamp method. Excitation: 530 nm, 2 s; relative light intensities, starting from the bottom trace: 100%, 20%, 7%, 3%, 0.5%.

The light-gated channel activity of *Mesostigma* rhodopsin was tested in HEK293 cells (FIG. 6). Characterization of the 7TM domain of MChR1 (331 residues: SEQ ID NO: 1) and photocurrent generated by MChR1 under sustained illumination decayed from a peak to a plateau, a phenomenon called inactivation (FIG. 6). The amplitude and the sign of the photocurrent depended on the holding potential with the reversal potential close to zero (FIG. 7). The peak current and the plateau level had identical I-V curve shapes and reversal potentials. The relatively small inactivation of MChR1-generated currents showed it is functionally closer to ChR1 than to ChR2, as the former exhibits a lower degree of inactivation (16). The mean peak value of MChR1 photocurrents at the saturating light intensity and −60 mV holding potential was 276±97 pA (n=12, mean±SEM), which is comparable to that reported for VChR1 in neurons, and to the measurements of VChR1 in HEK cells. The plateau amplitude of MChR1 photoresponses saturated at lower light intensities than the peak value (FIG. 8) and the degree of inactivation increased with the light intensity. When successive pulses were applied with a variable dark interval, the amplitude of the peak recovered with (theta) τ ~3.5 s at pH 7.4, which was faster than that reported in other channelrhodopsins. In addition to this short-term process, another, long-term recovery was made evident by the fact that the first light stimulus always elicited a larger response than any subsequent one, even after minutes of dark adaptation.

Figure 9:
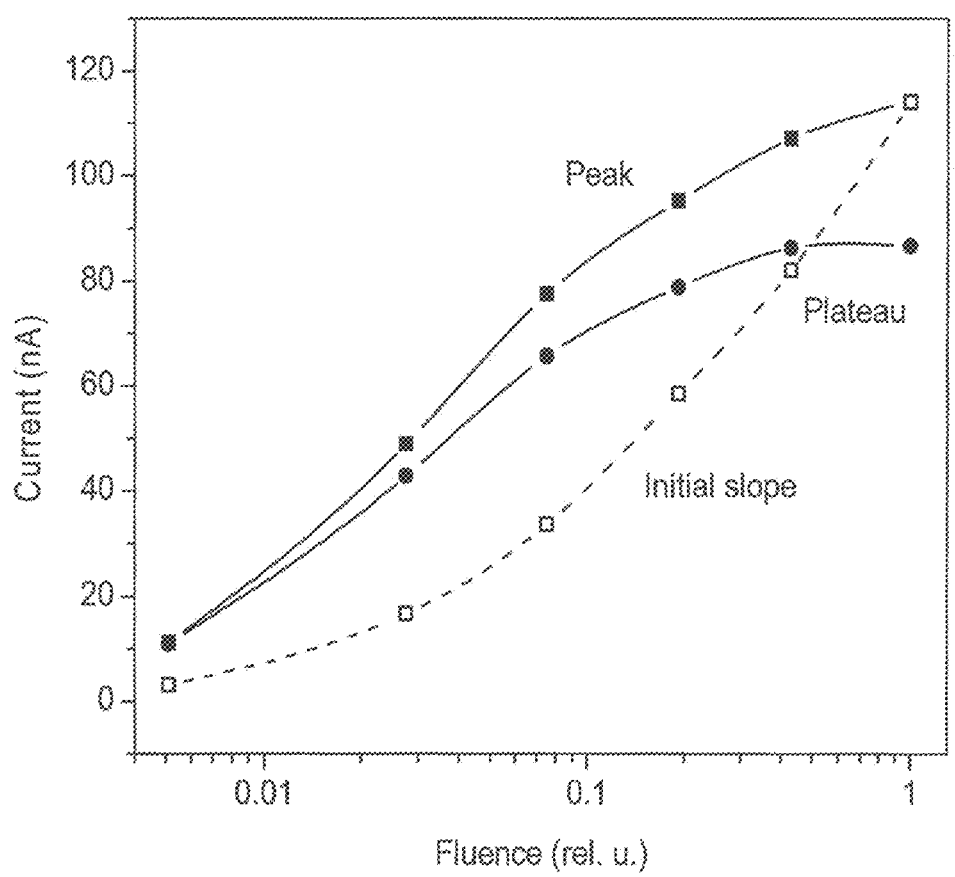
FIG. 9 illustrates dependence of the initial slope (open squares, dashed line) and amplitudes of the peak and plateau currents (filled squares and filled circles, respectively, solid lines) on the light intensity. Stimulating light 530 nm, 2 s; dark interval 30 s. The initial slope of the photocurrent was normalized to the peak value at the maximal intensity.

Estimation of the absorption properties of a receptor responsible for a photobiological response is usually done using action spectroscopy. For the action spectrum to faithfully reflect the absorption spectrum of the pigment, the response needs to be measured far from saturation, ideally in the linear range of the intensity-response curve. Also, the action spectrum should be measured in response to a short stimulus to avoid secondary photochemistry, which may produce a spectrally-dependent mixture of intermediates, affecting the action spectrum. The initial slope of the photocurrent (assessed from the mean amplitude of the signal recorded during the first 50 ms of illumination with low-intensity light) was measured to evaluate spectral properties of the ground state of MChR1 in HEK cells. This parameter showed a near linear dependence on light even at such intensities when both the peak and plateau levels saturated (FIG. 9) and hence could be easily corrected for equal photon density.

Figure 10:
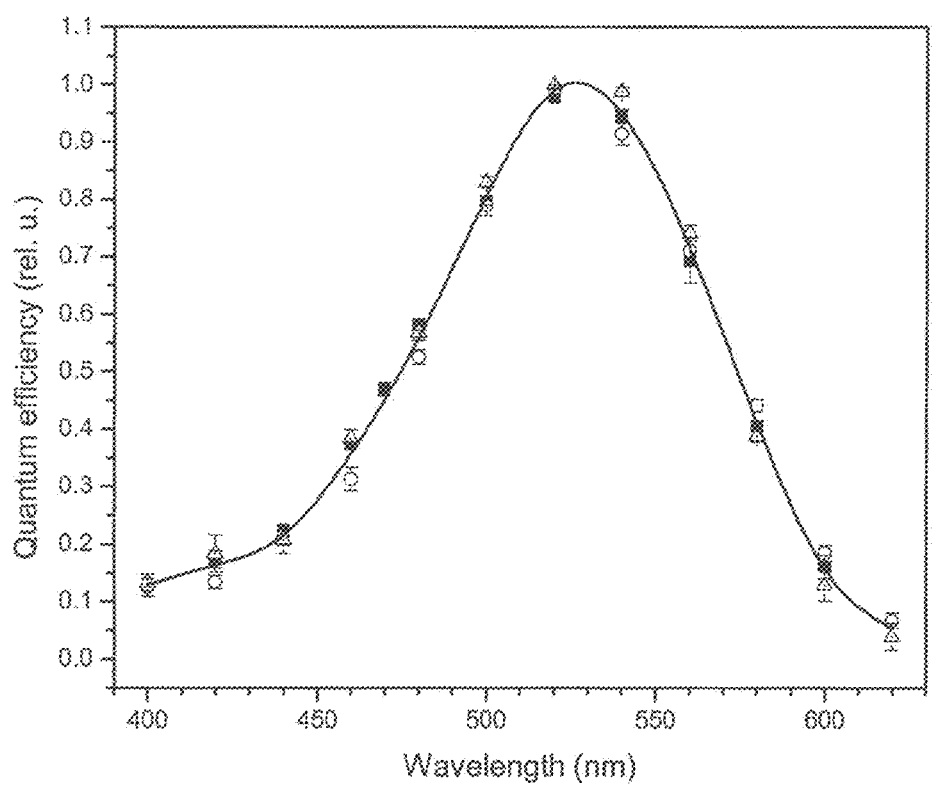
FIG. 10 illustrates low light-intensity action spectra of photoelectric responses in HEK293 cells of MChR1 from *M. viride* at the external pH 9.0 (solid squares), 7.4 (open circles) and 5.3 (open triangles). As these data were very close, a single B-spline solid line was drawn through the average values at each wavelength. Data for each spectrum are the mean values±SEM of 6 to 10 successive scans in opposite directions obtained on 2 to 3 cells.

The action spectra of MChR1 light-gated channel activity in HEK cells measured as outlined above at three values of external pH are shown in FIG. 10. To reveal the position of their maxima, the main peaks of the spectra were fitted with a Gaussian function (as shown in FIG. 3 for the spectrum in native M. viride cells). At all three pH values, the spectral maximum was at 528 nm, which corresponded within 3-nm accuracy to the maximum of the spectral efficiency of the pigment in native M. viride cells (FIG. 3).

Figure 11:
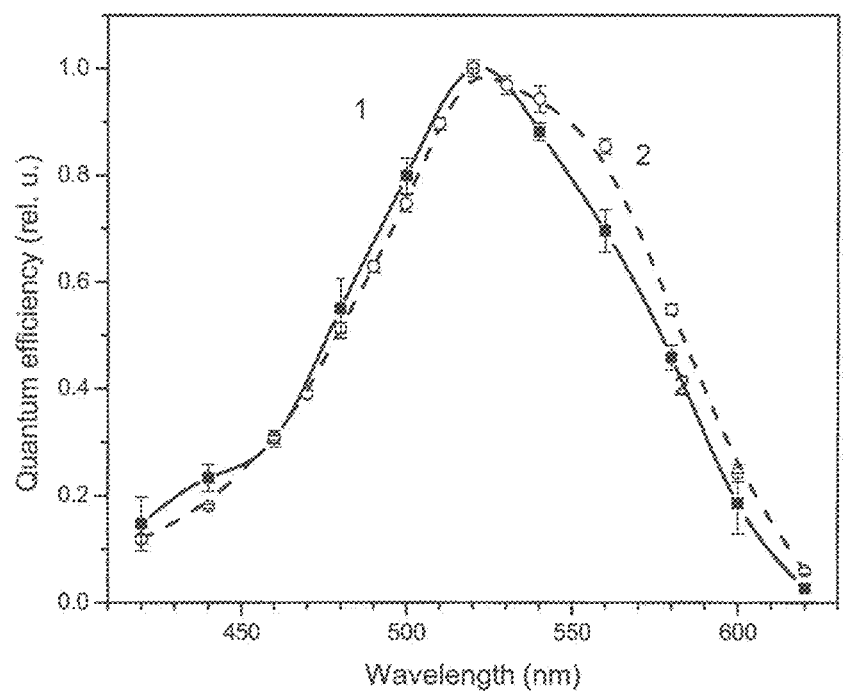
FIG. 11 illustrates low light-intensity action spectra of photoelectric responses in HEK293 cells of VChR1, from *Volvox carteri* at the external pH 7.4 (solid squares, solid line) and 5.3 (open circles, dashed line). As these data were very close, a single B-spline solid line was drawn through the average values at each wavelength. Data for each spectrum are the mean values±SEM of 6 to 10 successive scans in opposite directions obtained on 2 to 3 cells.

The long-wavelength spectral sensitivity found in MChR1 is one of the properties highly desirable for neurobiological applications. The most red-shifted channelrhodopsin variant previously reported is VChR1 from V. carteri. The action spectra of light-gated channel activity of VChR1 was characterized under the same experimental conditions used for MChR1 and it was determined, using the same fitting algorithm, that the VChR1 spectrum peaked at 520 nm at neutral pH (FIG. 11, solid line), which was ~8 nm less than that measured in MChR1 (FIG. 10). The 520 nm peak of the VChR1 spectrum corresponded to the absorption maximum of the isolated pigment measured at this pH. Acidification of the external medium led to the appearance of a red-shifted shoulder in the VChR1 action spectrum (FIG. 11, dashed line). The maximal absorption of purified VChR1 has been reported to shift to 540 nm at low pH, indicating conversion of the pigment to a protonated form. These findings suggested that either partial conversion occurred in HEK cells, or that the conductance of the protonated state was much smaller than that of the 520 nm form.

Figure 12:
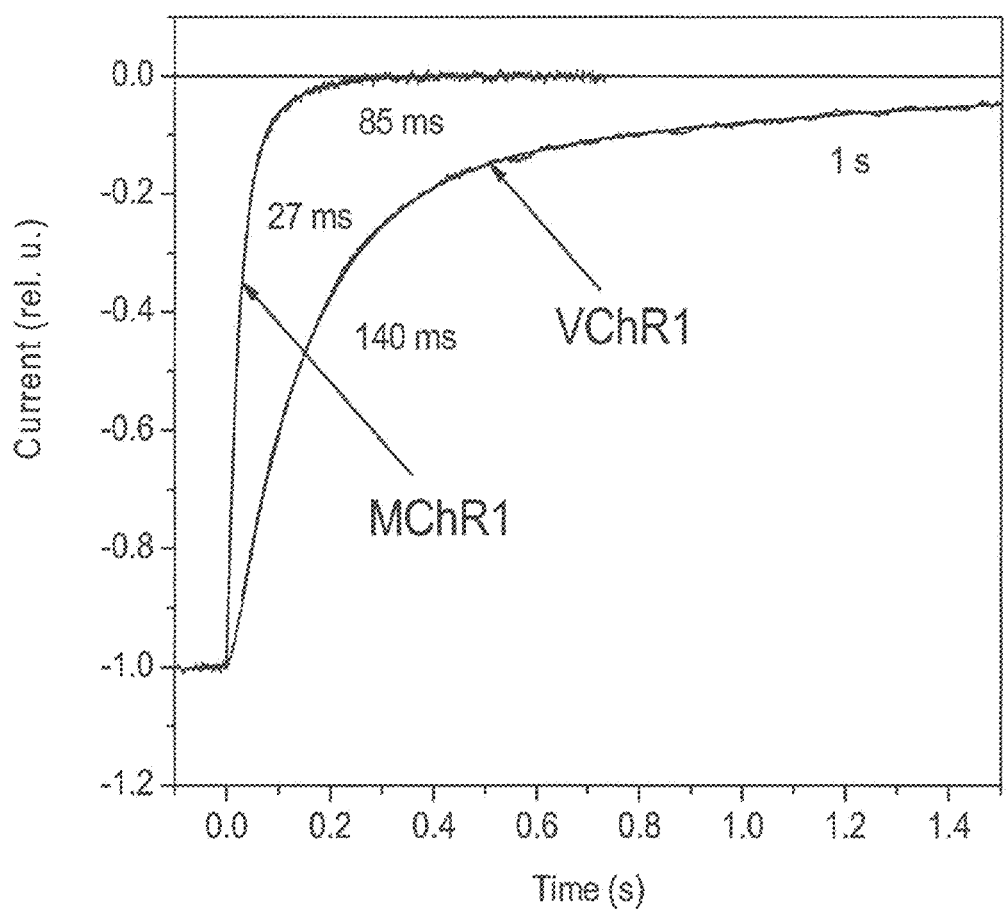
FIG. 12 illustrates current kinetics of MChR1 from *M. viride* and VChR1 from *V. carteri* (filled squares and open circles, respectively) expressed in HEK293 cells. Excitation: 530 nm, 2 s. Zero time corresponds to the end of the light pulse. Data are the mean values±SEM of 6 to 10 cells for each pH value.
Figure 13:
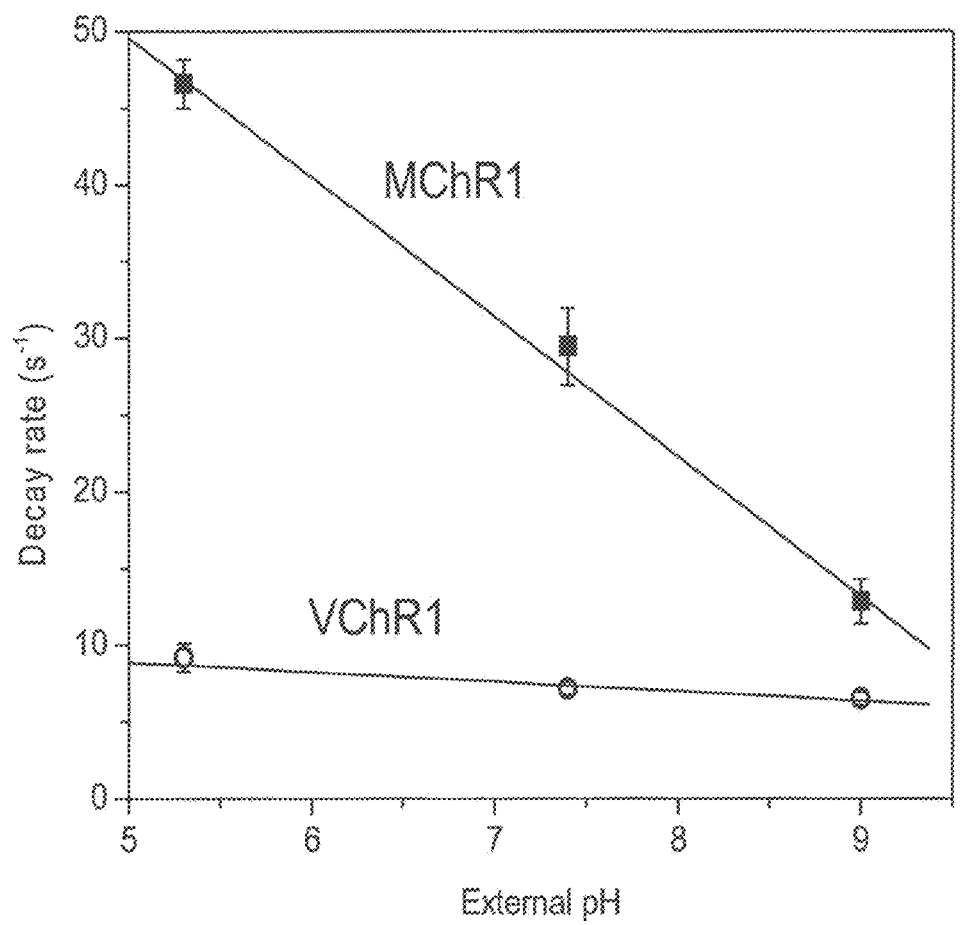
FIG. 13 illustrates dependence of the rate of the fast decay component on the external pH of MChR1 from *M. viride* and VChR1 from *V. carteri* (filled squares and open circles, respectively) expressed in HEK293 cells. Excitation: 530 nm, 2 s. Data are the mean values±SEM of 6 to 10 cells for each pH value.

The main difference between the two red-shifted channelrhodopsins was that the current decay after switching off the light was much faster in MChR1 than in VChR1. In both cases, the decay kinetics was better fit with two exponentials. At neutral pH, the time constants of both components were respectively smaller in MChR1 than in VChR1 (FIG. 12). In addition, the relative amplitude of the slow component was smaller in MChR1, further increasing the rate of the overall decay. The fast component of MChR1 was further characterized due to the small contribution of the slow component to the decay kinetics in MChR1. Its rate strongly increased upon acidification of the external medium from the pH 9.0 to 5.3 (FIG. 13, filled symbols), whereas in VChR1 it was only slightly increased (FIG. 13, open symbols). However, the rate of the slow component in VChR1 showed a stronger dependence on pH than the fast component.

Example 7

Functional Analysis Using Mutagenesis

MChR1 showed some typical light-gated channel activity upon heterologous expression but not all structural features found in other channelrhodopsins were conserved in its primary sequence. To characterize the functional importance of these features, MChR1 point mutants (V102E and A116E) were generated and compared to known channelrhodopsins and their activity analyzed.

Figure 5:
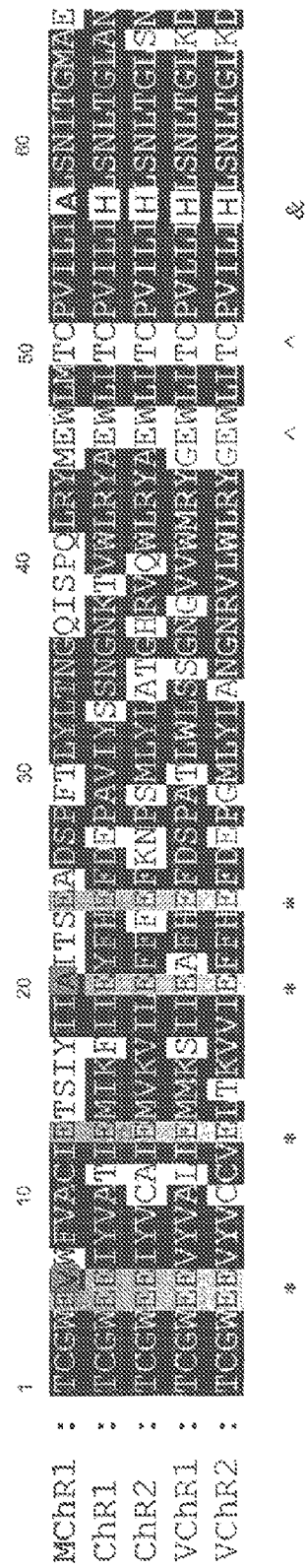
FIG. 5 illustrates alignment of channelrhodopsin sequences (regions of the predicted helices B and C of the 7 TM domain). The conserved Glu residues are shown in the residues 5-6 (*), the conserved His residue at the proton donor position in BR (Asp96) is shown at residue 57 (&), other conserved residues of the retinal-binding pocket are shown in the light shaded residues 45-47 and 50-51 (^), and the important residues that are not conserved in MChR1 are indicated in the top row, residues 6, 20, and 57, as V, A, A, respectively). In this figure, ChR1 is channelrhodopsin 1 from *C. reinhardtii* (Seq ID NO:17); ChR2 is channelrhodopsin 2 from *C. reinhardtii* (Seq ID NO:18).; VChR1 is channelrhodopsin 1 from *V. carteri* (Seq ID NO:19).; VChR2 is channelrhodopsin 2 from *V. carteri* (Seq ID NO:20); and MChR1 is channelrhodopsin 1 from *M. viride* (Seq ID NO:16).

V102E and A116E Mutants:

All previously identified channelrhodopsins contain an array of five Glu residues in the predicted second helix, but only three of these are conserved in MChR1 (FIG. 5). Thus it was expected that introducing the missing glutamates (corresponding to E83 and E97 in the ChR2 sequence) in the MChR1 sequence would enhance its channel activity. However, both mutations resulted in a substantial decrease in the whole-cell current amplitude (~7-fold in A116E and more than 100-fold in V102E). This amplitude depends on the properties of individual channelrhodopsin molecule and on the number of functional molecules in the plasma membrane. Based on visual observations, the intensity of EYFP fluorescence in the membrane was not significantly changed by the V102 and A116E mutations. The presence of comparable EYFP fluorescence suggests that the expression level was not affected, although it does not exclude that the protein was misfolded. These mutations also inhibited the channel function of the MChR1 molecule, as was revealed by a significant slowing down of the current kinetics (FIG. 14 for A116E; data for V102E are not shown). In the double mutant V102E/A116E (both glutamates introduced) the photocurrents were below the detection limit.

A153/H/R Mutants:

All previously identified channelrhodopsins have a His residue at the position of the proton donor in BR (D96), and its replacement with Arg results in an increase in the stationary current amplitude in ChR2 (10). When Ala found in MChR1 in this position was replaced with His or Arg, the current was completely suppressed without decreasing the EYFP fluorescence in the membrane.

C147A and D175A Mutants:

For previously identified channelrhodopsins, it has been suggested that residues C128 and D156 in ChR2 form a hydrogen-bond between helices C and D that is important for channel gating and that its disruption leads to a dramatic increase in the lifetime of the channel's open state. The corresponding residues (C147 and D175) are conserved in MChR1. Replacing either of these residues with Ala led to a large decrease in the EYFP fluorescence indicating a decrease in protein expression levels. Current amplitude was also significantly decreased to a maximal signal of ~20 pA.

Figure 14:
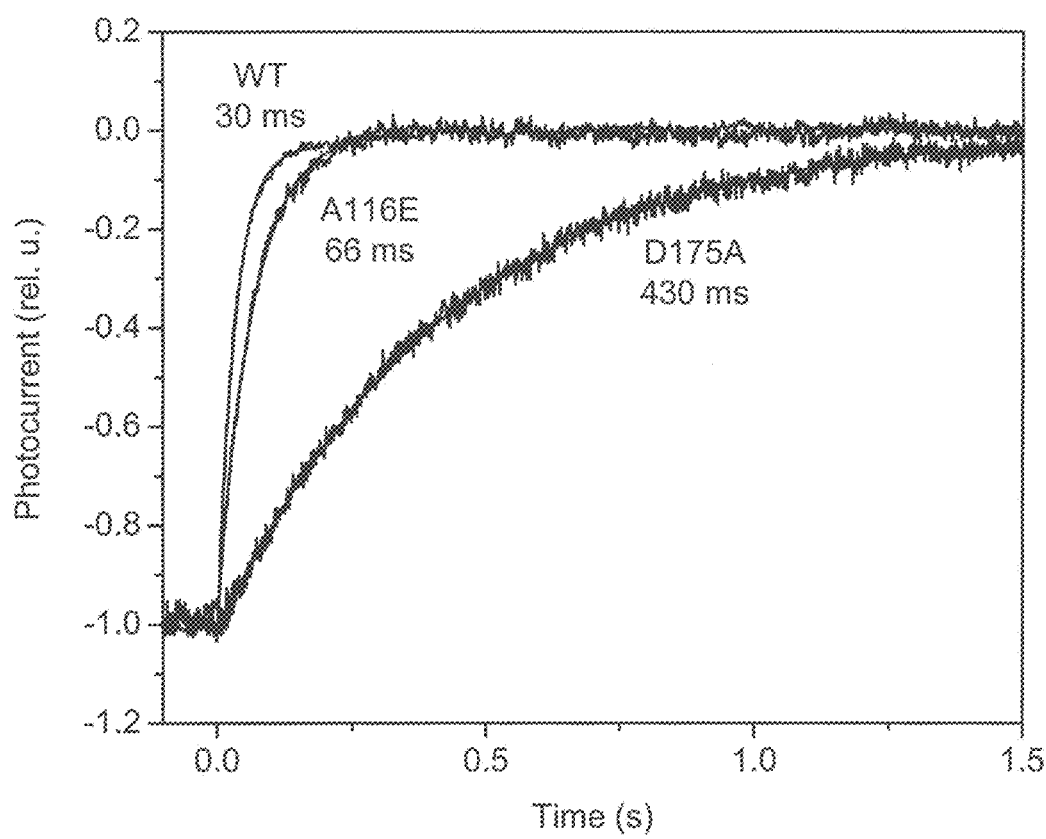
FIG. 14 illustrates photocurrents generated by the A116E and C147A mutants and wild-type MChR1 from *M. viride* in HEK293 cells. Traces were normalized at the plateau level to reveal the differences in the decay kinetics. The increased level of the noise qualitatively reflects a decrease in the absolute current amplitudes. Excitation 530 nm, 0.5 s. Zero time corresponds to the end of the light pulse.

However, in agreement with the ChR2 result, analysis of the current kinetics showed a similar dramatic increase in the decay time (FIG. 14 for D175A; data for C147A are not shown).

Channelopsins Derived from *Chlamydomonas*

Example 8

Source and Growth of Algae

Algal strains were obtained from the Culture Collection of Algae at the University of Texas (UTEX), Austin, Tex. and the National Center for Culture of Marine Phytoplankton (CCMP), West Boothbay Harbor, Me. *Chlamydomonas augustae* (UTEX SNO134) and *Chlamydomonas yellowstonensis* (UTEX B SNO155) were grown in Bold 1NV medium (described by Starr, R. C. and J. A. Zeikus (1993) UTEX—the culture collection of algae at the University of Texas at Austin. *J. Phycol.* 29 (suppl.), 1-106) under illumination of 14 µmol photon×m$^{-2}$×s$^{-1}$ at 4° C. or 16° (*C. augustae*), or 4° C. (*C. yellowstonensis*). *Chlamydomonas raudensis* (CCMP 1619) was grown in modified Bold's basal medium (described by Bischoff, H. W. and H. C. Bold (1963) Phycological studies IV. Some soil algae from Enchanted Rock and related algal species. *University of Texas Publication* 6318, 1-95) containing vitamins and three times the amount of nitrogen and vitamins as described at the website of the Culture Collection of Algae and Protozoa (UK) under illumination of 5 µmol photon×m$^2$×s$^{-1}$ at 4° C. Illumination was set to a 16 h light, 8 h dark cycle and was provided by cool-white fluorescent lamps.

Example 9

Cloning and Expression of *Chlamydomonas* Channelrhodopsins

Homology Cloning of Sequences.

Algae were inoculated from plates into 25 mL liquid medium in 250 mL flasks and grown for 18 hr at 16° C. (*C. yellowstonensis*) or 4° C. (*C. raudensis*). Total RNA was extracted with Trizol reagent (Invitrogen, Carlsbad, Calif.). First strand cDNA was synthesized with the Transcriptor first strand cDNA synthesis kit (Roche Diagnostics, Mannheim, Germany) using oligo-d(T) primer. The degenerate primers were designed according to the conserved regions of the four earlier known channelopsins from *C. reinhardtii* and *V. carteri*, and their degeneracy was reduced by including only the most frequently used codons. The forward primer was SYHB-F (5'-TGC GGN TGG GAG GAG RTN TA-3' (SEQ ID NO: 13), and the reverse primers were SYOG-R (5' AGR ATR TGC TCR TGR ATC-3'(SEQ ID NO: 14)) for *C. augustae* and *C. yellowstonensis*, and SYLPEF-R (5'-RCC CTT SGG NAC SGT RTG-3' (SEQ ID NO: 15)) for *C. raudensis*. The PCR (polymerase chain reaction) program was as follows: denaturation at 98° C. for 2 min, followed by 30 cycles of 98° C. for 30 s, 49° C. for 45 s, 72° C. for 55 s, and final extension at 72° C. for 5 min. PCR fragments were cloned into the pGEM-T Easy vector (Promega, Madison, Wis.) and sequenced. For the fragments that showed homology with channelopsins, 3' and 5' RACE (rapid amplification of cDNA ends) was performed using the SMARTer RACE cDNA amplification kit (Clontech Laboratories, Mountain View, Calif.). Overlapping RACE fragments were joined by fusion PCR to obtain full-length cDNA, which was cloned into the pGEM-T Easy vector and sequenced.

Fragments encoding for the 7TM domains (residues 1-352 for the *C. augustae* and *C. raudensis* sequences, and 1-354 for *C. yellowstonensis*) were inserted between BamHI and NotI sites to replace the VChR1 sequence in the pcDNA3.1/VChR1-EYFP mammalian expression vector provided by K. Deisseroth (Stanford University). The vector map and sequence are available at the Optogenetics Resource Center website. The presence of a fluorescent tag is not expected to affect channelrhodopsin properties, as has been shown by quantitative comparison of photocurrents generated by YFP-, mCherry- and myc-tagged ChR2.

Example 10

Structural Sequence Analysis

Figure 17:
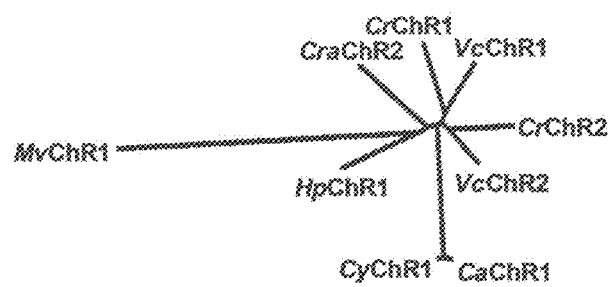
FIG. 17 illustrates a phylogenetic trees of the 7TM domains of the so far known channelopsins constructed by the neighbor joining method CrChR1, channelrhodopsin 1 from *C. reinhardtii*; CrChR2, channelrhodopsin 2 from *C. reinhardtii*; VcChR1, channelrhodopsin 1 from *V. carteri*; VcChR2, channelrhodopsin 2 from *V. carteri*; MvChR1, channelrhodopsin 1 from *M. viride*; CaChR1, channelrhodopsin 1 from *C. augustae*; CyChR1, channelrhodopsin 1 from *C. yellowstonensis*; CraChR2, channelrhodopsin 2 from *C. raudensis*; HpChR1 channelrhodopsin 1 from *Haematococcus pluvialis* (nucleotide Acc. No. JN596950).

Channelopsin sequences from *C. augustae, C. yellowstonensis* and *C. raudensis*. Channelopsin homologs were cloned from each of *C. augustae* (SEQ ID NO: 2, 715 amino acid residues; nucleotide Acc. No. JN596951), *C. yellowstonensis* (SEQ ID NO: 3, 717 residues, Acc. No. JN596948) and *C. raudensis* (SEQ ID NO: 4, 635 residues, Acc. No. JN596949). The new proteins consist of a predicted 7TM (rhodopsin) domain responsible for light-gated channel activity and a C-terminal domain. ChR1/VChR1 and ChR2/VChR2 form two distinct branches on the phylogenetic tree of their 7TM domains (FIG. 17). The 7TM domains of the new *Chlamydomonas* sequences do not show closer homology with either the ChR1/VChR1 branch or ChR2/VChR2 branch, when their overall sequence homology is concerned (FIG. 17). The 7TM domains from *C. augustae* and *C. yellowstonensis* are however very close to each other.

Figure 19:
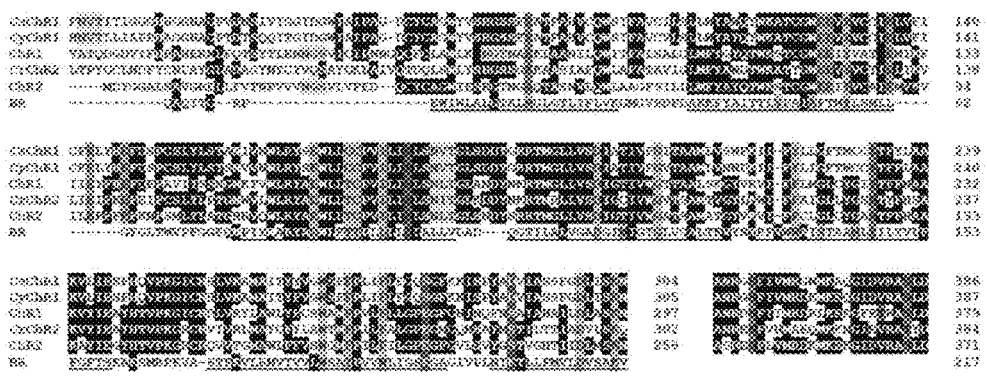
FIG. 19 illustrates a partial alignment of *Chlamydomonas* channelopsin and bacteriorhodopsin (BR) sequences. In this figure, ChR1 is channelrhodopsin 1 from *C. reinhardtii* (Seq ID NO:23); ChR2 is channelrhodopsin 2 from *C. reinhardtii* (Seq ID NO:25); CaChR1, channelrhodopsin 1 from *C. augustae* (Seq ID NO:21); CyChR1 is channelrhodopsin 1 from *C. yellowstonensis* (Seq ID NO:22); CrChR2 is channelrhodopsin 2 from *C. raudensis* (Seq ID NO:24); and BR is bacteriorhodopsin (Seq ID NO:26). Black background indicates conserved identical residues. The conserved Glu residues in the predicted second helix are shown in top row residues 88, 89, and 96 as well as middle row, residues 3 and 7. Residues that form the retinal-binding pocket in bacteriorhodopsin (BR) are positioned at top row, residues 83, 87 and 91; middle row, residues 29, 33, 34, 37, 62, 69, 85, and 91; and bottom row residues 33, 37, 60 and 64. The molecular determinants that differentiate ChR1/VChR1 from ChR2/VChR2 are positioned at top row at residue 54; middle row at residue 93. Residues that are involved the in proton donor in bacteriorhodopsin (BR) are located in the middle row at residue 40 (D in BR but H in others). The residues that are in the positions of Glu194 and Glu204 in BR are located at bottom row, positions 42 and 52. A predicted glycosylation site for all ChRs is located on the middle row, at positions 43-45. There are also additional predicted glycosylation sites for CaChR1 and CyChR1 located on the top row, at position 2-3; for CrChR1 and CrChR2, there is also a site on the top row at positions 28-30, and CrChR1 has another on the middle row, at positions 49-51. Conserved residues known to be phosphorylated in ChR1 or ChR2 on the top row at positions 88, 89 and 96, as well as on the middle row at positions 3 and 7. Underlined characters show the regions that form transmembrane helices in bacteriorhodopsin (BR).

Two molecular determinants are conserved in ChR1/VChR1 and ChR2/VChR2 sequences, respectively, and shown to determine their different properties: 1) Glu87 (ChR1 numbering) in the predicted first helix is responsible for pH-dependent color tuning and fast channel inactivation of ChR1, as compared to ChR2; 2) Tyr226 (ChR1)/Asn187 (ChR2) in the predicted fifth helix confers differences in spectral sensitivity, inactivation and kinetics between ChR1 and ChR2. According to these criteria, the sequences identified in *C. augustae* and *C. yellowstonensis* belong to the ChR1/VChR1 class (FIG. 19). This placement is suggested by their red-shifted spectra (see below), characteristic of the ChR1/VChR1 class, as compared to the ChR2/VChR2 class. In contrast, the sequence from *C. raudensis* belongs to the ChR2/VChR2 class according to the two above-mentioned molecular determinants.

To distinguish the new *Chlamydomonas* channelopsins from the previously known ones from *C. reinhardtii*, species-specific abbreviations, i.e., CaChR1 for the *C. augustae* sequence, CyChR1 for that from *C. yellowstonensis*, and CrChR2 for the *C. raudensis* sequence. The original ChR1 and ChR2 are referred to as such, without modification for the source organism, because these sequences are already well-known under these names.

In the 7TM domain, residues at the active sites characteristic of other known channelopsins are conserved in all three new homologs. These include: 1) Glu in the position of the Schiff base proton acceptor (Asp85 according to bacteriorhodopsin (BR) numbering); 2) His in the position of the Schiff base proton donor (Asp96 in BR); 3) five Glu residues in or near the predicted second helix; and 4) Cys128 and Asp156 (ChR2 numbering) that form a predicted hydrogen bond between the third and fourth helices. Out of other residues known to form the retinal-binding pocket in BR, Tyr57, Gly122, Trp182, Asp212 and Lys216 (BR numbering) are conserved in new channelopsins, as they are in all previously known ones. Positions of Tyr185 and Trp189 (BR numbering) are occupied by Phe residues, as in all previously known channelopsins.

Figure 18:
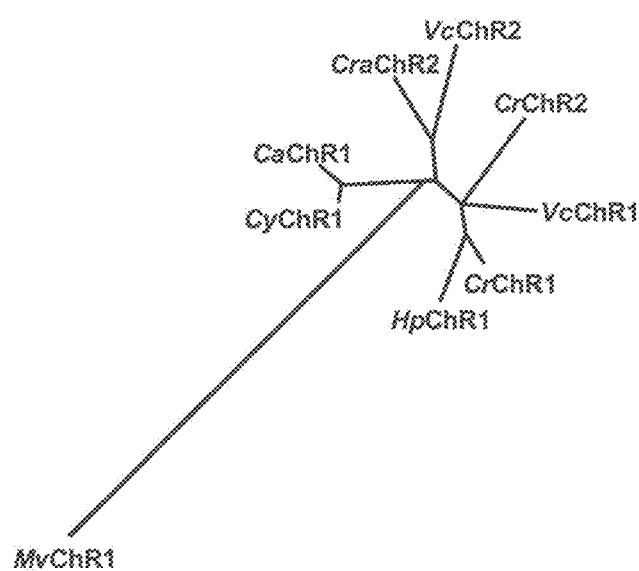
FIG. 18 illustrates a phylogenetic trees of the C-terminal domains of the so far known channelopsins constructed by the neighbor joining method. CrChR1, channelrhodopsin 1 from *C. reinhardtii*; CrChR2, channelrhodopsin 2 from *C. reinhardtii*; VcChR1, channelrhodopsin 1 from *V. carteri*; VcChR2, channelrhodopsin 2 from *V. carteri*; MvChR1, channelrhodopsin 1 from *M. viride*; CaChR1, channelrhodopsin 1 from *C. augustae*; CyChR1, channelrhodopsin 1 from *C. yellowstonensis*; CraChR2, channelrhodopsin 2 from *C. raudensis*; HpChR1 channelrhodopsin 1 from *Haematococcus pluvialis* (nucleotide Acc. No. JN596950).

Phylogeny of the C-terminal domain does not match that of the 7TM domain, although CaChR1 and CyChR1 again show close similarity (FIG. 18). No helices are predicted in the C-terminal domains of either of the new channelopsin sequences, in contrast to ChR1. As in other previously known channelrhodopsins, the C-terminal domains of the new channelopsins contain several highly conserved regions with no homology to any other so far known protein interspersed with repeats that vary in length and amino acid composition among different channelopsin variants. Long stretches of Gly-Met repeats and Met-rich regions are found in CaChR1 and CyChR1, and Gln repeats are found in all three new channelopsins. Such repeats, known as homopolymeric tracts, occur in many eukaryotic proteins and have been associated with protein-protein or protein-membrane interactions. A highly conserved region of about 40 residues at the very end of the C-terminal domains present in all so far known channelrhodopsins but MChR1 shows homology to domains in fibrinogen and ABC transporters that are responsible for protein multimerization and protein-protein interaction. In algal cells channelrhodopsins are confined to the membrane area above the eyespot and are associated with acetylated microtubules of the daughter four-membered flagellar rootlet.

The extracellular N-terminal regions of CaChR1 and CyChR1 contain a predicted conserved N-glycosylation site. Such sites, although at different positions, are also predicted in the N-termini of ChR1 and several other channelopsins, but not in CrChR2 (FIG. 19). Another such site conserved is located at the cytoplasmic end of the third predicted transmembrane helix. While not being bound by such theory, there may be a possible requirement for glycosylation for correct folding and targeting of channelrhodopsins may explain why no functional channelrhodopsin has been produced by expression in *E. coli*, despite many attempts. All three new channelopsin sequences lack an additional α-helix predicted in the N-terminus of ChR1 as a signal peptide, as do ChR2 and both VChR1 and VChR2. However, such helix is predicted in the sequence from *Haematococcus pluvialis*.

In ChR1 and ChR2 from *C. reinhardtii*, three and one phosphorylated residues, respectively, were identified by phosphoproteomics of the eyespot fractions. These residues are found in the cytoplasmic loop next to the 7TM domain that is highly conserved in all so far known channelopsin sequences, with the exception of MChR1. Out of the three phosphorylated residues of ChR1, Ser359 is conserved in all five *Chlamydomonas* channelopsins (FIG. 19), and the corresponding residue (Ser321) is the only phosphorylated site detected in ChR2. Thr374 is unique for ChR1 (with Val found at this site in other sequences), and Ser377 is conserved in four sequences with the conservative substitution in CrChR2 (FIG. 19).

Proteins from psychrophilic organisms show characteristic biases in amino acid composition, compared to their meso- and thermophilic homologs, that are believed to increase flexibility at low temperatures. Among these are decreased percentages of Pro, Arg and Ala residues, and an increased percentage of Ile residues. The same trends are observed in *Chlamydomonas* channelopsins: the combined percentages of Pro, Arg and Ala residues in the sequences of ChR1, CaChR1 and CyChR1 are 20%, 15.7% and 16%, respectively, whereas the percentages of Ile are 4.9%, 5.9% and 5.2%, respectively.

Example 11

Functional Characterization of *Chlaymydamonas* Channelopsins

HEK293 cells were transfected using the TransPass COS/293 transfection reagent (New England Biolabs, Ipswich, Mass.). All-trans-retinal (Sigma) was added as a stock solution in ethanol at the final concentration of 2.5 µM, unless otherwise indicated. Measurements were performed 48-72 h after transfection with an Axopatch 200B amplifier (Molecular Devices, Union City, Calif.). The signals were digitized with a Digidata 1440A using pClamp 10 software (both from Molecular Devices). Patch pipettes with resistances 2-5 MΩ were fabricated from borosilicate glass and filled with the following solution (in mM): KCl 126, $MgSO_4$ 2, $CaCl_2$ 0.5, EGTA 5, HEPES 25, pH 7.2. The bath solution contained (in mM): NaCl 150, $CaCl_2$ 1.8, KCl 4, $MgCl_2$ 1, glucose 5, HEPES 10, pH 7.4, unless otherwise indicated. For experiments at pH 9, Tris was used in the bath solution instead of HEPES. Unless otherwise indicated, the holding potential was −60 mV. Light excitation was provided by a Polychrome IV light source (T.I.L.L. Photonics GMBH, Grafelfing, Germany) pulsed with a mechanical shutter (Uniblitz Model LS6, Vincent Associates, Rochester, N.Y.; half-opening time 0.5 ms). The light intensity was attenuated with the built-in Polychrome system or with neutral density filters. Maximal quantum density at the focal plane of the 40× objective lens was ~$2 \times 10^{22}$ photons×$m^{-2}$.

Absorption spectroscopy. Absorption spectrum of partially purified CaChR1 in the UV-visible range was recorded on a Cary 4000 spectrophotometer (Varian, Palo Alto, Calif.).

Figure 20:
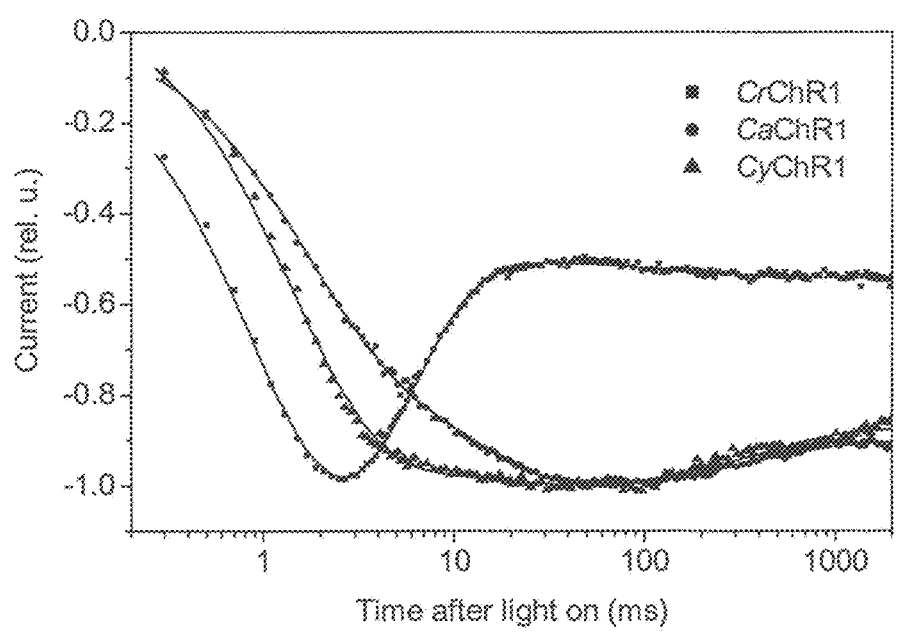
FIG. 20 illustrates typical kinetics of light-induced currents generated in HEK293 cells by CrChR1 from *C. raudensis* (squares), CaChR1 from *C. augustae* (circles) and CyChR1 from *C. yellowstonensis* (triangles). The currents in were normalized to the peak amplitude or the plateau level, respectively, and fitted with three exponential functions (solid lines). The excitation wavelength was 520 nm for CaChR1 and CyChR1, and 480 nm for ChR1, which corresponded to their spectral maxima. Bath pH was 7.4, $V_{hold}$ was −60 mV.

The 7TM domains of all three *Chlaymydamonas* channelopsins showed robust expression in the plasma membrane of HEK293 cells, as indicated by fluorescence of their EYFP-tags. CaChR1 and CyChR1 exhibited light-gated channel activity in this system, but no currents could be recorded upon expression of CrChR2. The kinetics of the currents generated by CaChR1 and CyChR1 were however quite different from that generated by ChR1. FIG. 20 shows typical signals recorded at the maximal light intensity under our standard conditions, i.e., bath pH 7.4, and holding potential ($V_{hold}$) −60 mV. Upon switching on the light, currents generated by ChR1 underwent a rapid initial rise with a time constant (τ) ~1 ms, reached a peak and rapidly (τ~5 ms) decreased under sustained illumination, i.e., inactivated to a lower level (FIG. 20, black line). In many cells the currents showed a subsequent slight increase with τ~200 ms. This behavior closely resembled the results reported for ChR1. In contrast, the rise of CaChR1- and CyChR1-generated currents was biphasic. The first rapid phase was similar to that of ChR1-generated currents, but it was followed by a slower rising phase with τ~20 ms (FIG. 20). The relative contributions of these two components varied from cell to cell. After reaching a peak, CaChR1- and CyChR1-generated currents exhibited very slow inactivation (τ~500 ms).

Figure 21:
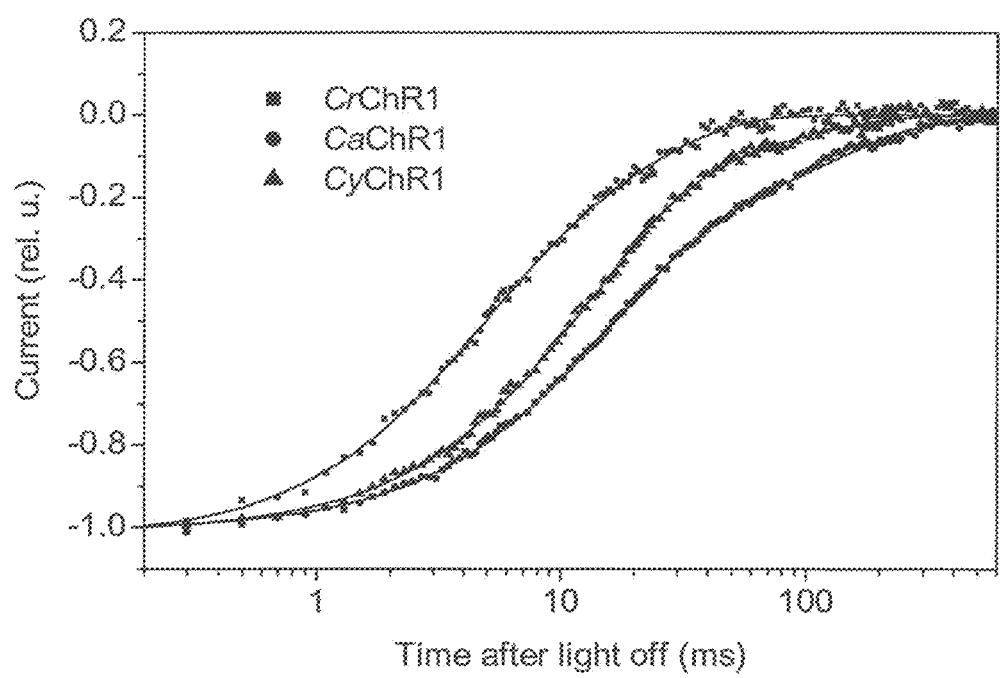
FIG. 21 illustrates typical kinetics of light-induced currents generated in HEK293 cells by CrChR1 from *C. raudensis* (squares), CaChR1 from *C. augustae* (circles) and CyChR1 from *C. yellowstonensis* (triangles). Decay of the currents seen in FIG. 20 after 2-s illumination. The currents were normalized to the peak amplitude or the plateau level, respectively, and fitted with two exponential functions (solid lines). The excitation wavelength was 520 nm for CaChR1 and CyChR1, and 480 nm for ChR1, which corresponded to their spectral maxima. Bath pH was 7.4, $V_{hold}$ was −60 mV.

For all three new *Chlaymydamonas* channelrhodopsin variants the response to the first flash showed a larger peak relative to the plateau level (measured at the end of the light pulse), which was not fully recovered even after 30 min dark interval, suggesting a contribution of a very slow adaptation process, or irreversible bleaching of an unstable fraction of the pigment. However, no difference was observed between responses to the second and all subsequent flashes recorded with 30 s dark intervals. Under these conditions, the peak to plateau ratio at the maximal light intensity was 1.7±0.2 (mean±SEM, n=8) for ChR1, close to the earlier reported results. For both CaChR1 and CyChR1 this ratio was significantly smaller: 1.2±0.1 (mean±SEM, n=12 and n=6, respectively). The absolute plateau amplitude was 101±25 pA (mean±SEM, n=8) for ChR1, 64±9 pA (mean±SEM, n=12) for CaChR1, and 49±13 pA (mean±SEM, n=6) for CyChR1. After switching off the light, the currents decayed biexponentially with τ~15 and ~120 ms for CaChR1, ~13 and ~150 ms for CyChR1, which was slower than ~4 and ~18 ms measured for ChR1 (FIG. 21), but close to that for ChR2.

The most widely used channelrhodopsin variant, ChR2, generates large enough currents in HEK cells even without the addition of exogenous retinal, indicating that its trace amount present in these cells is sufficient for reconstitution of functional protein. However, currents in cells transfected with the new channelrhodopsins or ChR1 were considerably smaller if no exogenous retinal was added: their plateau levels were only ~8% for CaChR1 and ~26% for ChR1 (data for CyChR1 are not shown), relative to the results obtained with the respective channelrhodopsins in the presence of 2.5 µM exogenous retinal.

Figure 22:
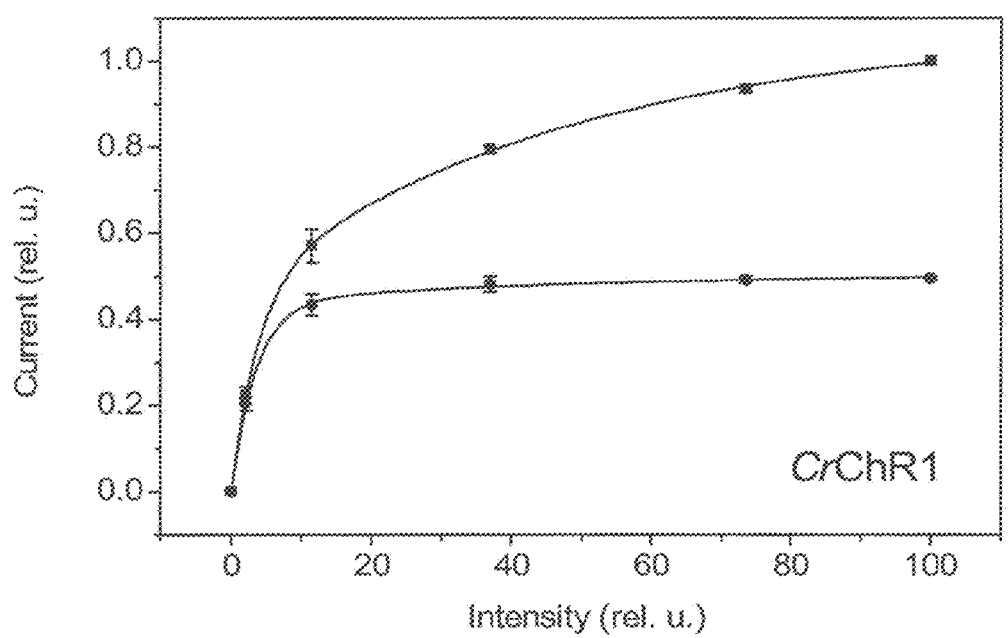
FIG. 22 illustrates the dependence of peak (squares) and plateau (circles) amplitudes on the stimulus intensity for currents generated by CrChR1 from *C. raudensis*. Data points are the mean normalized values±SEM (n=3).
Figure 23:
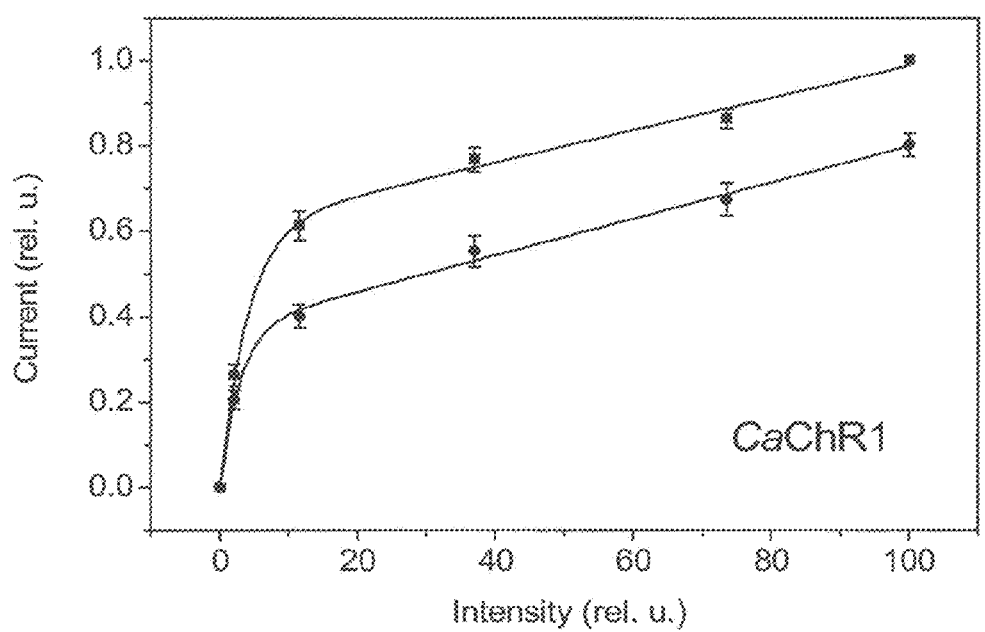
FIG. 23 illustrates the dependence of peak (squares) and plateau (circles) amplitudes on the stimulus intensity for currents generated by CaChR1 from *C. augustae*. Data points are the mean normalized values±SEM (n=5).

As described previously for ChR1-generated currents, the dependence of the plateau amplitude on the stimulus intensity saturated earlier than that of the peak (FIG. 22). In fact, the curve for the peak amplitude was biphasic and showed two levels of saturation, the first of which corresponded to that of the plateau level, whereas the second was at more than 10-fold higher light intensity. Therefore, the magnitude of light inactivation, calculated as the difference between the peak and plateau amplitudes relative to the peak amplitude, increased with light intensity and did not saturate even at the highest available intensities (FIG. 24, squares). In contrast, the curves for both peak and plateau amplitudes of CaChR1-generated currents consisted of two phases (FIG. 23), so that the magnitude of light inactivation reached the maximum at 10% maximal light intensity and then declined (FIG. 24, circles). Similar behavior was observed for CyChR1-generated currents (data not shown).

Figure 25:
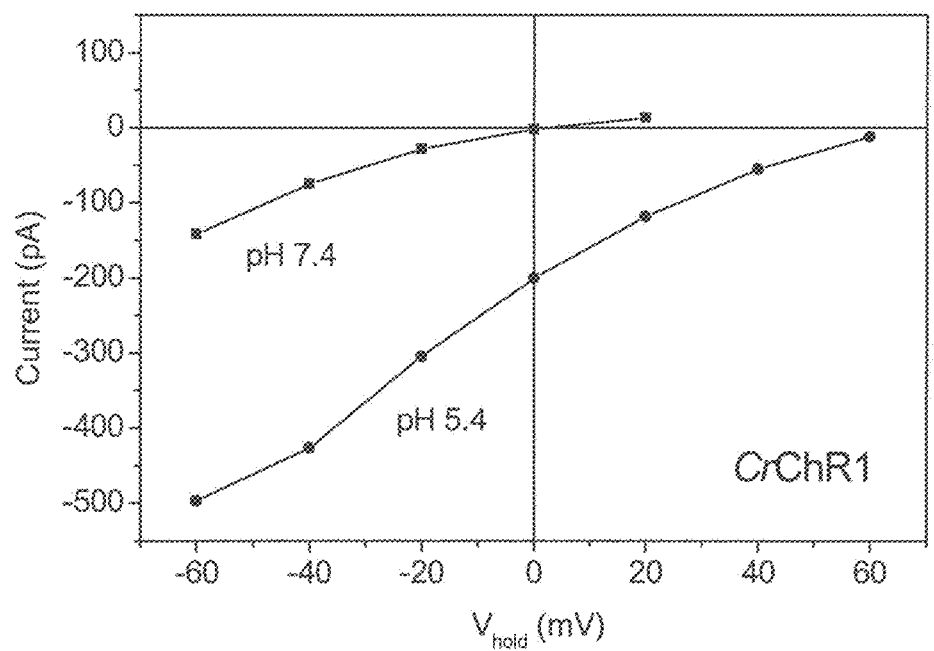
FIG. 25 illustrates typical current-voltage relationships (I-V curves) for the plateau level measured at the end of a 2-s excitation light pulse upon an increase of $V_{hold}$ in 20 mV steps from −60 mV at the bath pH 7.4 (squares) and 5.4 (circles) in HEK293 cells transfected with CrChR1 from *C. raudensis*. The wavelength was 480 nm for CrChR1, which corresponded to its spectral maxima.
Figure 26:
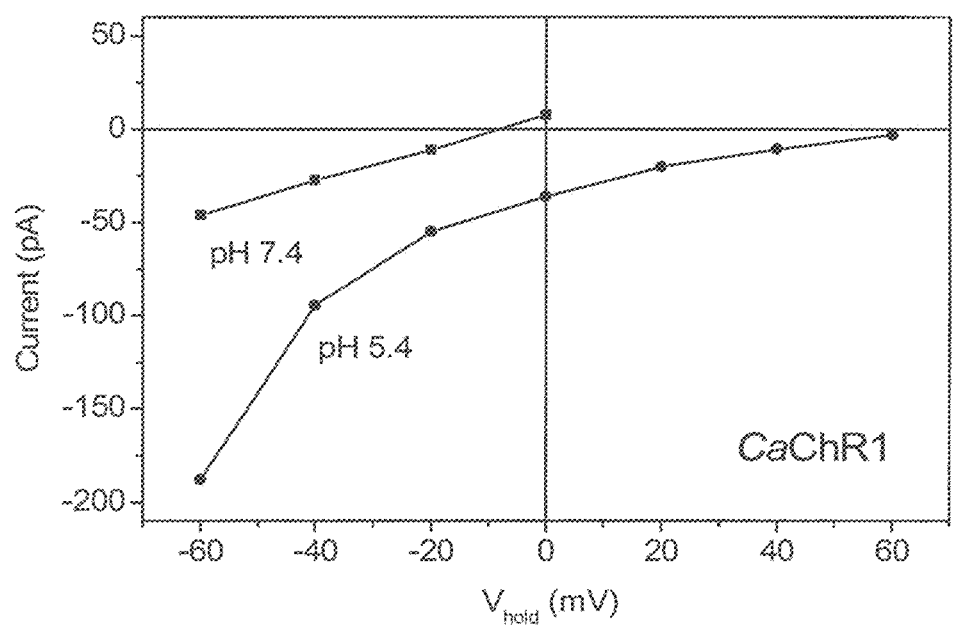
FIG. 26 illustrates typical current-voltage relationships (I-V curves) for the plateau level measured at the end of a 2-s excitation light pulse upon an increase of $V_{hold}$ in 20 mV steps from −60 mV at the bath pH 7.4 (squares) and 5.4 (circles) in HEK293 cells transfected with CaChR1 from *C. augustae*. The wavelength was 520 nm for CaChR1, which corresponded to its spectral maxima.
Figure 27:
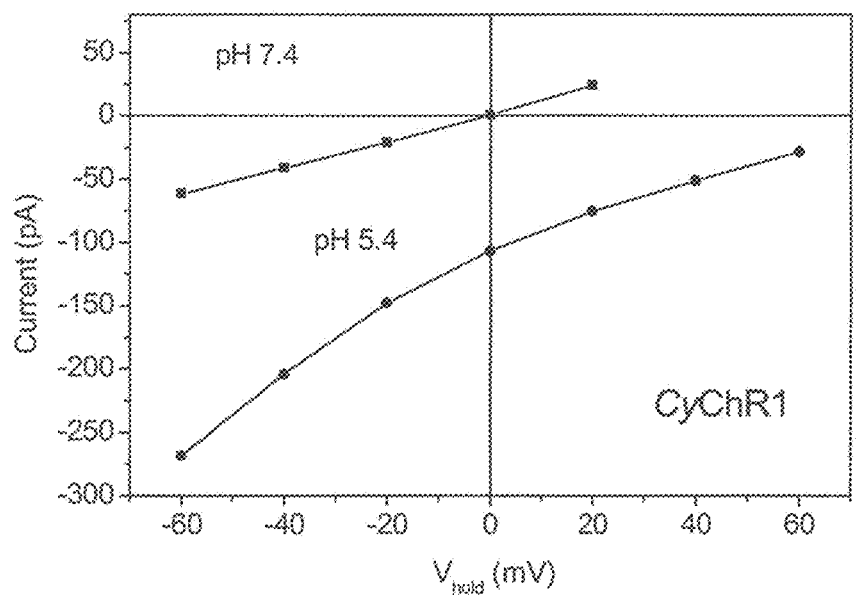
FIG. 27 illustrates typical current-voltage relationships (I-V curves) for the plateau level measured at the end of a 2-s excitation light pulse upon an increase of $V_{hold}$ in 20 mV steps from −60 mV at the bath pH 7.4 (squares) and 5.4 (circles) in HEK293 cells transfected with CyChR1 from *C. yellowstonensis*. The wavelength was 520 nm for CyChR1, which corresponded to its spectral maxima.
Figure 28:
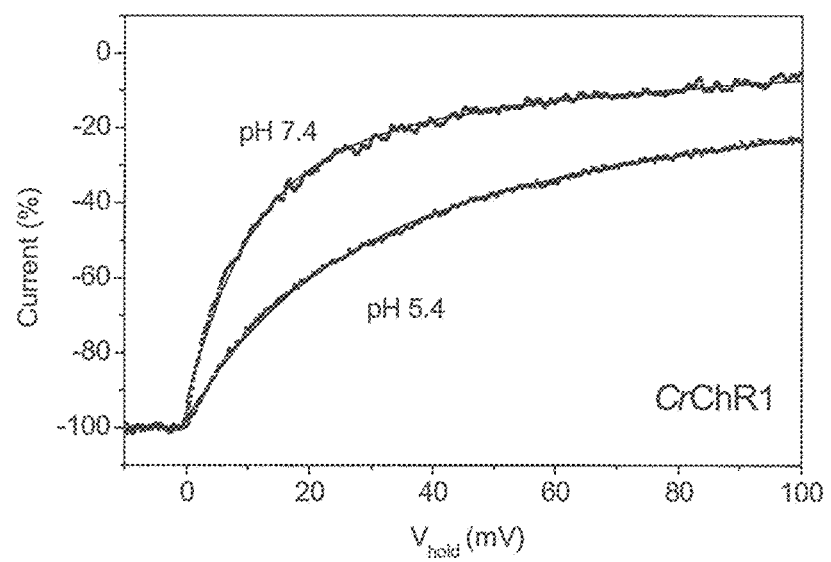
FIG. 28 illustrates normalized current decay traces recorded from cells transfected with CrChR1 from *C. raudensis* at holding potential ($V_{hold}$) −60 mV. Traces at the bath pH 7.4 or 5.4 were recorded from the same cell. Zero time corresponds to the end of a 2-s excitation light pulse.

CaChR1- and CyChR1-generated currents showed a typical dependence on the holding potential ($V_{hold}$) (FIGS. 25, 26 and 27). The reversal potentials ($V_r$) were similar to that for ChR1 and close to zero under our experimental conditions.

CaChR1 and CyChR1 were tested for proton permeability by measuring current-voltage relationships (I-V curves) under variable external pH to determine if they were highly proton-selective channels. Acidification of the external medium caused an increase in the current amplitude at a given voltage and a shift of the reversal potential to more positive values. The magnitude of this shift for CaChR1 and CyChR1 was similar to that for ChR1 (FIGS. 25, 26 and 27). Therefore, it can be concluded that both CaChR1 and CyChR1 are mostly selective for protons.

The rate of current decay after switching off the light increased slightly for both, CaChR1 and CyChR1 upon a change of the bath pH from 7.4 to 5.4 (FIGS. 29 and 30). This contrasts with reports for ChR1 that the rate of current decay after switching off the light decreases at acidic bath pH.

The spectral sensitivity of photocurrents was analyzed under low intensity light, as described in EXAMPLE 4 above. The spectral maxima for the new *Chlamydomonas* channelrhodopsins, CaChR1 and CyChR1, were at 520 nm at pH 7.4 (FIG. 32 and 32 black squares), which is 40 nm longer than that of the action spectrum of ChR1-generated currents in oocytes, and the absorption spectrum of purified ChR1 at neutral pH. To rule out a possible influence of a different expression system and/or a different algorithm of construction of the spectra, the action spectrum of currents generated by ChR1 in HEK cells was also measured. It showed a maximum at ~480 nm at pH 7.4 (FIG. 31, open triangles), but had a broad shape with significant absorption above 500 nm, indicating a contribution of the red-shifted deprotonated form of the pigment as was reported in oocytes. For both CaChR1 and CyChr1, the spectra measured at neutral (7.4) and acidic (5.4) pH were identical (FIGS. 31 and 32), in contrast to the spectrum of ChR1, which showed a significant red shift upon acidification of the medium. However, a small ~10 nm blue shift was observed upon the pH change from 7.4 to 9 for both CaChR1 and CyChR1 (FIGS. 31 and 32). The maximum of the action spectrum of photocurrents generated by ChR1 in native *C. reinhardtii* cells is 505 nm, whereas that of currents generated by ChR1 in heterologous systems at neutral pH is blue-shifted by at least 25 nm (FIG. 31). Expression of CaChR1 in *P. pastoris* in the presence of all-trans-retinal yielded photoactive pigment. The absorption spectrum of CaChR1 purified from *Pichia* exactly matched the action spectrum of photocurrents generated by this pigment in HEK cells, which indicated that its native state was essentially preserved in detergent (FIG. 33).

Example 12

Cloning and Expression in Yeast

Expression and purification from *Pichia*. The 7TM domain of CaChR1 (1-352 residues) was cloned into the pPIC9K vector (Invitrogen, Carlsbad, Calif.) between EcoRI and NotI sites in frame with two TEV protease sites at the N-terminus and before a C-terminal 6His-tag. The resultant plasmid was linearized with BspEI and transformed into the *P. pastoris* SMD1168 (his4, pep4) strain by electroporation according to the manufacturer's instructions. First, transformants were screened for plasmid integration by their ability to grow on hystidine-deficient plates, and second, for multiple inserts by their geneticin resistance. A single colony that grew on 4 mg/mL geneticin was selected. A starter culture was inoculated in 500 mL BMMY (buffered minimal methanol yeast) medium. Expression was induced by the addition of 0.5% methanol every 24 h in the presence of 30 µM all-trans-retinal. Cells were grown for two days, harvested by low-speed centrifugation and disrupted by a bead beater. Membrane fragments were collected by centrifugation for 1 h at 48,000 rpm and solubilized by incubation with 2% dodecyl maltoside for 1 h. The protein was purified on a Ni-NTA agarose column (Qiagen, Hilden, Germany). The protein yield was 6.4 mg/L of culture, as estimated from absorbance at 520 nm.

Enhancement of Long-Wavelength Sensitivity of Optogenetic Microbial Rhodopsins

Example 13-A1

Archaerhodopsin from Halorubrumsodomense (AR-3)

To determine the effect of A2 retinal on the proton pump AR-3 expressed in *E. coli* cells, since this expression system allows quantitative measurements of absorption and fast charge movements within rhodopsin molecules. To do this, AR-3 was expressed in the presence of A1 or A2 retinal. The AR-3 coding sequence was received from Dr. E. S. Boyden (Massachusetts Institute of Technology, Boston, Mass.) and expressed in *E. coli* cells as described earlier for other microbial rhodopsins (see Jung, K.-H., Trivedi, V. D., and Spudich, J. L. Demonstration of a sensory rhodopsin in eubacteria, *Mol. Microbiol.* 47, 1513-1522, 2003 and Wang, W.-W., Sineshchekov, O. A., Spudich, E. N., and Spudich, J. L. Spectroscopic and photochemical characterization of a deep ocean proteorhodopsin, *J. Biol. Chem.* 278, 33985-33991, 2003) in the presence of 5 ul of all-trans A1 retinal (Sigma), or all-trans A2 retinal (at least 99% pure as tested by HPLC; a gift from Dr. R. K. Crouch, Medical University of South Carolina, Charleston, S.C. —but also available from, for example, Toronto Research Chemicals, Ontario, Canada). Cells were washed in distilled water and transferred to low-ionic strength medium (in mM): NaCl 1.5, $CaCl_2$ 0.15, $MgCl_2$ 0.15, Tris 5, pH 7.2. Absorption spectra were recorded on a Cary 4000 spectrophotometer with integrating sphere (Varian, Palo Alto, Calif.). Absorption spectrum of cells without induction of expression was subtracted from those expressing A1- or A2-reconstituted AR-3 to correct for scattering and intrinsic protein absorption. Photocurrents in suspension of the cells were generated by 8 ns laser flash applied along the direction between two platinum electrodes (as described in Sineshchekov, O., and Spudich, J. Light-induced intramolecular charge movements in microbial rhodopsins in intact *E. coli* cells, *Photochem. Photobiol. Sci.* 3, 548-554, 2004).

The absorption spectra, corrected for light scattering and minor differences in the amount of cytochromes caused by expression of a foreign protein are presented in FIG. 34. The absorption maximum of the A2-reconstituted pigment was 35-nm red-shifted from that of the A1-reconstituted AR-3 (558 nm to 593 nm). The shift of the wavelength of half-maximal absorption on the red slope of the spectra was even greater, 40 nm (from 599 to 639 nm). This may indicate the expected widening of the band with its shift to longer wavelengths, as has been noted previously in animal visual pigments reconstituted with A2 retinal (Bridges, C. D. Spectroscopic properties of porphyropsins, *Vision Res.* 7, 349-369, 1967). A poorly resolved shoulder was observed on the short-wavelength slope of the spectrum of the A2-reconstituted pigment. This shoulder may indicate a very small amount of A1 retinal contamination. However, its position was at a shorter wavelength than the maximum of the A1-reconstituted spectrum.

The pigments reconstituted with A1 and A2 retinals demonstrated very similar kinetics of intramolecular charge movements with a slightly faster decay of the fast current associated with proton transfer to the acceptor, which corresponds to formation of the M intermediate (the current traces in FIG. 35), and slightly slower reprotonation of the Schiff base (better resolved in the charge traces in FIG. 35). The absolute amplitude of the fast photocurrent was ~3-fold lower in the sample incubated with A2 retinal, which correlates roughly with the 2-fold lower expression and faster decay kinetics. Thus, the absolute quantum yields of proton transport in the A1 and A2 forms appear to be comparable.

The spectral sensitivity of photoelectric responses in *E. coli* cells as well as in HEK293 cells was measured at very low light intensities (in the range where the dependence was close to linear) to avoid distortion and facilitate correction for the number of photons.

Whole-cell patch clamp recording in HEK293 cells: HEK293 (human embryonic kidney) cells were transfected using the TransPass COS/293 transfection reagent (New England Biolabs, Ipswich, Mass.). A1 all-trans-retinal (Sigma) was added as a stock solution in ethanol at the final concentration of 2.5 µM. A2 all-trans-3,4-dehydroretinal (>99% pure as tested by HPLC; a gift from Dr. R. K. Crouch, Medical University of South Carolina, Charleston, S.C.) was added at a final concentration of 5 µM. Measurements were performed 48-72 h after transfection with an Axopatch 200B amplifier (Molecular Devices, Union City, Calif.). The signals were digitized with a Digidata 1440A using pClamp 10 software (both from Molecular Devices). Patch pipettes with resistances of 2-5 MΩ were fabricated from borosilicate glass and filled with the following solution (in mM): KCl 126, $MgCl_2$ 2, $CaCl_2$ 0.5, EGTA 5, HEPES 25, pH 7.4. The bath solution contained (in mM): NaCl 150, $CaCl_2$ 1.8, $MgCl_2$ 1, glucose 5, HEPES 10, pH 7.4. The holding potential was −60 mV. Light excitation was provided by a Polychrome IV light source (T.I.L.L. Photonics GMBH, Grafelfing, Germany) pulsed with a mechanical shutter (Uniblitz Model LS6, Vincent Associates, Rochester, N.Y.; half-opening time 0.5 ms). The light intensity was attenuated with the built-in Polychrome system or with neutral density filters. Maximal quantum density at the focal plane of the 40× objective lens was ~$2\times10^{22}$ photons×m$^{-2}$.

In the case of continuous light excitation of HEK293 cells only the initial part of the current signals up to 20 ms was measured to minimize the involvement of possible photoreactions of photocycle intermediates. Photocurrents were normalized according to the number of photons in each laser flash or light pulse.

In full agreement with the difference in the absorption spectra, the action spectrum of the charge movement in A2-reconstituted AR-3 is red-shifted by ~35 nm with the half-maximum efficiency at >640 nm (FIG. 36, solid symbols, solid lines). This confirms that the charge movement registered in a suspension of *E. coli* cells is generated by the A2-reconstituted fraction of AR-3, and not by the fraction reconstituted with trace amounts of A1 retinal. A similar shoulder at ~540 nm as observed in the absorption spectrum is apparent in the action spectrum.

A1- and A2-reconstituted AR-3 were compared expressed in HEK293 cells. An excess amount (5 uM) of A2 retinal was added, because HEK cells are known to contain endogenous A1 retinal). Light-induced hyperpolarizing currents of A2-reconstituted AR-3 did not significantly differ in the amplitudes and kinetics of corresponding currents generated by AR-3 reconstituted with A1 retinal (data not shown). When the cells were incubated with A1 or A2 retinal for two days, the spectra for the photocurrents in HEK cells were essentially identical to the action spectra of charge movement measured in *E. coli* cells (FIG. 36, open symbols, dashed lines). However, on the third day of incubation of HEK293 cells with A2-retinal the maximum of the action spectra shifted to shorter wavelengths and a clear band corresponding to the maximum of the action spectrum of A1-reconstituted AR-3 appeared (FIG. 37, solid symbols, thick solid line). An increased relative contribution of the A1 pigment as compared to the A2 pigment upon an increase in the incubation time is obvious from the difference spectra (thin solid line in FIG. 37).

The increase in the amount of AR-3 reconstituted with endogenous A1 between day 2 and day 3 is most probably due to activation of its synthesis by the excess of A2 retinal. A similar, but even more pronounced effect was observed in channelrhodopsins.

Example 14

Channelrhodopsin-2 from *Chlamydomonas Reinhardtii* (CrChR2)

CrChR2, which activates neuron firing, is the most widely used optogenetic tool because of its high ion conductance and/or expression level in animal cells. The major disadvantage of CrChR2 is its short-wavelength absorption with a long-wavelength half-maximal efficiency at ~500 nm (squares in FIG. 38). Incubation of HEK293 cells transfected with CrChR2 with A2 retinal caused significant changes in the action spectrum of light-induced currents (circles in FIG. 38). The overall shape of the spectrum clearly indicates contribution of two pigment species in current generation. The strongly pronounced shoulder above 500 nm may be due to A2-reconstituted CrChR2, whereas the structured short-wavelength slope reflects a significant contribution of A1-reconstituted CrChR2. This contribution is stronger than in the case of AR-3, and contrary to the pump appears already after 2 days of incubation of HEK cells with A2 retinal. This more rapid appearance suggests a greater difference between affinities to A1 and A2 retinal in CrChR2, as compared to AR-3.

To characterize the absorption properties of A2-reconstituted CrChR2, the action spectrum of pure A1-reconstituted CrChR2 (squares in FIG. 38) was subtracted and multiplied by different coefficients, from the action spectrum obtained after incubation with A2-retinal (circles). The most spectrally reasonable difference curve (dashed line in FIG. 38) was obtained assuming that the photoelectric response sensitized by CrChR2 reconstituted with endogenous A1 comprises about 30% of the combined action of the A1- and A2-reconstituted pigments. The deduced spectrum of pure A2-reconstituted ChR2 was wider than that of the A1-reconstituted form, as would be predicted from its longer absorption. It lacked the fine structure evident in the A1 pigment and had a maximum at ~508 nm, i.e. at 35 nm longer wavelength than the A1-reconstituted pigment.

Despite the significant contribution of the A1 retinal-reconstituted form of CrChR2, the addition of A2 retinal produces a red shift in spectral sensitivity (assessed by the wavelength of half-maximal response) by >30 nm. However, the A1 and A2-reconstituted CrChR2 appear to be comparable since photoelectric currents induced by green light absorbed only by the A2 form reach similar high values (above 1 nA, FIG. 39A) as the A1 pigment. Correct comparison of the kinetics of the photocurrents generated by A1- and A2-reconstituted CrChR2 can only be done at low light intensities to avoid saturation effects in the system of two pigments with overlapping absorption. As shown in FIG. 39B, photocurrents generated in response to 440 nm light (absorbed primarily by the A1 form), and to 530 nm light (absorbed essentially only by the A2 form) are almost identical. In summary, substitution of A1 retinal with A2 retinal does not significantly affect the channel properties of CrChR2, but shifts its absorption by 35 nm to the red.

Channelrhodopsin-1 from *Chlamydomonas reinhardtii* (CrChR1): Another *C. reinhardtii* channelrhodopsin, CrChR1, mediates phototaxis in native algal cells with a maximum at 505 nm. However, upon expression in animal cells the absorption spectra of CrChR1 at neutral pH peaks at a much shorter wavelength (485 nm at pH 7.4 under our experimental conditions). Incubation of HEK cells transfected with CrChR1 with A2 retinal shifted the main maximum of the action spectrum by ~30 nm to 515 nm. Simultaneously, a strongly pronounced shoulder at ~555 nm appeared in the action spectrum. This shoulder can be interpreted as the appearance of the protonated form of CrChR1, which with A1 retinal was observed only at low pH and had a maximum at 500-505 nm. Thus, substitution of A1 retinal by A2 retinal not only shifted the spectral maxima of both the deprotonated and protonated forms of CrChR1, but also shifted the $pK_a$ of the Schiff base counterion to higher values. A similar effect of A2 on the pKa of a color transition has been reported earlier in bacteriorhodopsin. As a combined result of these two effects, the wavelength of half-maximal efficiency of the long-wavelength of CrChR1 was shifted upon incubation with A2 retinal by 45 nm from that of the A1 retinal-reconstituted pigment. The dashed line in FIG. 40 illustrates the deduced absorption spectrum of A2-reconstituted CrChR1 assuming that the photoelectric response sensitized by A1-reconstituted CrChR1 comprises about 30% of the combined action of A1- and A2-reconstituted pigments.

New Long-Wavelength Channelrhodopsins from *Chlamydomonas augustae* (CaChR1) and *Mesostigma viride* (MvChR1):

CaChR1 is a channerhodopsin variant recently identified in the psychrophilic species *C. augustae*. In contrast to CrChR1, its maximal absorption at neutral pH is at 520 nm. MvChR1 from *M. viride* is to date the most red-shifted native channelrhodopsin, with a peak sensitivity at neutral pH at ~530 nm. The addition of A2 retinal to HEK cells transfected with CaChR1 or MvChR1 led to the appearance of strongly red-shifted pigment forms obvious from the shape of the action spectra (FIGS. 41 and 42). The long-wavelength slope of the CaChR1 spectrum was shifted to 589 nm at the level of 50% efficiency, more than 20 nm from that measured with A1 retinal, whereas the position of the maximum shifted to a smaller degree. In the case of MvChR1, reconstitution with A2 retinal shifted the long-wavelength slope of the spectrum by >40 nm, as compared to that measured upon reconstitution with A1 retinal.

In some embodiments, the long-wavelength sensitivity of optogenetic microbial rhodopsins is enhanced using 3,4-Dehydroretinal (A2 retinal). As described herein, the proton pump AR-3 and four tested channelrhodopsin variants, CrChR1, CrChR2, CaChR1 and MvChR1, incorporated A2 retinal and produced functional proteins, the spectral sensitivity of which was significantly red-shifted from those of the corresponding A1 retinal pigments. Such spectral shifts are expected to be beneficial for optogenetic applications, especially in live animals, because light scattering decreases with the increase of wavelength. However, light scattering is not the only factor to consider; another, especially significant in brain tissue studies, is absorption by hemoglobin. Out of all tested channelrhodopsins, only CaChR1 and MvChR1 reconstituted with A2 retinal showed significant sensitivity to wavelengths above the long-wavelength boundary of hemoglobin absorption (FIG. 43).

To estimate the potential benefits of the use of A2 retinal in neuroscience optogenetic applications, the total number of actinic photons absorbed by the corresponding A2 and A1 pigments over the visible spectral range at different depths of brain tissue was calculated. The action spectra of photocurrents recorded in HEK293 cells that express the corresponding opsins incubated with A1 or A2 retinal were multiplied by the spectral distribution of light intensities derived from absolute values of light attenuation by brain tissue. The area under resultant curves proportional to the number of photons absorbed by each pigment was plotted in FIG. 44 as a function of the distance from the brain surface. The curves were normalized to the values at the surface to compare attenuation of actinic light for different pigments.

Based on this calculation the total absorption of short-wavelength channelrhodopsins (CrChR2 and CrChR1 deprotonated at neutral pH) will decrease sharply within the tissue. Moreover, substitution of A2 for A1 in CrChR2 will not improve significantly the situation, because a decrease in light scattering is compromised by an increase in hemoglobin absorption. In contrast, substitution of A2 for A1 in CrChR1 significantly increases the penetration depth of actinic light. However, this improvement is mostly due to a contribution of the protonated form of CrChR1, which in A2-reconstituted pigment appears at the neutral pH and has an absorption maximum above 550 nm (FIG. 40), i.e., ~45 nm red-shifted as compared to the protonated form of A1-reconstituted CrChR1 observed at low pH.

According to calculations, all tested rhodopsins with red-shifted absorption (CaChR1, MvChR1, and AR-3) are expected to permit optogenetic activation in deep layers, even when bound to A1 retinal. Substitution of A2 for A1 retinal in these rhodopsins will increase their efficiency significantly (FIG. 44). The greatest calculated effect was for MvChR1. At 1 cm depth the total number of photons absorbed by A2-bound pigment will be 13-fold greater than that absorbed by A1-bound pigment.

These measurements demonstrate that A2 retinal can be efficiently used to improve the performance of optogenetic tools in cultured cells, and the calculations above show that the benefits will be even greater for intact tissues. Therefore, in some embodiments, A2 retinal may be used in living animals, it has been demonstrated that when vitamin A-deprived rats received intraperitoneal injection of a retinal analog there was rapid incorporation of the synthetic retinoid into a major fraction of available opsin. This is the first instance of the use of retinal A to shift the absorption spectra of ontogenetic analogs.

The action spectra of photocurrents measured in HEK293 cells incubated with A2 retinal showed a rather prominent contribution of A1-reconstituted pigments. This contribution is unlikely to be due to incorporation of trace amounts of A1 retinal in our A2 retinal stock, because: (i) no obvious A1-derived band appeared in A2-reconstituted AR-3 produced in *E. coli* cells (FIGS. 35 and 36); (ii) the contribution of the A1-derived form in HEK293 cells increased with time (FIG. 37). The latter observation also cannot be explained by incorporation of endogenous A1 retinal present in HEK293 cells, as only very small currents could be recorded in control experiments in these cells without the addition of retinoids. This suggests that in HEK cells exogenous A2 retinal is partially converted to A1 retinal or activates biosynthesis of A1 retinal. It is noteworthy that the amplitudes of spectral shifts upon substitution of A1 with A2 retinal reveal a significant difference between channelrhodopsins and other microbial rhodopsins. The magnitude of the spectral shift in AR-3 is very close to the shifts measured earlier in other long-wavelength microbial rhodopsins ($\leq 1,000$ cm$^{-1}$). In contrast, spectral shifts of all channelrhodopsins (or their protonated forms, as in the case of CrChR1) are significantly larger, in the range between ~1,300 and ~1,800 cm$^{-1}$ (FIG. 45). These shifts are also larger than the shifts measured in animal visual pigments that exist in both A1- and A2-bound forms in vivo, indicating structural differences in the retinal binding pockets in channelrhodopsins compared to other microbial rhodopsins.

REFERENCES

The following literature citations as well as those cited above are incorporated by reference to the extent that they support the present disclosure.

Sineshchekov, O. A., K.-H. Jung, and J. L. Spudich. 2002. Two rhodopsins mediate phototaxis to low- and high-intensity light in *Chlamydomonas reinhardtii*. Proc. Natl. Acad. Sci. USA. 99:8689-8694.

Nagel, G., D. Ollig, M. Fuhrmann, S. Kateriya, A. M. Musti, E. Bamberg, and P. Hegemann. 2002. Channelrhodopsin-1: a light-gated proton channel in green algae. Science. 296:2395-2398.

Nagel, G., T. Szellas, W. Huhn, S. Kateriya, N. Adeishvili, P. Berthold, D. Ollig, P. Hegemann, and E. Bamberg. 2003. Channelrhodopsin-2, a directly light-gated cation-selective membrane channel. Proc. Natl. Acad. Sci. USA. 100:13940-13945.

Suzuki, T., K. Yamasaki, S. Fujita, K. Oda, M. Iseki, K. Yoshida, M. Watanabe, H. Daiyasu, H. Toh, E. Asamizu, S. Tabata, K. Miura, H. Fukuzawa, S. Nakamura, and T. Takahashi. 2003. Archaeal-type rhodopsins in *Chlamydomonas*: model structure and intracellular localization. Biochem. Biophys. Res. Commun. 301:711-717.

Zhang, F., M. Prigge, F. Beyriere, S. P. Tsunoda, J. Mattis, O. Yizhar, P. Hegemann, and K. Deisseroth. 2008. Red-shifted optogenetic excitation: a tool for fast neural control derived from *Volvox carteri*. Nat. Neurosci. 11:631-633.

Kianianmomeni, A., K. Stehfest, G. Nematollahi, P. Hegemann, and A. Hallmann. 2009. Channelrhodopsins of *Volvox carteri* are photochromic proteins that are specifically expressed in somatic cells under control of light, temperature, and the sex inducer. Plant. Physiol. 151:347-366.

Spudich, J. L., C.-S. Yang, K.-H. Jung, and E. N. Spudich. 2000. Retinylidene proteins: structures and functions from archaea to humans. Annu Rev. Cell Dev. Biol. 16:365-392.

Boyden, E. S., F. Zhang, E. Bamberg, G. Nagel, and K. Deisseroth. 2005. Millisecond-timescale, genetically targeted optical control of neural activity. Nat. Neurosci. 8:1263-1268.

Li, X., D. V. Gutierrez, M. G. Hanson, J. Han, M. D. Mark, H. Chiel, P. Hegemann, L. T. Landmesser, and S. Herlitze. 2005. Fast noninvasive activation and inhibition of neural and network activity by vertebrate rhodopsin and green algae channelrhodopsin. Proc. Natl. Acad. Sci. USA. 102:17816-17821.

Nagel, G., M. Brauner, J. F. Liewald, N. Adeishvili, E. Bamberg, and A. Gottschalk. 2005. Light activation of channelrhodopsin-2 in excitable cells of *Caenorhabditis elegans* triggers rapid behavioral responses. Curr. Biol. 15:2279-2284.

Deisseroth, K. 2011. Optogenetics. Nat. Methods. 8:26-29.

Lin, J. Y. 2010. A user's guide to channelrhodopsin variants: features, limitations and future developments. Exp. Physiol. 96:19-25.

Hegemann, P., and A. Moglich. 2011. Channelrhodopsin engineering and exploration of new optogenetic tools. Nat. Methods. 8:39-42.

Bamann, C., T. Kirsch, G. Nagel, and E. Bamberg. 2008. Spectral characteristics of the photocycle of channelrhodopsin-2 and its implication for channel function. J. Mol. Biol. 375:686-694.

Ishizuka, T., M. Kakuda, R. Araki, and H. Yawo. 2006. Kinetic evaluation of photosensitivity in genetically engineered neurons expressing green algae light-gated channels. Neurosci. Res. 54:85-94.

Tsunoda, S. P., and P. Hegemann. 2009. Glu 87 of channelrhodopsin-1 causes pH-dependent color tuning and fast photocurrent inactivation. Photochem. Photobiol. 85:564-569.

Feldbauer, K., D. Zimmermann, V. Pintschovius, J. Spitz, C. Bamann, and E. Bamberg. 2009. Channelrhodopsin-2 is a leaky proton pump. Proc. Natl. Acad. Sci. USA. 106:12317-12322.

Lin, J. Y., M. Z. Lin, P. Steinbach, and R. Y. Tsien. 2009. Characterization of engineered channelrhodopsin variants with improved properties and kinetics. Biophys. J. 96:1803-1814.

Wang, H., Y. Sugiyama, T. Hikima, E. Sugano, H. Tomita, T. Takahashi, T. Ishizuka, and H. Yawo. 2009. Molecular determinants differentiating photocurrent properties of two channelrhodopsins from *Chlamydomonas*. J. Biol. Chem. 284:5685-5696.

Berndt, A., O. Yizhar, L. A. Gunaydin, P. Hegemann, and K. Deisseroth. 2009. Bi-stable neural state switches. Nat. Neurosci. 12:229-234.

Gunaydin, L. A., O. Yizhar, A. Berndt, V. S. Sohal, K. Deisseroth, and P. Hegemann. 2010. Ultrafast optogenetic control. Nat. Neurosci. 13:387-392.

Wen, L., H. Wang, S. Tanimoto, R. Egawa, Y. Matsuzaka, H. Mushiake, T. Ishizuka, and H. Yawo. 2010. Opto-current-clamp actuation of cortical neurons using a strategically designed channelrhodopsin. PLoS One. 5:e12893.

Govorunova, E. G., K.-W. Jung, O. A. Sineshchekov, and J. L. Spudich. 2004. *Chlamydomonas* sensory rhodopsins A and B: Cellular content and role in photophobic responses. Biophys. J. 86:2342-2349.

Berthold, P., S. P. Tsunoda, O. P. Ernst, W. Mages, D. Gradmann, and P. Hegemann. 2008. Channelrhodopsin-1 initiates phototaxis and photophobic responses in *Chlamydomonas* by immediate light-induced depolarization. Plant Cell. 20:1665-1677.

Litvin, F. F., O. A. Sineshchekov, and V. A. Sineshchekov. 1978. Photoreceptor electric potential in the phototaxis of the alga *Haematococcus pluvialis*. Nature. 271:476-478.

Harz, H., and P. Hegemann. 1991. Rhodopsin-regulated calcium currents in *Chlamydomonas*. Nature. 351:489-491.

Sineshchekov, O. A., E. G. Govorunova, A. Der, L. Keszthelyi, and W. Nultsch. 1992. Photoelectric responses in phototactic flagellated algae measured in cell suspension. J. Photochem. Photobiol. B: Biol. 13:119-134.

Melkonian, M. 1983. Functional and phylogenetic aspects of the basal apparatus in algal cells. J. Submicrosc. Cytol. 15:121-125.

Rodriguez-Ezpeleta, N., H. Philippe, H. Brinkmann, B. Becker, and M. Melkonian. 2007. Phylogenetic analyses of nuclear, mitochondrial, and plastid multigene data sets support the placement of *Mesostigma* in the Streptophyta. Mol. Biol. Evol. 24:723-731.

Nikolic, K., N. Grossman, M. S. Grubb, J. Burrone, C. Toumazou, and P. Degenaar. 2009. Photocycles of channelrhodopsin-2. Photochem. Photobiol. 85:400-411.

Sineshchekov, O. A., and J. L. Spudich. 2005. Sensory rhodopsin signaling in green flagellate algae. In Handbook of Photosensory Receptors. Briggs, W. R., and Spudich, J. L., editors. Wiley-VCH, Weinheim. 25-42.

Sineshchekov, O. A., F. F. Litvin, and L. Keszthelyi. 1990. Two components of photoreceptor potential of the flagellated green alga *Haematococcus pluvialis*. Biophys. J. 57:33-39.

Sineshchekov, O. A. 1991. Photoreception in unicellular flagellates: bioelectric phenomena in phototaxis. In Light in Biology and Medicine. Douglas, R. D., editor. Plenum Press, New York. 523-532.

Sineshchekov, O. A., and E. G. Govorunova. 1999. Rhodopsin-mediated photosensing in green flagellated algae. Trends Plant Sci. 4:58-63.

Sineshchekov, O. A., and E. G. Govorunova. 2001. Electrical events in photomovements of green flagellated algae. In Comprehensive Series in Photosciences. Hader, D.-P., and Lebert, M., editors. Elsevier, Amsterdam. 245-280.

Matsunaga S, W. S., Sakaushi S, Miyamura S, Hori T. 2003. Screening effect diverts the swimming directions from diaphototactic to positive phototactic in a disk-shaped green flagellate *Mesostigma viride*. Photochem. Photobiol. 77:324-332.

Ernst, O. P., P. A. Sanchez Murcia, P. Daldrop, S. P. Tsunoda, S. Kateriya, and P. Hegemann. 2008. Photoactivation of channelrhodopsin. J. Biol. Chem. 283:1637-1643.

Hegemann, P., S. Ehlenbeck, and D. Gradmann. 2005. Multiple photocycles of channelrhodopsin. Biophys. J. 89:3911-3918.

Radu, I., C. Bamann, M. Nack, G. Nagel, E. Bamberg, and J. Heberle. 2009. Conformational changes of channelrhodopsin-2. J. Am. Chem. Soc. 131:7313-7319.

Nack, M., I. Radu, M. Gossing, C. Bamann, E. Bamberg, G. F. von Mollard, and J. Heberle. 2010. The DC gate in Channelrhodopsin-2: crucial hydrogen bonding interaction between C128 and D156. Photochem. Photobiol. Sci. 9:194-198.

Bamann, C., R. Gueta, S. Kleinlogel, G. Nagel, and E. Bamberg. 2010. Structural guidance of the photocycle of channelrhodopsin-2 by an interhelical hydrogen bond. Biochemistry. 49:267-278.

Iseki, N., S. Matsunaga, A. Murakami, K. Ohno, K. Shiga, K. Yoshida, M. Sugai, T. Takahashi, T. Hori, and M. Watanabe. 2002. A blue-light-activated adenylyl cyclase mediates photoavoidance in Euglena gracilis. Nature. 415:1047-1051.

Witman, G. B. 1993. *Chlamydomonas* phototaxis. Trends Cell Biol. 3:403-408.

Kreimer, G. 1994. Cell biology of phototaxis in flagellate algae. Int. Rev. Cytol. 148:229-310.

Sineshchekov, O. A., E. G. Govorunova, and J. L. Spudich. 2009. Photosensory functions of channelrhodopsins in native algal cells. Photochem Photobiol. 85:556-563.

Hegemann, P. 2008. Algal sensory photoreceptors. Annu Rev. Plant. Biol. 59:167-189.

Sugiyama, Y., H. Wang, T. Hikima, M. Sato, J. Kuroda, T. Takahashi, T. Ishizuka, and H. Yawo. 2009. Photocurrent attenuation by a single polar-to-nonpolar point mutation of channelrhodopsin-2. Photochem. Photobiol. Sci. 8:328-336.

Bamann, C., G. Nagel, and E. Bamberg. 2010. Microbial rhodopsins in the spotlight. Curr. Opin. Neurobiol. 20:610-616.

O'Brien, E. A., L. B. Koski, Y. Zhang, L. Yang, E. Wang, M. W. Gray, G. Burger, and B. F. Lang, 2007. TBestDB: a taxonomically broad database of expressed sequence tags (ESTs). Nucleic Acids Res. 2007 January; 35(Database issue): D445-D451.

Bogomolni, R. and J. L. Spudich (1982) Identification of a third rhodopsin-like pigment in phototactic *Halobacterium halobium*. Proc. Nati. Acad. Sci. USA 79, 6250-6254.

Spudich, J. L. and R. A. Bogomolni (1984) Mechanism of colour discrimination by a bacterial sensory rhodopsin. Nature 312, 509-513.

Foster, K.-W., J. Saranak, N. Patel, G. Zarrilli, M. Okabe, T. Kline and K. Nakanishi (1984) A rhodopsin is the functional photoreceptor for phototaxis in the unicellular eukaryote *Chlamydomonas*. Nature 311, 756-759.

Asamizu, E., K. Miura, K. Kucho, Y. Inoue, H. Fukuzawa, K. Ohyama, Y. Nakamura and S. Tabata (2000) Generation of expressed sequence tags from low-$CO_2$ and high-$CO_2$ adapted cells of *Chlamydomonas reinhardtii*. DNA Research 7, 305-307.

Kianianmomeni, A., K. Stehfest, G. Nematollahi, P. Hegemann and A. Hallmann (2009) Channelrhodopsins of *Volvox carteri* are photochromic proteins that are specifically expressed in somatic cells under control of light, temperature, and the sex inducer. Plant. Physiol. 151, 347-366.

Govorunova, E. G., E. N. Spudich, C. E. Lane, O. A. Sineshchekov and J. L. Spudich (2011) New channelrhodopsin with a red-shifted spectrum and rapid kinetics from *Mesostigma viride*. MBio 2, e00115-11.

Chow, B. Y., A. S. Chuong, N. C. Klapoetke and E. S. Boyden (2011) Synthetic physiology strategies for adapting tools from nature for genetically targeted control of fast biological processes. Methods Enzymol. 497, 425-443.

Kokaia, M. and A. T. Sorensen (2011) The treatment of neurological diseases under a new light: the importance of optogenetics. Drugs Today (Banc) 47, 53-62.

Tomita, H., E. Sugano, H. Isago and M. Tamai (2009) Channelrhodopsins provide a breakthrough insight into strategies for curing blindness. J. Genet. 88, 409-415.

Doroudchi, M. M., K. P. Greenberg, J. Liu, K. A. Silka, E. S. Boyden, J. A. Lockridge, A. C. Arman, R. Janani, S. E. Boye, S. L. Boye, G. M. Gordon, B. C. Matteo, A. P. Sampath, W. W. Hauswirth and A. Horsager (2011) Virally delivered channelrhodopsin-2 safely and effectively restores visual function in multiple mouse models of blindness. Mol. Ther. 19, 1220-1229.

Hoham, R. W. and B. Duval (2001) Microbial ecology of snow and freshwater ice with emphasis on snow algae. In *Snow Ecology: an Interdisciplinary Examination of Snow-covered Ecosystems*. (Edited by H. G. Jones, J. W. Pomeroy, D. A. Walker and R. W. Hoham), pp. 168-228. Cambridge University Press, Cambridge.

Morgan-Kiss, R. M., J. C. Priscu, T. Pocock, L. Gudynaite-Savitch and N. P. Huner (2006) Adaptation and acclimation of photosynthetic microorganisms to permanently cold environments. Microbiol. Mol. Biol. Rev. 70, 222-252.

Starr, R. C. and J. A. Zeikus (1993) UTEX—the culture collection of algae at the University of Texas at Austin. J. Phycol. 29 (suppl.), 1-106.

Bischoff, H. W. and H. C. Bold (1963) Phycological studies IV. Some soil algae from Enchanted Rock and related algal species. University of Texas Publication 6318, 1-95.

Hancock, J. M. and M. Simon (2005) Simple sequence repeats in proteins and their significance for network evolution. Gene 345, 113-118.

Xiao, H. and K. T. Jeang (1998) Glutamine-rich domains activate transcription in yeast *Saccharomyces cerevisiae*. J. Biol. Chem. 273, 22873-22876.

Weiss, J. L., N. A. Evans, T. Ahmed, J. D. Wrigley, S. Khan, C. Wright, J. N. Keen, A. Holzenburg and J. B. Findlay (2005) Methionine-rich repeat proteins: a family of membrane-associated proteins which contain unusual repeat regions. *Biochim. Biophys. Acta* 1668, 164-174.

Mittelmeier, T. M., J. S. Boyd, M. R. Lamb and C. L. Dieckmann (2011) Asymmetric properties of the *Chlamydomonas reinhardtii* cytoskeleton direct rhodopsin photoreceptor localization. *J. Cell. Biol.* 193, 741-753.

Hart, G. W. (2009) Nuclear and cytoplasmic glycosylation. In *Essentials of Glycobiology*. (Edited by A. Varki, R. Cummings, J. Esko, H. H. Freeze, P. Stanley, C. R. Bertozzi, G. W. Hart and M. E. Etzler), pp. 171-182. Cold Spring Harbor Laboratory Press, Cold Spring Harbor.

Kirsch, T. (2007) Functional expression of channelrhodopsin 2 (ChR2) in the methylotrophic yeast *Pichia pastoris* and its biophysical characterization. Ph. D. Thesis, J. W. Goethe University, Frankfurt.

Wagner, V., K. Ullmann, A. Mollwo, M. Kaminski, M. Mittag and G. Kreimer (2008) The phosphoproteome of a *Chlamydomonas reinhardtii* eyespot fraction includes key proteins of the light signaling pathway. *Plant Physiol.* 146, 772-788.

Violot, S., N. Aghajari, M. Czjzek, G. Feller, G. K. Sonan, P. Gouet, C. Gerday, R. Haser and V. Receveur-Brechot (2005) Structure of a full length psychrophilic cellulase from *Pseudoalteromonas haloplanktis* revealed by X-ray diffraction and small angle X-ray scattering. *J. Mol. Biol.* 348, 1211-24.

Thorvaldsen, S., E. Hjerde, C. Fenton and N. P. Willassen (2007) Molecular characterization of cold adaptation based on ortholog protein sequences from *Vibrionaceae* species. *Extremophiles* 11, 719-732.

Kleinlogel, S., K. Feldbauer, R. E. Dempski, H. Fotis, P. G. Wood, C. Bamann and E. Bamberg (2011) Ultra light-sensitive and fast neuronal activation with the $Ca^{2+}$-permeable channelrhodopsin CatCh. *Nat. Neurosci.* 14, 513-518.

Berndt, A., P. Schoenenberger, J. Mattis, K. M. Tye, K. Deisseroth, P. Hegemann and T. G. Oertner (2011) High-efficiency channelrhodopsins for fast neuronal stimulation at low light levels. *Proc. Natl. Acad. Sci. USA* 108, 7595-7600.

Frassanito, A. M., L. Barsanti, V. Passarelli, V. Evangelista and P. Gualtieri (2010) A rhodopsin-like protein in *Cyanophora paradoxa*: gene sequence and protein immuno-localization. *Cell. Mol. Life Sci.* 67, 965-971.

Williams, C. R. and M. A. Bees (2011) A tale of three taxes: photo-gyro-gravitactic bioconvection. *J. Exp. Biol.* 214, 2398-2408.

Lanyi, J. K. (2006) Proton transfers in the bacteriorhodopsin photocycle. *Biochim. Biophys. Acta* 1757, 1012-1018.

Balashov, S. P., E. S. Imasheva, T. G. Ebrey, N. Chen, D. R. Menick and R. K. Crouch (1997) Glutamate-194 to cysteine mutation inhibits fast light-induced proton release in bacteriorhodopsin. *Biochemistry* 36, 8671-8676.

Spudich, J. L. (2006) The multitalented microbial sensory rhodopsins, *Trends Microbiol.* 14, 480-487.

LaLumiere, R. T. (2011) A new technique for controlling the brain: optogenetics and its potential for use in research and the clinic, *Brain Stimul.* 4, 1-6.

Schoenenberger, P., Scharer, Y. P., and Oertner, T. G. (2011) Channelrhodopsin as a tool to investigate synaptic transmission and plasticity, *Exp. Physiol.* 96, 34-39.

Yizhar, O., Fenno, L., Zhang, F., Hegemann, P., and Diesseroth, K. (2011) Microbial opsins: a family of single-component tools for optical control of neural activity, *Cold Spring Harb. Protoc.* 2011, top 102.

Arrenberg, A. B., Stainier, D. Y., Baier, H., and Huisken, J. (2010) Optogenetic control of cardiac function, *Science* 330, 971-974.

Figueiredo, M., Lane, S., Tang, F., Liu, B. H., Hewinson, J., Marina, N., Kasymov, V., Souslova, E. A., Chudakov, D. M., Gourine, A. V., Teschemacher, A. G., and Kasparov, S. (2011) Optogenetic experimentation on astrocytes, *Exp. Physiol.* 96, 40-50.

Spudich, J. L., and Jung, K.-H. (2005) Microbial rhodopsins: phylogenetic and functional diversity, In *Handbook of Photosensory Receptors*, pp 1-23, Wiley-VCH, Weinheim.

Oesterhelt, D., and Stoeckenius, W. (1971) Rhodopsin-like protein from the purple membrane of *Halobacterium halobium*, *Nature* 233, 149-152.

Brown, L., and Jung, K. (2006) Bacteriorhodopsin-like proteins of eubacteria and fungi: the extent of conservation of the haloarchaeal proton-pumping mechanism, *Photochem. Photobiol. Sci.* 5, 538-546.

Chow, B. Y., Han, X., Dobry, A. S., Qian, X., Chuong, A. S., Li, M., Henninger, M. A., Belfort, G. M., Lin, Y., Monahan, P. E., and Boyden, E. S. (2010) High-performance genetically targetable optical neural silencing by light-driven proton pumps, *Nature* 463, 98-102.

Mukohata, Y., Ihara, K., Tamura, T., and Sugiyama, Y. (1999) Halobacterial rhodopsins, *J. Biochem.* 125, 649-657.

Han, X., Chow, B. Y., Zhou, H., Klapoetke, N. C., Chuong, A., Rajimehr, R., Yang, A., Baratta, M. V., Winkle, J., Desimone, R., and Boyden, E. S. (2011) A high-light sensitivity optical neural silencer: development and application to optogenetic control of non-human primate cortex, *Front. Syst. Neurosci.* 5, 18.

Hou, S.-Y., Govorunova, E. G., Ntefidou, M., Lane, C. E., Spudich, E. N., Sineshchekov, O. A., and Spudich, J. L. (2011) Diversity of *Chlamydomonas* channelrhodopsins, *Photochem.*

Jokela-Maatta, M., Pahlberg, J., Lindstrom, M., Zak, P. P., Porter, M., Ostrovsky, M. A., Cronin, T. W., and Donner, K. (2005) Visual pigment absorbance and spectral sensitivity of the *Mysis relicta* species group (Crustacea, Mysida) in different light environments, *J. Comp. Physiol. A: Neuroethol. Sens. Neural. Behav. Physiol.* 191, 1087-1097.

Ala-Laurila, P., Donner, K., Crouch, R. K., and Cornwall, M. C. (2007) Chromophore switch from 11-cis-dehydroretinal (A2) to 11-cis-retinal (A1) decreases dark noise in salamander red rods, *J. Physiol.* 585, 57-74.

Toyama, M., Hironaka, M., Yamahama, Y., Horiguchi, H., Tsukada, O., Uto, N., Ueno, Y., Tokunaga, F., Seno, K., and Hariyama, T. (2008) Presence of rhodopsin and porphyropsin in the eyes of 164 fishes, representing marine, diadromous, coastal and freshwater species—a qualitative and comparative study, *Photochem. Photobiol.* 84, 996-1002.

Dartnall, H. J., and Lythgoe, J. N. (1965) The spectral clustering of visual pigments, *Vision Res.* 5, 81-100.

Carleton, K. (2009) Cichlid fish visual systems: mechanisms of spectral tuning, *Integr. Zool.* 4, 75-86.

Tokunaga, F., and Ebrey, T. (1978) The blue membrane: the 3-dehydroretinal-based artificial pigment of the purple membrane, *Biochemistry* 17, 1915-1922.

Spudich, J. L., McCain, D. A., Nakanishi, K., Okabe, M., Shimizu, N., Rodman, H., Honig, B., and Bogomolni, R. A. (1986) Chromophore/protein interaction in bacterial sensory rhodopsin and bacteriorhodopsin, *Biophys. J.* 49, 479-483.

Lanyi, J. K., Zimanyi, L., Nakanishi, K., Derguini, F., Okabe, M., and Honig, B. (1988) Chromophore/protein and chromophore/anion interactions in halorhodopsin, *Biophys. J.* 53, 185-191.

Takahashi, T., Yan, B., Mazur, P., Derguini, F., Nakanishi, K., and Spudich, J. L. (1990) Color regulation in the archaebacterial phototaxis receptor phoborhodopsin (sensory rhodopsin II), *Biochemistry* 29, 8467-8474.

Jung, K.-H., Trivedi, V. D., and Spudich, J. L. (2003) Demonstration of a sensory rhodopsin in eubacteria, *Mol. Microbiol.* 47, 1513-1522.

Wang, W.-W., Sineshchekov, O. A., Spudich, E. N., and Spudich, J. L. (2003) Spectroscopic and photochemical characterization of a deep ocean proteorhodopsin, *J. Biol. Chem.* 278, 33985-33991.

Sineshchekov, O., and Spudich, J. (2004) Light-induced intramolecular charge movements in microbial rhodopsins in intact *E. coli* cells, *Photochem. Photobiol. Sci.* 3, 548-554.

Bridges, C. D. (1967) Spectroscopic properties of porphyropsins, *Vision Res.* 7, 349-369.

Crouch, R., Nodes, B. R., Perlman, J. I., Pepperberg, D. R., Akita, H., and Nakanishi, K. (1984) Cycloheptatrienylidene analog of 11-cis retinal. Formation of pigment in photoreceptor membranes, *Invest. Ophthalmol. Vis. Sci.* 25, 419-428.

Brueggemann, L. I., and Sullivan, J. M. (2002) HEK293S cells have functional retinoid processing machinery, *J. Gen. Physiol.* 119, 593-612.

Rollman, O., Wood, E. J., Olsson, M. J., and Cunliffe, W. J. (1993) Biosynthesis of 3,4-didehydroretinol from retinol by human skin keratinocytes in culture, *Biochem. J.* 293 (Pt 3), 675-682.

Azuma, M., Irie, T., and Seki, T. (1993) Retinals and retinols induced by estrogen in the blood plasma of *Xenopus laevis, J. Exp. Biol.* 178, 89-96.

Wald, G., Brown, P. K., and Smith, P. H. (1953) Cyanopsin, a new pigment of cone vision, *Science* 118, 505-508.

Parry, J. W., and Bowmaker, J. K. (2000) Visual pigment reconstitution in intact goldfish retina using synthetic retinaldehyde isomers, *Vision Res.* 40, 2241-2247.

Without further elaboration, it is believed that one skilled in the art can, using the description herein, utilize the present methods to its fullest extent. The embodiments described herein are to be construed as illustrative and not as constraining the remainder of the disclosure in any way whatsoever. While preferred embodiments have been shown and described, many variations and modifications thereof can be made by one skilled in the art without departing from the spirit and teachings of the presently disclosed methods. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they are consistent with the present disclosure set forth herein.

---

What is claimed is:

1. A cDNA nucleic acid operatively linked to a heterologous promoter sequence, said nucleic acid comprising:
   a) a sequence that encodes a peptide with at least 95% homology to an amino acid sequence of SEQ ID NO: 3; wherein the nucleic acid encodes a red-shifted channelrhodopsin or
   b) a sequence that encodes a peptide comprising 225 contiguous amino acids of SEQ ID NO: 3; wherein the nucleic acid encodes a red-shifted channelrhodopsin or
   c) a sequence that hybridizes under highly stringent conditions to a nucleotide sequence that encodes amino acids of SEQ ID NO: 3, or a complement thereof, wherein the cDNA nucleic acid encodes helices b and c of a red-shifted channelrhodopsin helix domain, and wherein said highly stringent conditions comprise hybridizing to a filter-bound DNA in 0.5 M NaHPO4, 7% sodium dodecyl sulfate (SDS), and 1 mM EDTA at 65° C.; and washing in 0.1×SSC/0.1% SDS at 68° C.

2. An expression vector comprising the cDNA nucleic acid of claim 1.

3. An isolated recombinant host cell comprising the cDNA nucleic acid of claim 1.

4. The recombinant host cell of claim 3, wherein said host cell is an isolated stem cell.

5. The recombinant host cell of claim 3, wherein said host cell is an isolated cardiac cell.

6. The recombinant host cell of claim 3, wherein said host cell is an isolated human cell.

7. The recombinant host cell of claim 3, wherein said host cell is a non-human mammalian cell.

8. The recombinant host cell of claim 3, wherein said host cell is a bacterial cell.

9. The recombinant host cell of claim 3, wherein said host cell is a yeast cell.

10. The recombinant host cell of claim 3, wherein said host cell is an insect cell.

11. The recombinant host cell of claim 3, wherein said host cell is a plant cell.

12. The recombinant host cell of claim 3, wherein said host cell is an isolated neuronal cell.

13. The recombinant host cell of claim 3, wherein said host cell is an isolated electrically active cell.

* * * * *